(12) United States Patent
Gillick et al.

(10) Patent No.: US 10,149,778 B2
(45) Date of Patent: *Dec. 11, 2018

(54) METHODS AND SYSTEMS FOR DELIVERING AN IMPLANT USING A PLANETARY GEAR ACTUATION ASSEMBLY

(71) Applicant: ABBOTT CARDIOVASCULAR SYSTEMS INC., Santa Clara, CA (US)

(72) Inventors: Matthew J. Gillick, Murrieta, CA (US); Michael L. Green, Pleasanton, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 306 days.

This patent is subject to a terminal disclaimer.

(21) Appl. No.: 14/932,848

(22) Filed: Nov. 4, 2015

(65) Prior Publication Data
US 2016/0128856 A1 May 12, 2016

Related U.S. Application Data

(60) Provisional application No. 62/075,059, filed on Nov. 4, 2014.

(51) Int. Cl.
*A61F 2/966* (2013.01)
*F16H 19/04* (2006.01)
(Continued)

(52) U.S. Cl.
CPC ............ *A61F 2/966* (2013.01); *F16H 19/04* (2013.01); *F16H 57/02* (2013.01); *A61F 2002/9517* (2013.01)

(58) Field of Classification Search
CPC ...... A61F 2002/9665; A61F 2002/9517; A61F 2002/9522; A61F 2002/9528;
(Continued)

(56) References Cited

U.S. PATENT DOCUMENTS

| 3,148,595 A | 9/1964 | Looney |
| 5,344,061 A | 9/1994 | Crainich |

(Continued)

FOREIGN PATENT DOCUMENTS

| EP | 2190388 B1 | 3/2014 |
| WO | WO 2012/068389 A1 | 5/2012 |
| WO | WO 2016/073637 A1 | 5/2016 |

OTHER PUBLICATIONS

U.S. Appl. No. 14/560,832 (US 2016/0158049), filed Dec. 4, 2014 (Jun. 9, 2016).

(Continued)

*Primary Examiner* — Diane Yabut
*Assistant Examiner* — Erich Herbermann
(74) *Attorney, Agent, or Firm* — Baker Botts L.L.P.

(57) ABSTRACT

A system for delivering an implant including a handle, a trigger, and an actuation assembly. The actuation assembly can include a planet carrier, at least one planet gear operatively coupled to the planet carrier, a sun gear shaft operatively engaged with the planet gear, a ring gear operatively engaged with the planet gear, a first clutch driver, and a second clutch driver. The actuation assembly can be configured to displace the outer tubular member in the proximal direction a distance (d) relative to the handle and to separately move the inner shaft member distally a distance (x) relative to the handle upon deployment of the trigger from a first position to a second position, and move the inner shaft member proximally a distance (y) relative to the handle with no displacement of the outer tubular member upon return of the trigger from the second position to the first position.

31 Claims, 75 Drawing Sheets

(51) Int. Cl.
*F16H 57/02* (2012.01)
*A61F 2/95* (2013.01)

(58) Field of Classification Search
CPC .... A61F 2002/9534; A61F 2/966; A61F 2/97; A61F 2/95; A61F 2/962; A61F 2/954; A61F 2/958; A61F 2/93; F16H 19/04; F16H 57/02

See application file for complete search history.

(56) References Cited

U.S. PATENT DOCUMENTS

| | | | |
|---|---|---|---|
| 5,364,351 | A | 11/1994 | Heinzelman et al. |
| 5,443,477 | A | 8/1995 | Marin et al. |
| 5,507,769 | A | 4/1996 | Marin et al. |
| 5,607,466 | A | 3/1997 | Imbert et al. |
| 5,643,319 | A | 7/1997 | Green et al. |
| 5,707,376 | A | 1/1998 | Kavteladze et al. |
| 5,797,927 | A | 8/1998 | Yoon |
| 6,241,758 | B1 | 6/2001 | Cox |
| 6,514,261 | B1 | 2/2003 | Randall et al. |
| 6,676,693 | B1 | 1/2004 | Belding et al. |
| 6,945,989 | B1 | 9/2005 | Betelia et al. |
| 7,052,511 | B2 | 5/2006 | Weldon et al. |
| 7,326,203 | B2 | 2/2008 | Papineau et al. |
| 7,611,497 | B2 | 11/2009 | Wollschlager |
| 7,758,624 | B2 | 7/2010 | Dorn et al. |
| 7,854,746 | B2 | 12/2010 | Dorn et al. |
| 7,985,250 | B2 | 7/2011 | Kaufmann et al. |
| 8,025,692 | B2 | 9/2011 | Feeser |
| 8,292,939 | B2 | 10/2012 | Yachia et al. |
| 8,382,813 | B2 | 2/2013 | Shumer |
| 8,500,789 | B2 | 8/2013 | Wuebbeling et al. |
| 8,568,467 | B2 | 10/2013 | Dorn et al. |
| 8,603,045 | B2 | 12/2013 | Weber |
| 8,652,193 | B2 | 2/2014 | Dorn |
| 9,039,750 | B2 | 5/2015 | Ryan |
| 9,078,779 | B2 | 7/2015 | Dorn et al. |
| 9,095,465 | B2 | 8/2015 | Kelly |
| 9,149,379 | B2 | 10/2015 | Keady et al. |
| 9,192,500 | B1 | 11/2015 | Longo et al. |
| 2002/0068947 | A1 | 6/2002 | Kuhns et al. |
| 2003/0028236 | A1 | 2/2003 | Gillick et al. |
| 2003/0191516 | A1 | 10/2003 | Weldon et al. |
| 2005/0080476 | A1 | 4/2005 | Gunderson et al. |
| 2005/0149159 | A1 | 7/2005 | Andreas et al. |
| 2007/0156225 | A1 | 7/2007 | George et al. |
| 2007/0250150 | A1 | 10/2007 | Pal et al. |
| 2008/0161902 | A1 | 7/2008 | Poulson |
| 2008/0281336 | A1 | 11/2008 | Zergiebel |
| 2008/0319524 | A1 | 12/2008 | Yachia et al. |
| 2009/0024133 | A1 | 1/2009 | Keady et al. |
| 2010/0174290 | A1 | 7/2010 | Wueebbeling |
| 2012/0029607 | A1 | 2/2012 | McHugo et al. |
| 2012/0053671 | A1 | 3/2012 | McHugo et al. |
| 2012/0158117 | A1 | 6/2012 | Ryan |
| 2012/0172963 | A1* | 7/2012 | Ryan .............. A61F 2/966 623/1.11 |
| 2012/0221093 | A1 | 8/2012 | McHugo |
| 2012/0290066 | A1 | 11/2012 | Nabulsi et al. |
| 2014/0046428 | A1 | 2/2014 | Cragg et al. |
| 2014/0135909 | A1 | 5/2014 | Carr et al. |
| 2014/0180380 | A1 | 6/2014 | Kelly |
| 2014/0324151 | A1 | 10/2014 | Yamashita |
| 2016/0120678 | A1 | 5/2016 | Green et al. |

OTHER PUBLICATIONS

U.S. Appl. No. 14/560,832, Apr. 22, 2016 Non-Final Office Action.
U.S. Appl. No. 14/932,875, May 19, 2016 Non-Final Office Action.
U.S. Appl. No. 14/932,795, filed Nov. 4, 2015.
U.S. Appl. No. 14/932,805, filed Nov. 4, 2015.
U.S. Appl. No. 14/932,830, filed Nov. 4, 2015.
U.S. Appl. No. 14/932,862, filed Nov. 4, 2015.
U.S. Appl. No. 14/932,875, filed Nov. 4, 2015.
U.S. Appl. No. 14/932,884, filed Nov. 4, 2015.
U.S. Appl. No. 14/932,900, filed Nov. 4, 2015.
International Search report and Written Opinion dated Jan. 29, 2016 in International Application No. PCT/US2015/059070.
International Search report and Written Opinion dated Jan. 29, 2016 in International Application No. PCT/US2015/059074.
International Search report and Written Opinion dated Jan. 29, 2016 in International Application No. PCT/US2015/059084.
U.S. Appl. No. 14/932,795, Dec. 26, 2017 Non-Final Office Action.
U.S. Appl. No. 14/932,805, Dec. 26, 2017 Non-Final Office Action.
U.S. Appl. No. 14/932,900, Jan. 5, 2018 Restriction Requirement.
U.S. Appl. No. 14/932,830, Jan. 17, 2018 Restriction Requirement.
U.S. Appl. No. 14/932,862, Jan. 22, 2018 Restriction Requirement.
U.S. Appl. No. 14/932,875, Jul. 3, 2017 Issue Fee Payment.
U.S. Appl. No. 14/932,875, Apr. 5, 2017 Notice of Allowance.
U.S. Appl. No. 14/932,875, Mar. 29, 2017 Response after Final Action.
U.S. Appl. No. 14/932,875, Mar. 9, 2017 Applicant Initiated Interview Summary.
U.S. Appl. No. 14/932,875, Nov. 29, 2016 Final Office Action.
U.S. Appl. No. 14/932,875, Aug. 19, 2016 Response to Non-Final Office Action.
U.S. Appl. No. 14/560,832, Jun. 30, 2017 Issue Fee Payment.
U.S. Appl. No. 14/560,832, Mar. 31, 2017 Notice of Allowance.
U.S. Appl. No. 14/560,832, Mar. 21, 2017 Response after Final Action.
U.S. Appl. No. 14/560,832, Nov. 21, 2016 Final Office Action.
U.S. Appl. No. 14/560,832, Aug. 22, 2016 Response to Non-Final Office Action.
U.S. Appl. No. 15/670,719 (US 2017/0333238), filed Aug. 7, 2017 (Nov. 23, 2017).
U.S. Appl. No. 15/836,649, filed Dec. 8, 2017.
U.S. Appl. No. 29/628,958, filed Dec. 8, 2017.
International Search Report dated Apr. 4, 2018 in International Application No. PCT/US2017/065399.
U.S. Appl. No. 15/835,418, filed Dec. 7, 2017.
U.S. Appl. No. 14/932,795, filed Dec. 26, 2017 Non-Final Office Action.
U.S. Appl. No. 14/932,805, filed Dec. 26, 2017 Non-Final Office Action.
U.S. Appl. No. 14/932,900, filed Jan. 5, 2018 Restriction Requirement.
U.S. Appl. No. 14/932,830, filed Jan. 17, 2018 Restriction Requirement.
U.S. Appl. No. 14/932,862, filed Jan. 22, 2018 Restriction Requirement.
U.S. Appl. No. 14/932,875, filed Jul. 3, 2017 Issue Fee Payment.
U.S. Appl. No. 14/932,875, filed Apr. 5, 2017 Notice of Allowance.
U.S. Appl. No. 14/932,875, filed Mar. 29, 2017 Response after Final Action.
U.S. Appl. No. 14/932,875, filed Mar. 9, 2017 Applicant Initiated Interview Summary.
U.S. Appl. No. 14/932,875, filed Nov. 29, 2016 Final Office Action.
U.S. Appl. No. 14/932,875, filed Aug. 19, 2016 Response to Non-Final Office Action.
U.S. Appl. No. 14/560,832, filed Jun. 30, 2017 Issue Fee Payment.
U.S. Appl. No. 14/560,832, filed Mar. 31, 2017 Notice of Allowance.
U.S. Appl. No. 14/560,832, filed Mar. 21, 2017 Response after Final Action.
U.S. Appl. No. 14/560,832, filed Nov. 21, 2016 Final Office Action.
U.S. Appl. No. 14/560,832, filed Aug. 22, 2016 Response to Non-Final Office Action.
U.S. Appl. No. 14/932,830, filed Jun. 11, 2018 Non-Final Office Action.

* cited by examiner

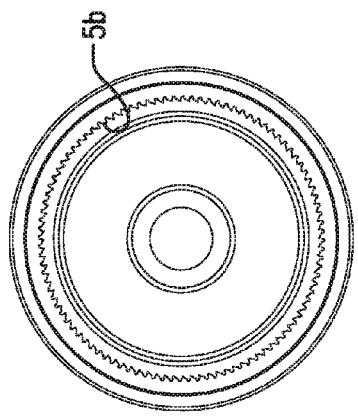
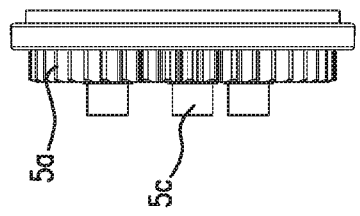
FIG. 6B
FIG. 6D
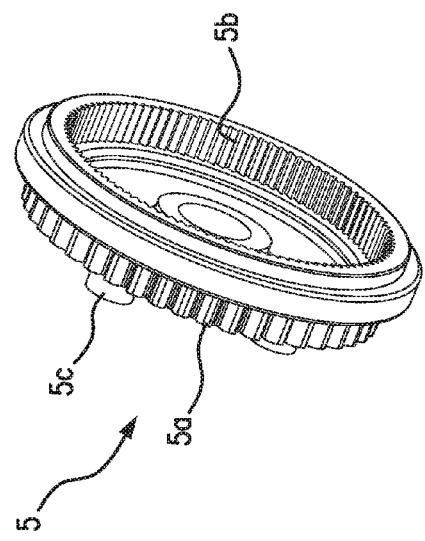
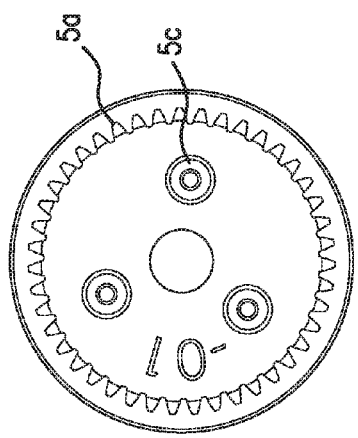
FIG. 6A
FIG. 6C

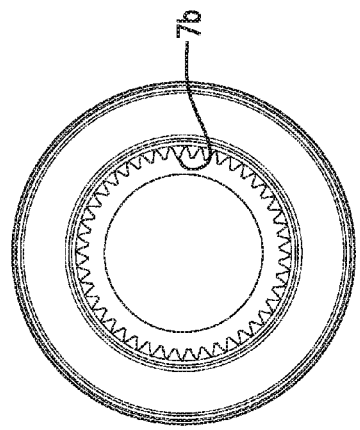
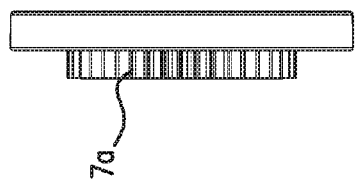
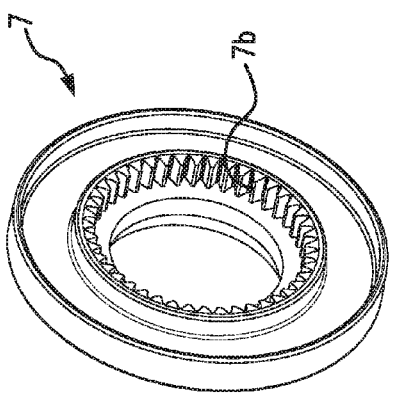
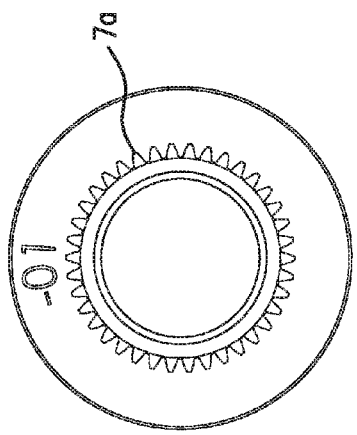

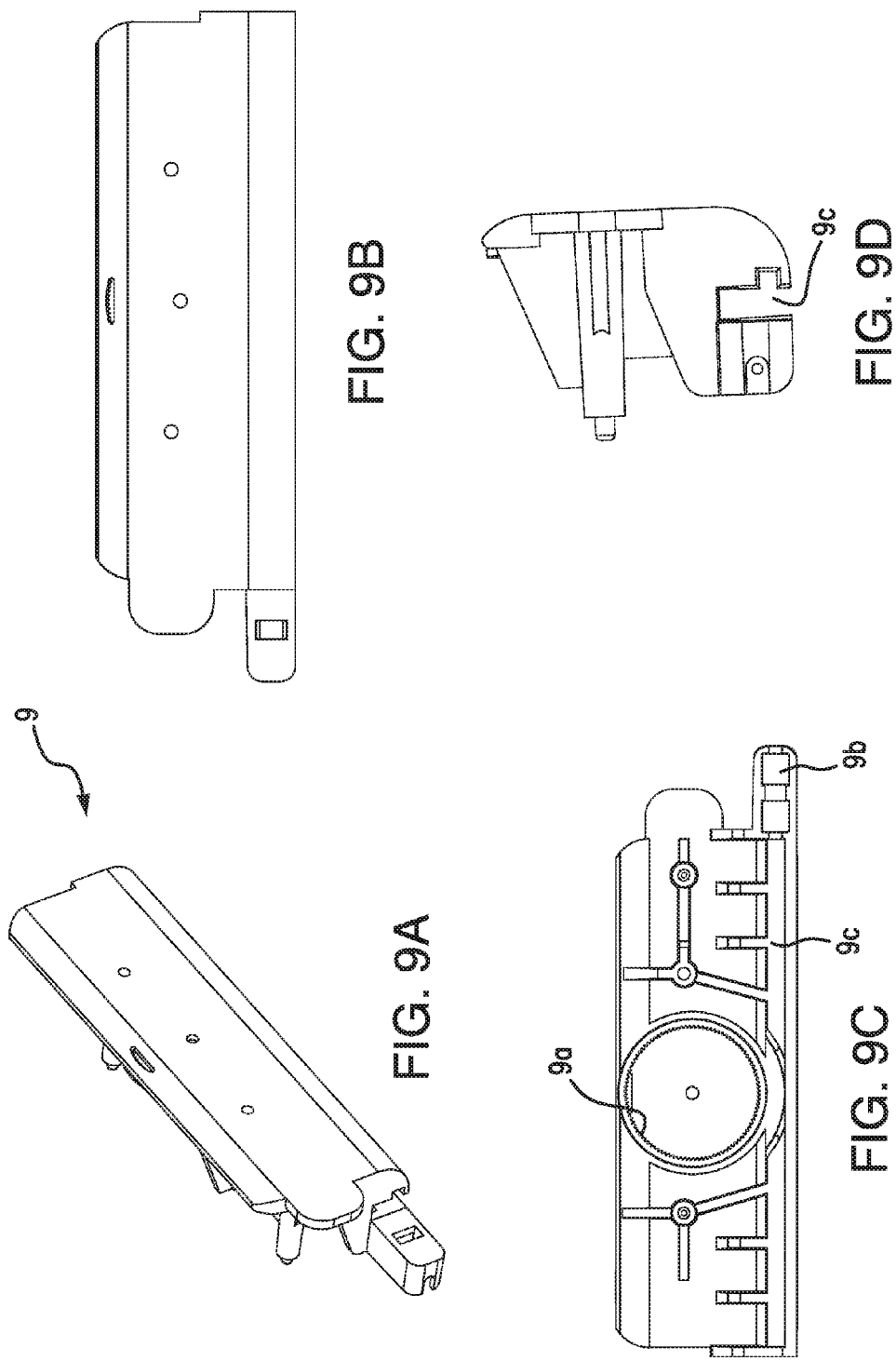

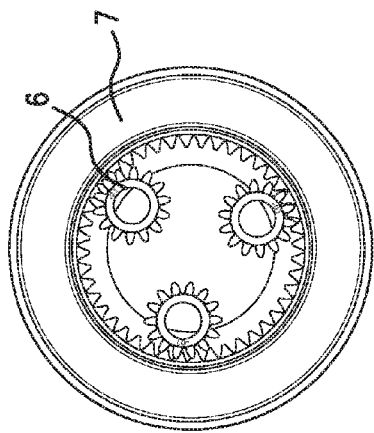
FIG. 14A
FIG. 14B
FIG. 14D
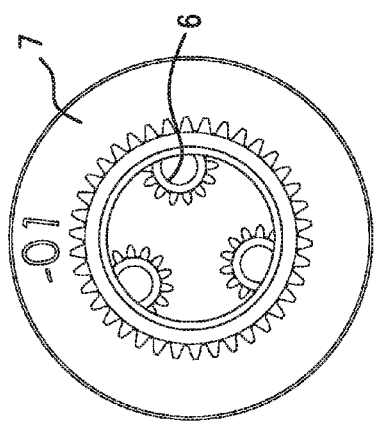
FIG. 14C

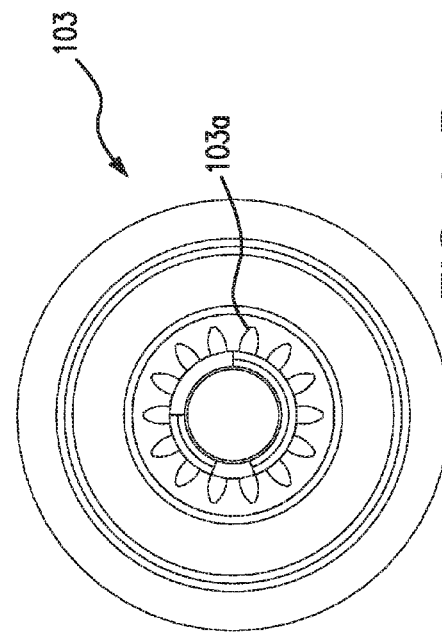
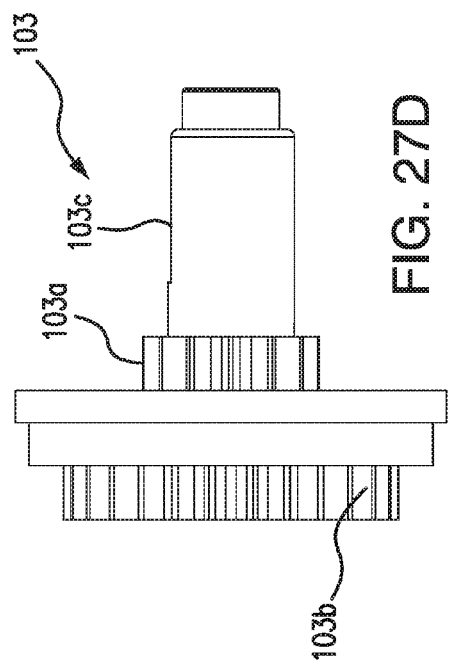
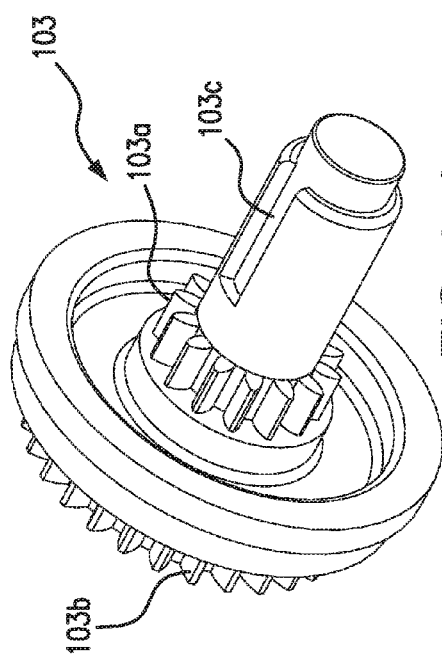
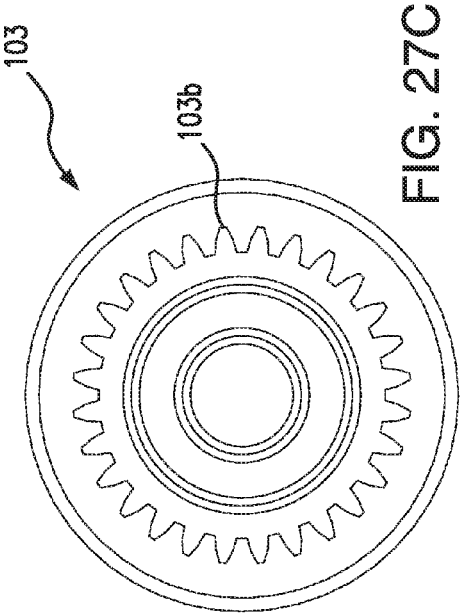
FIG. 27A
FIG. 27B
FIG. 27C
FIG. 27D

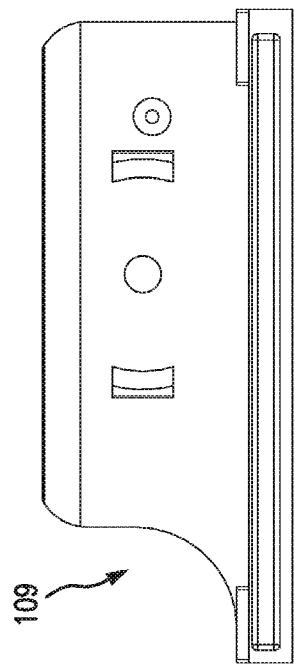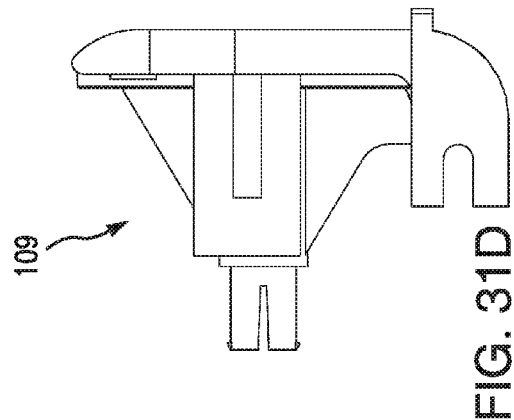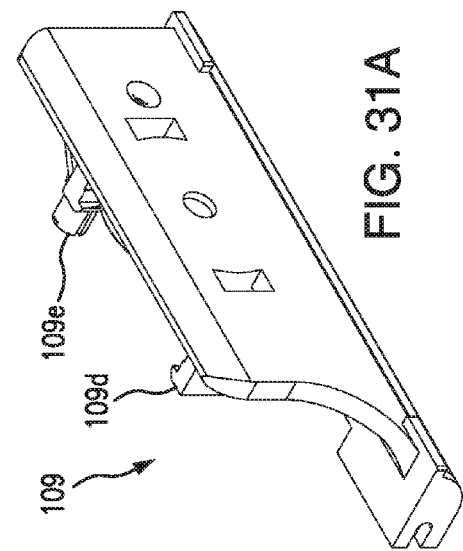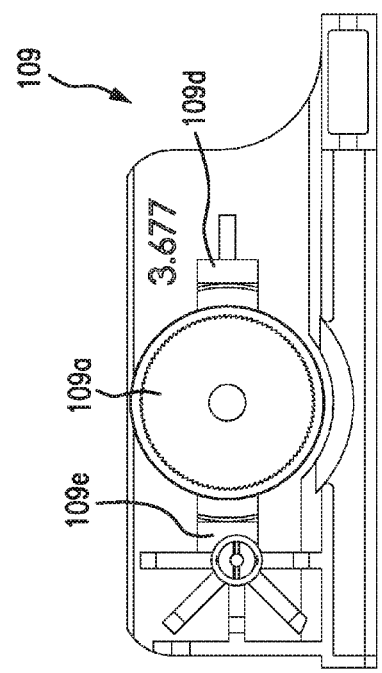

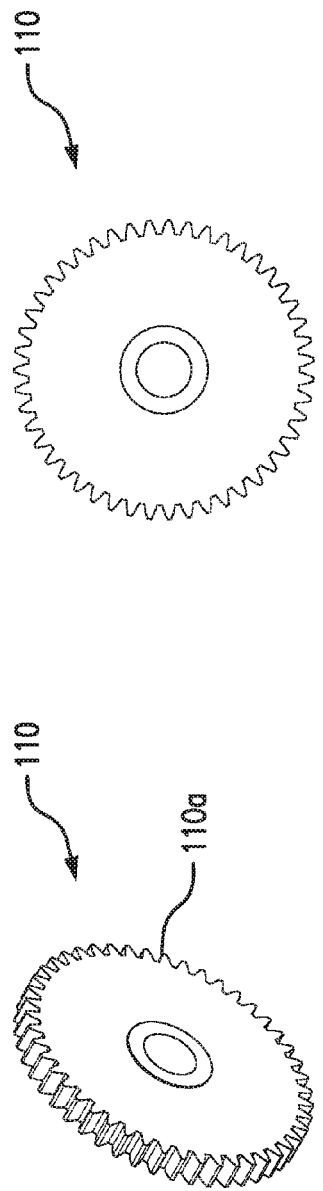
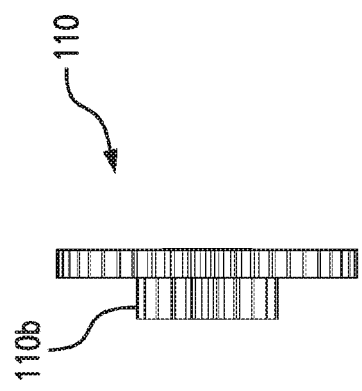
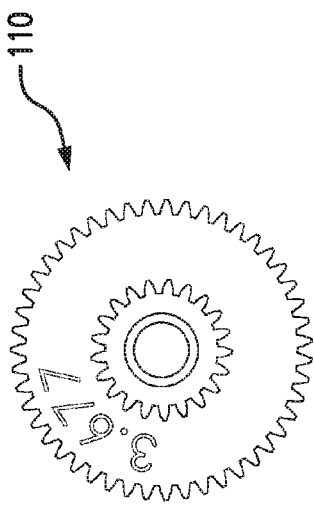
FIG. 32A
FIG. 32B
FIG. 32C
FIG. 32D

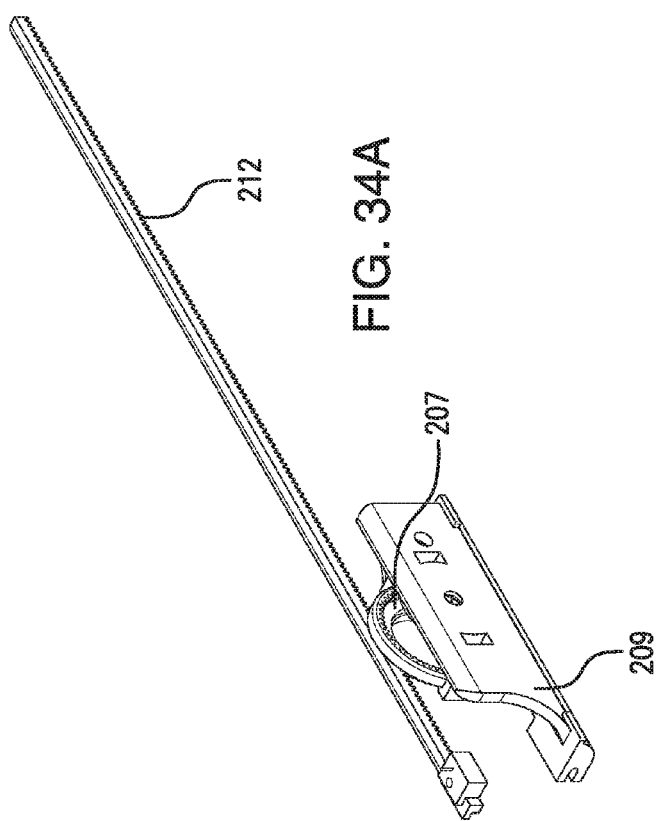
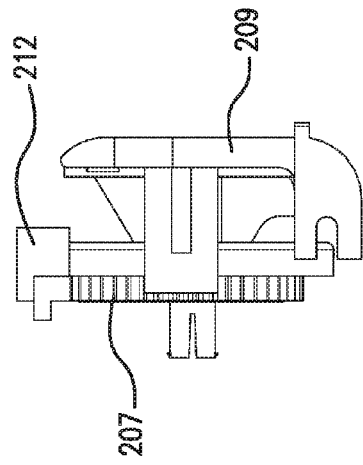
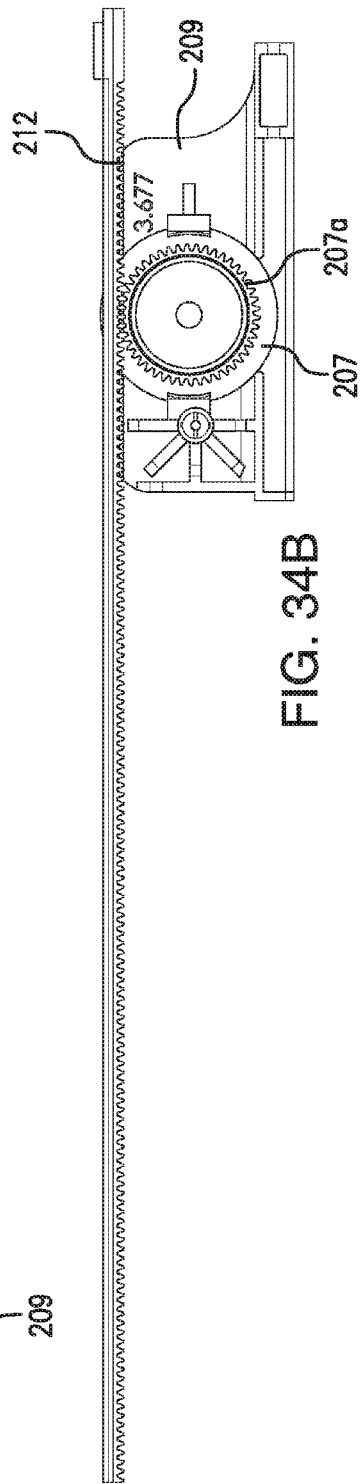
FIG. 34A
FIG. 34B
FIG. 34C

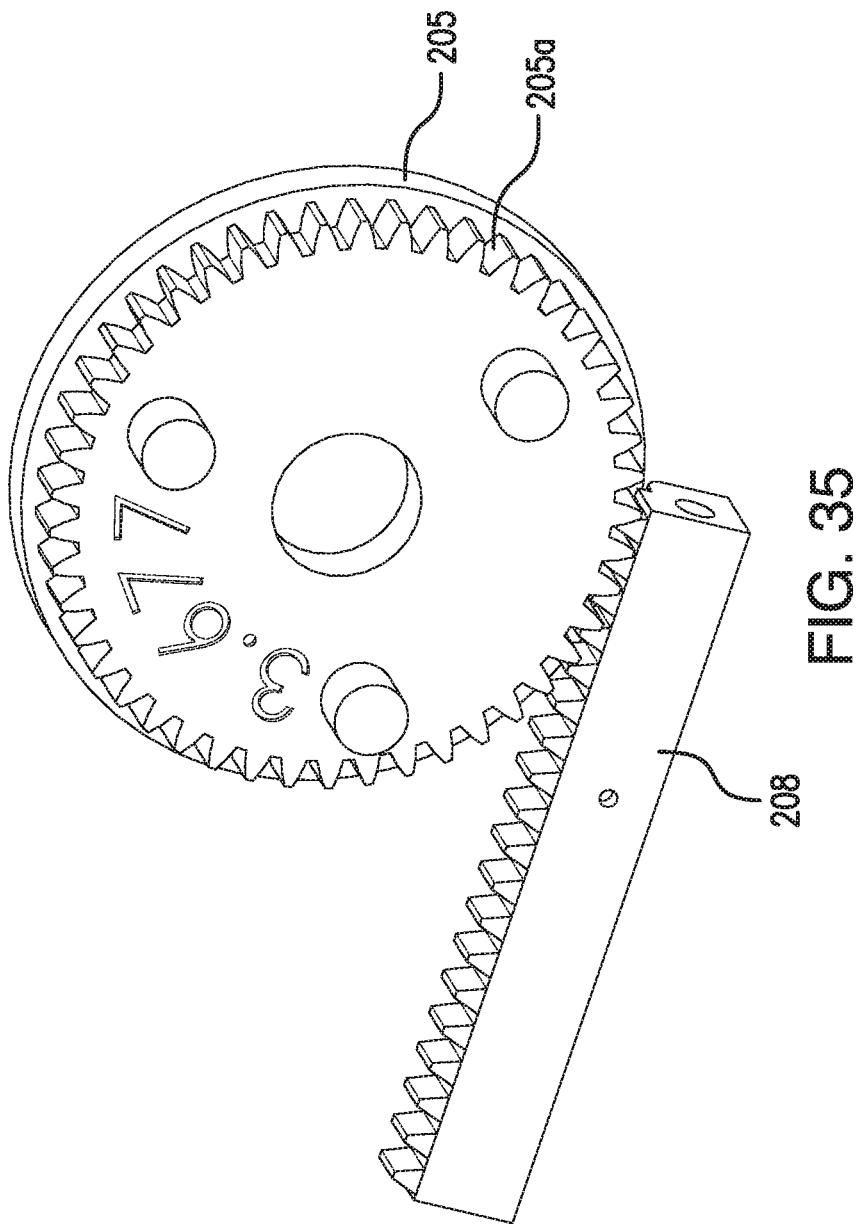

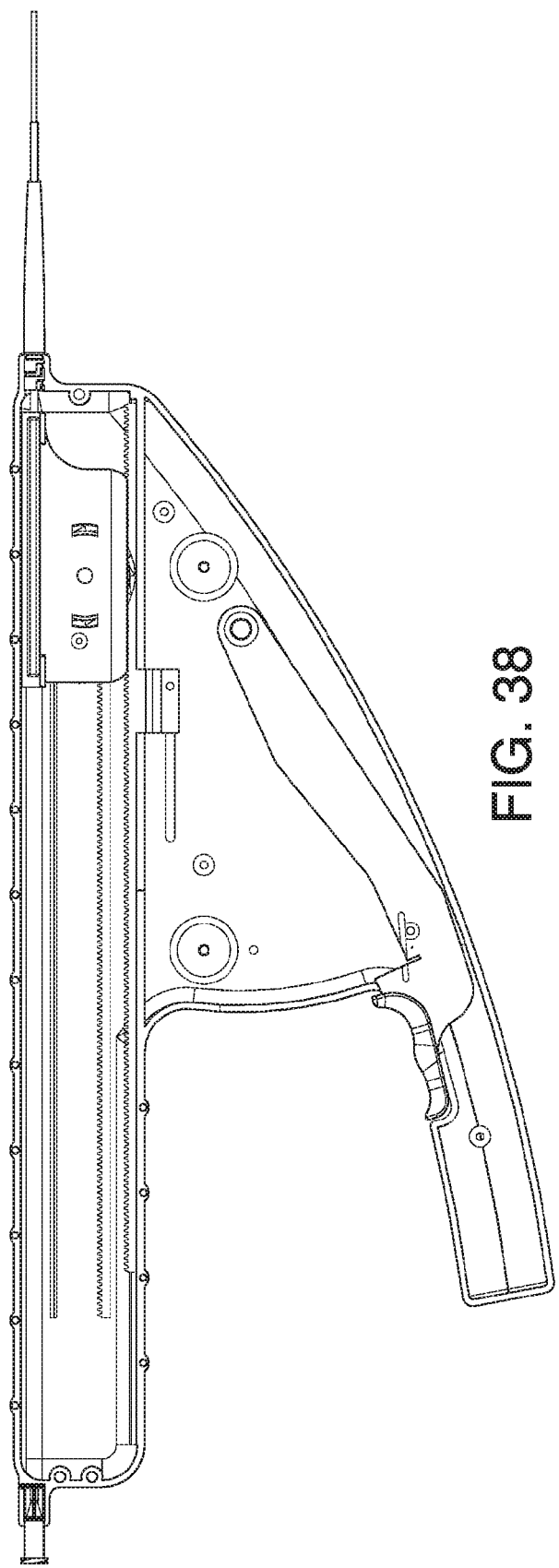

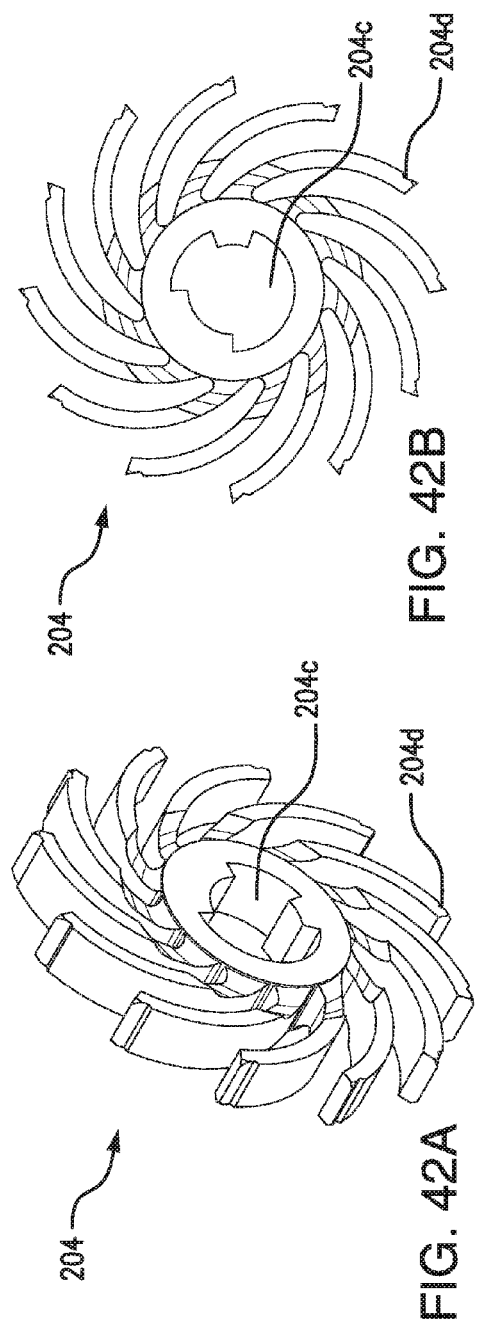
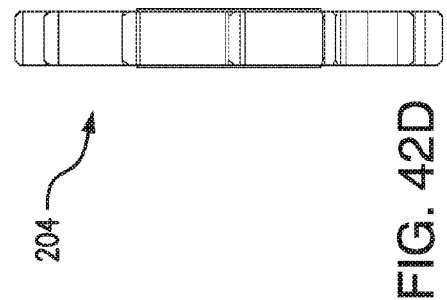
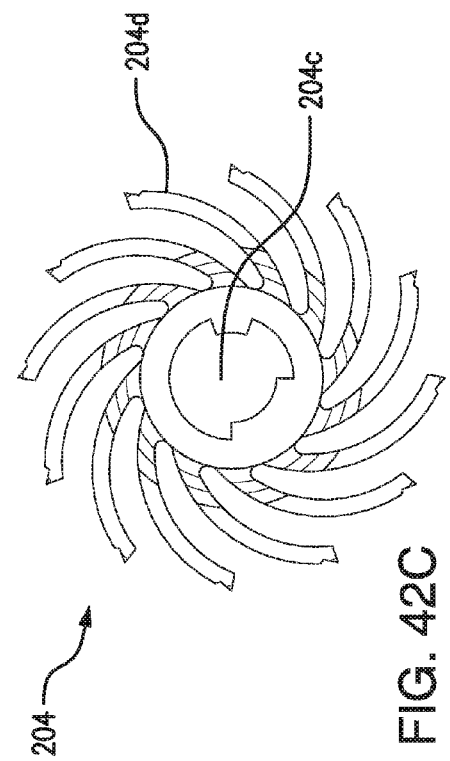
FIG. 42A
FIG. 42B
FIG. 42C
FIG. 42D

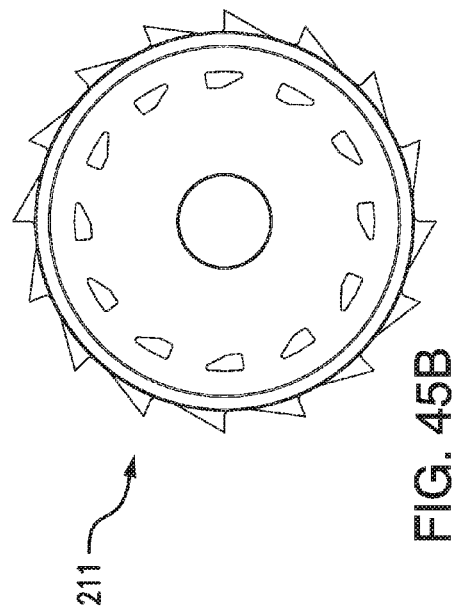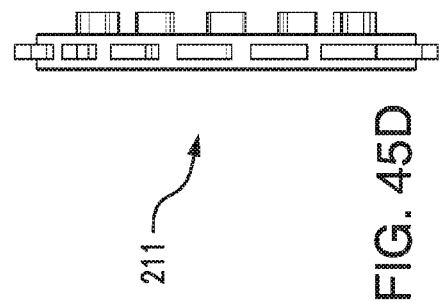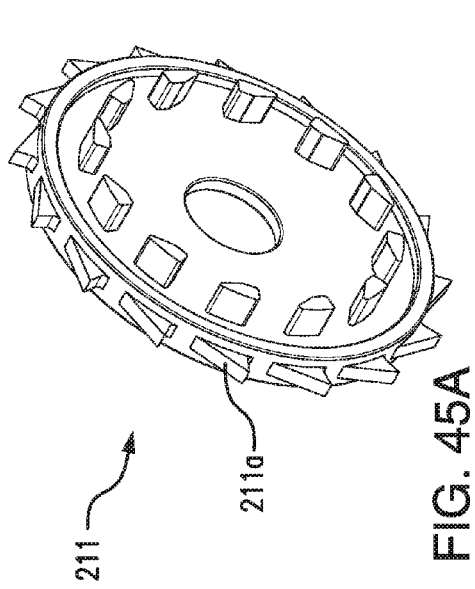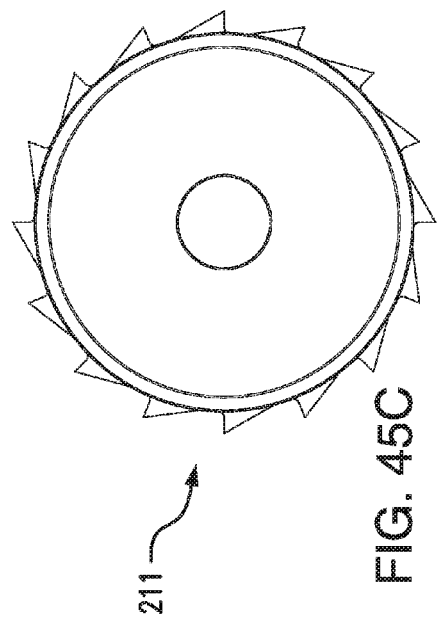

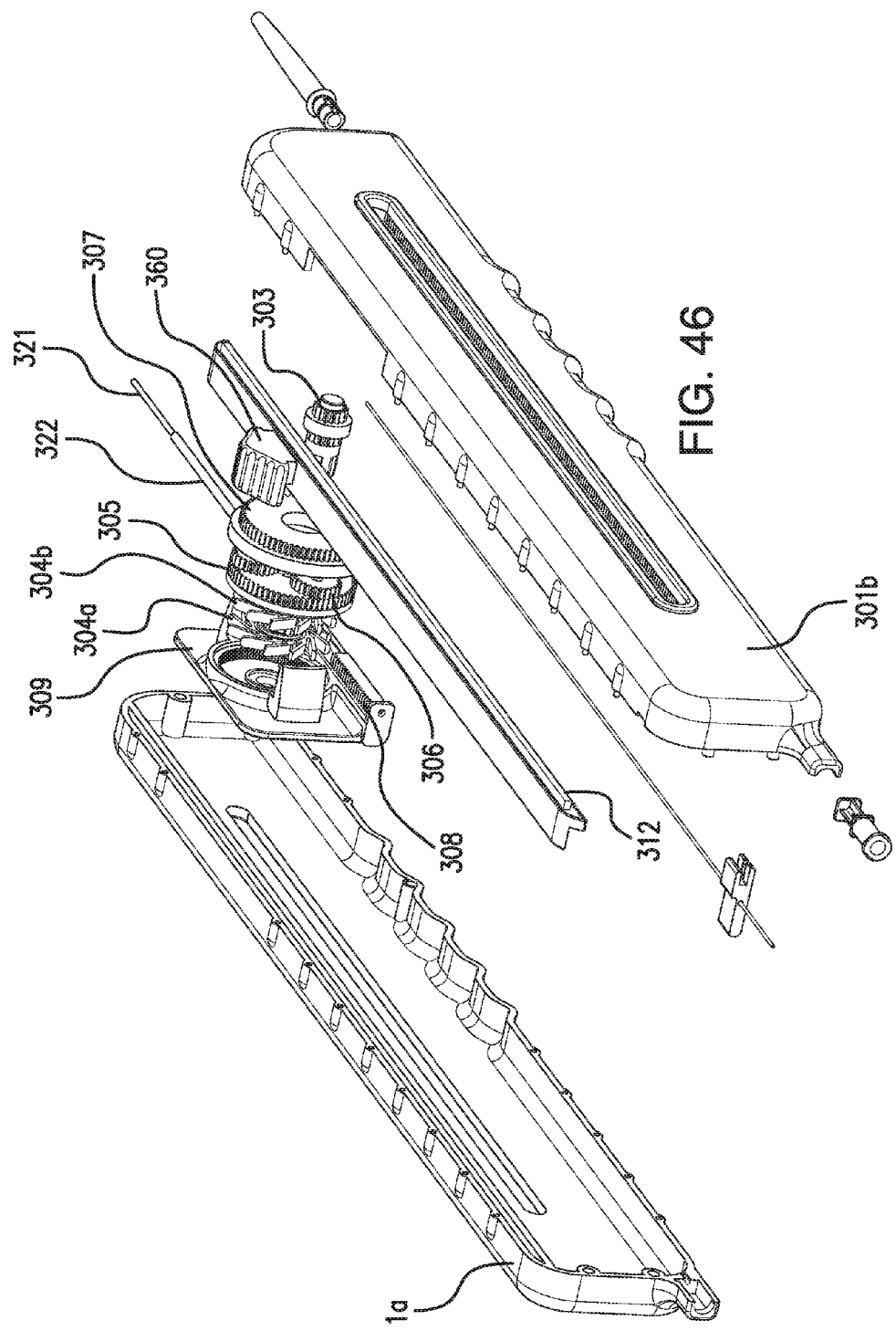

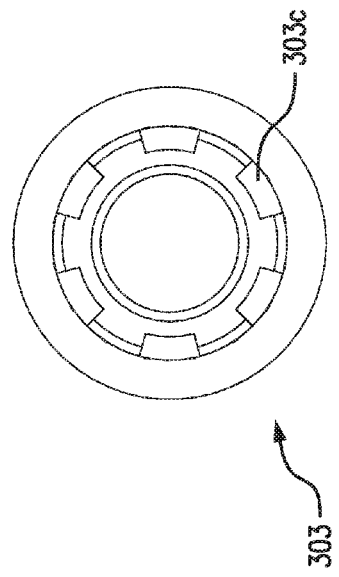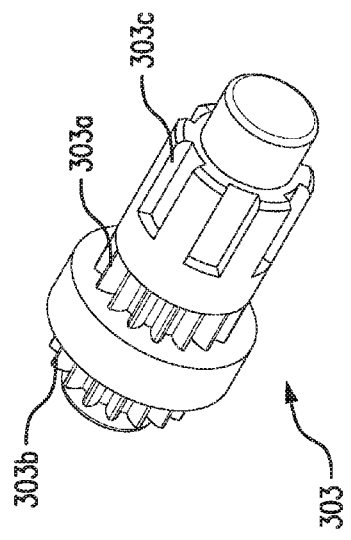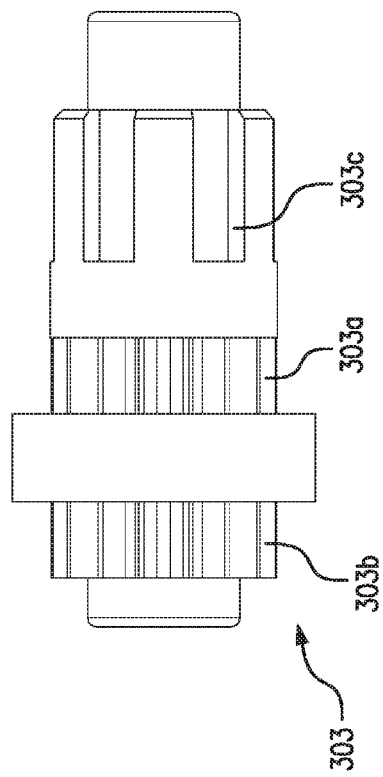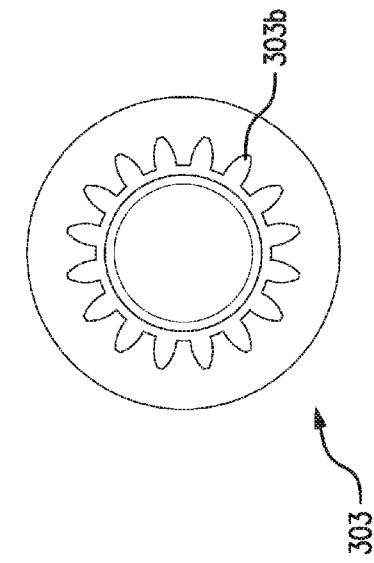

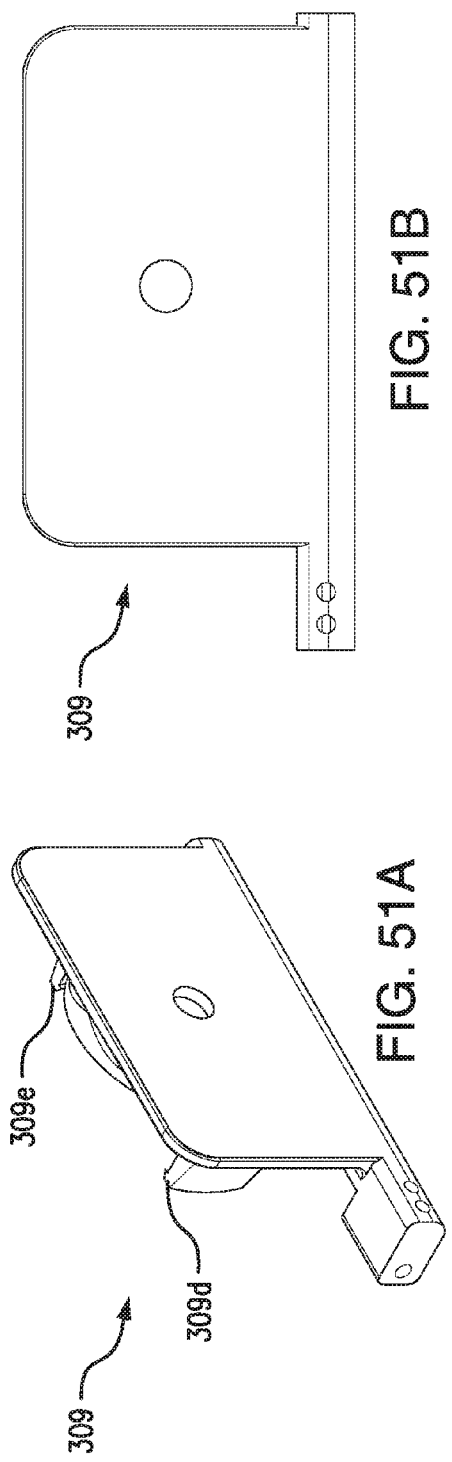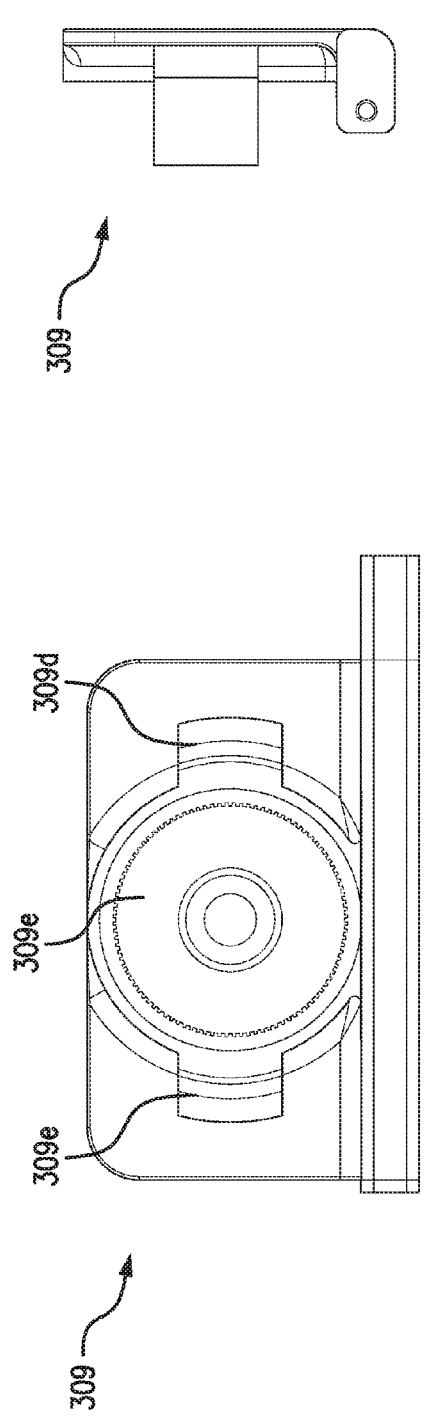

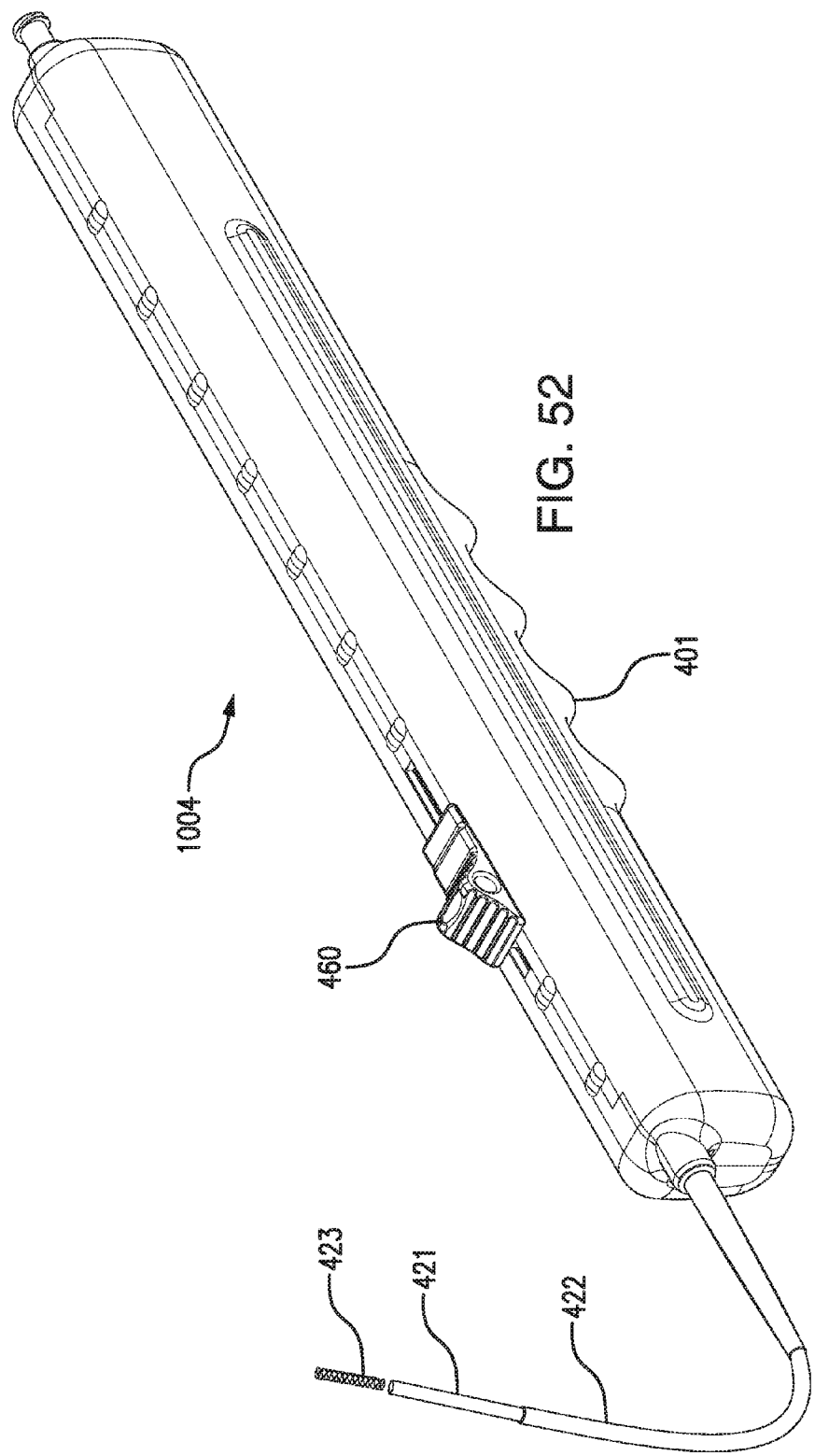

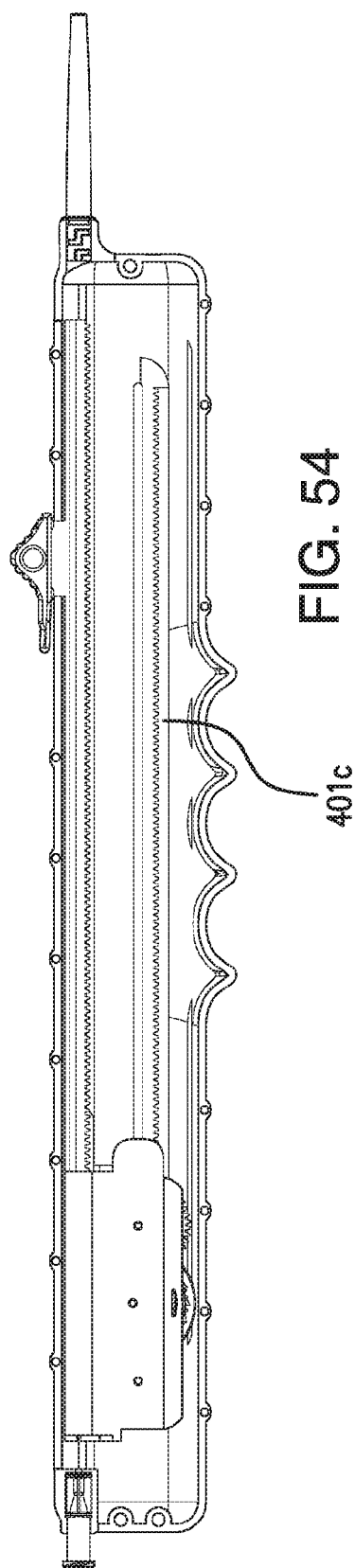

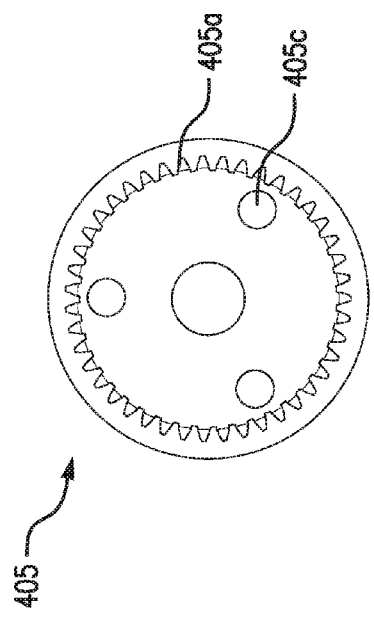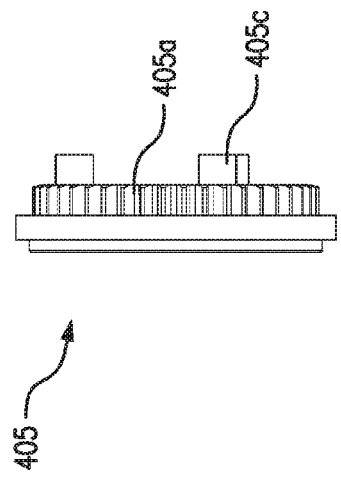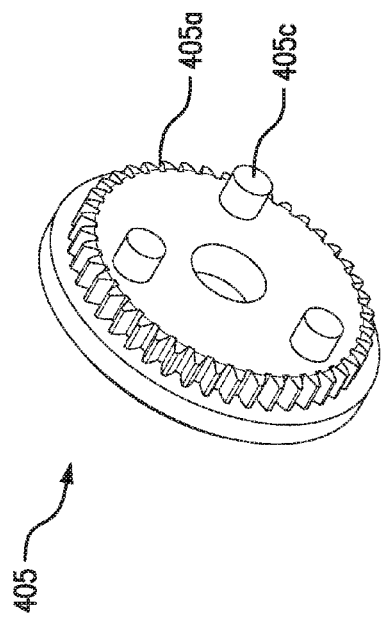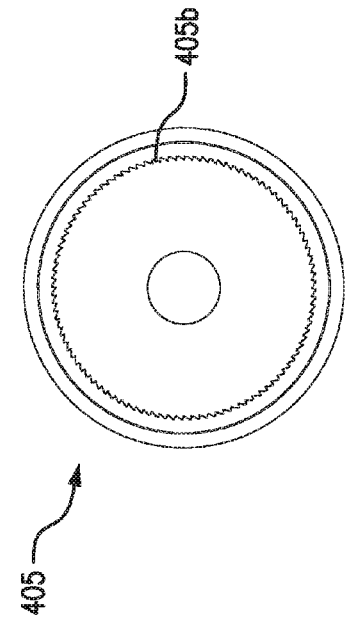

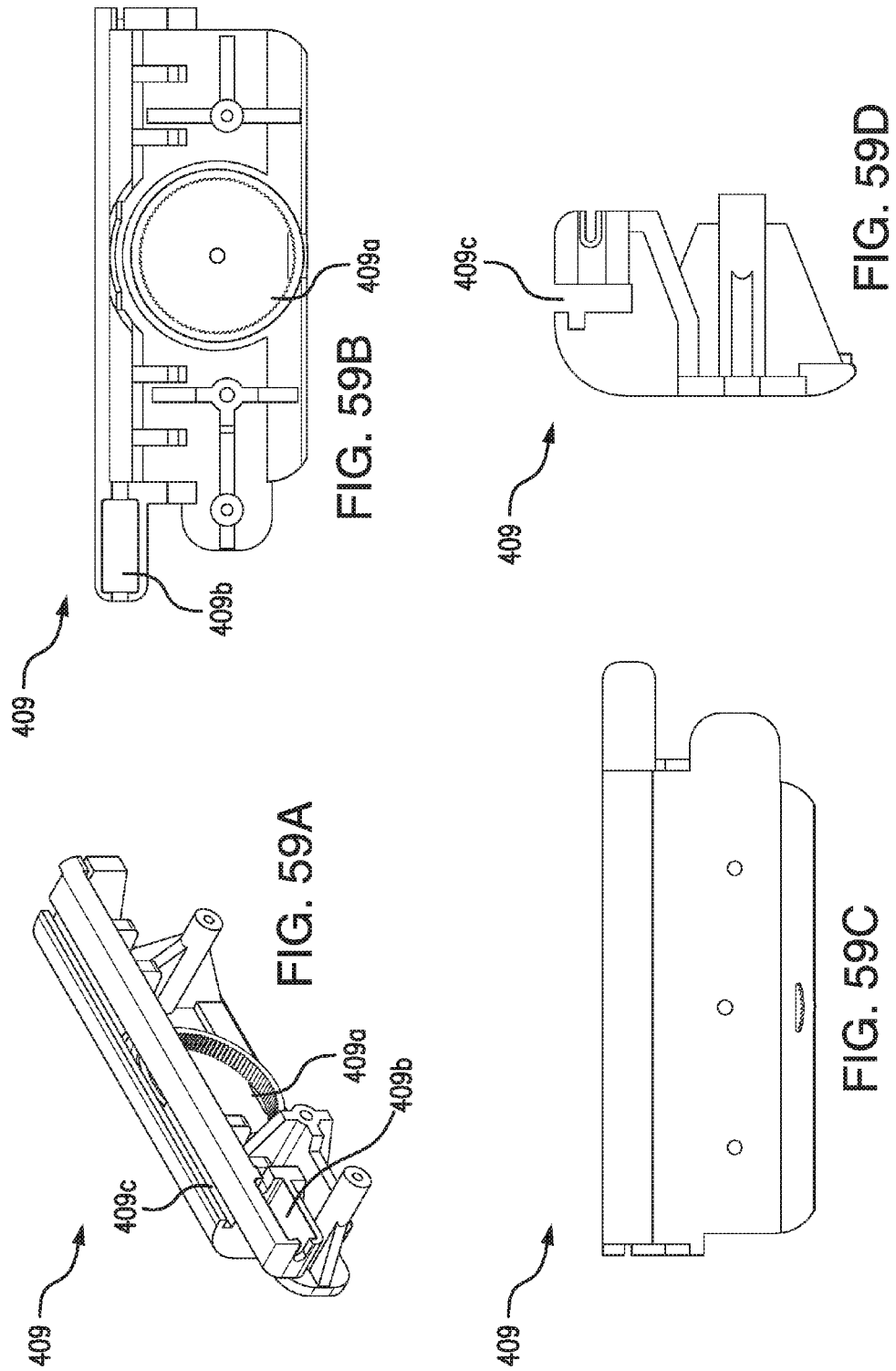

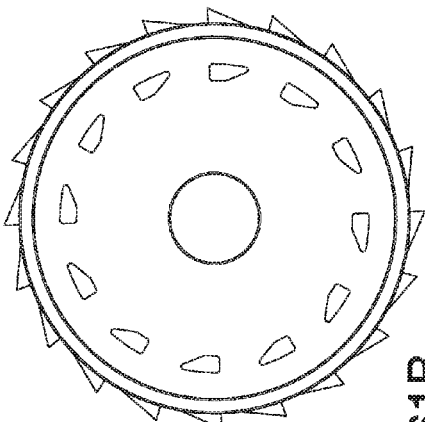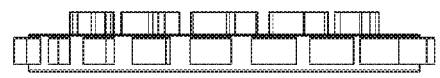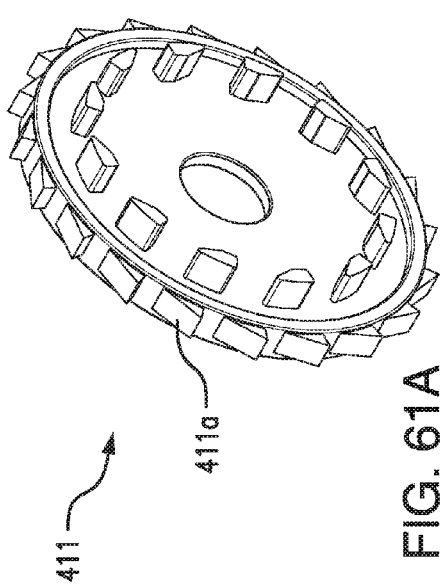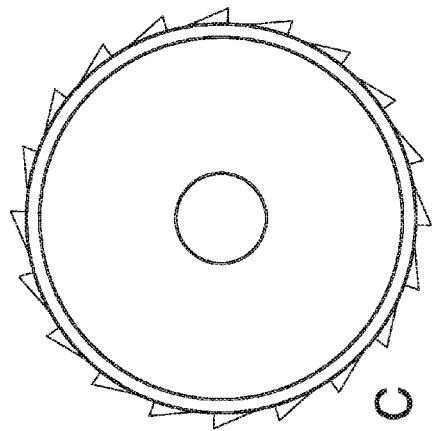

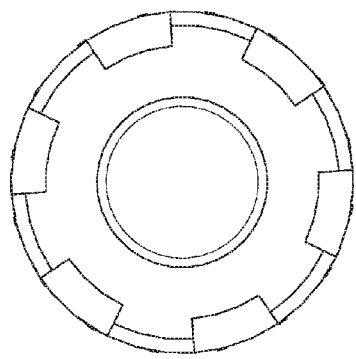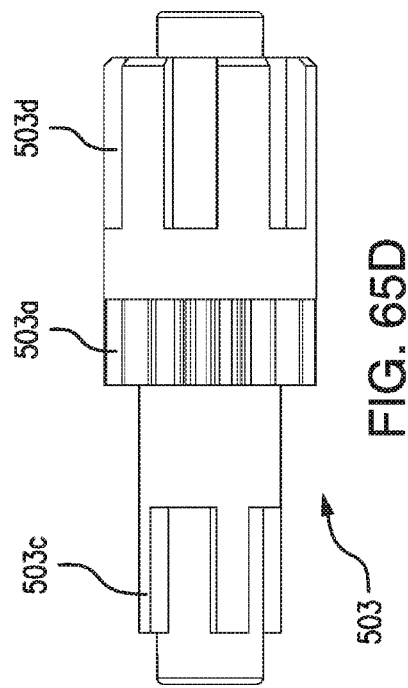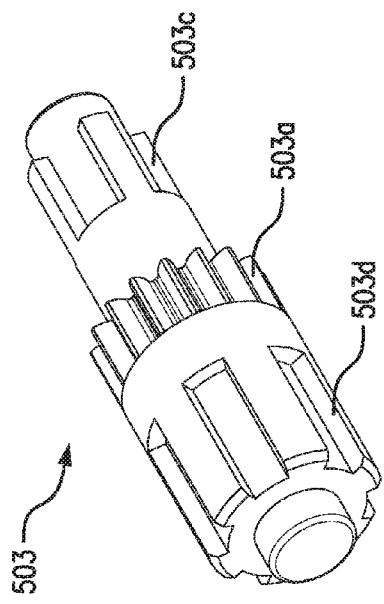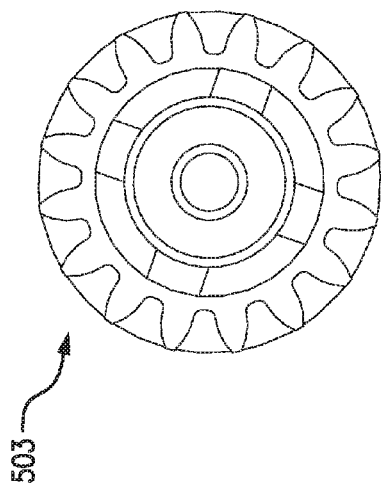

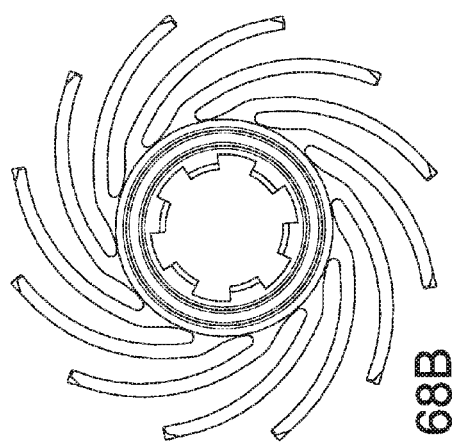
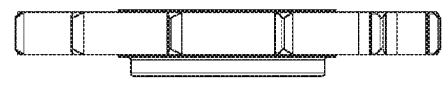
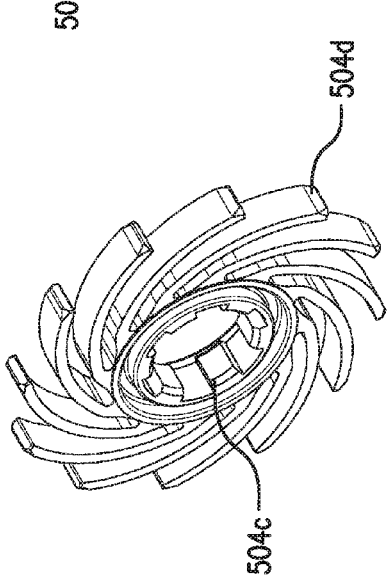
FIG. 68B
FIG. 68D
FIG. 68A
FIG. 68C

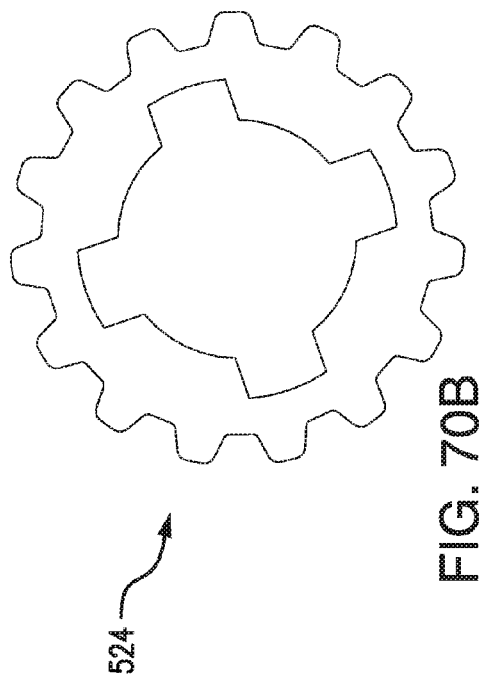
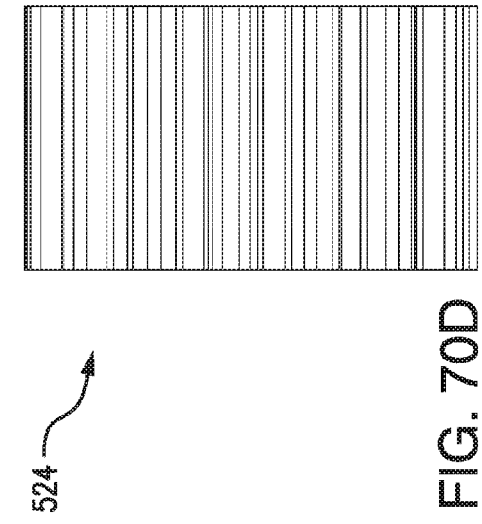
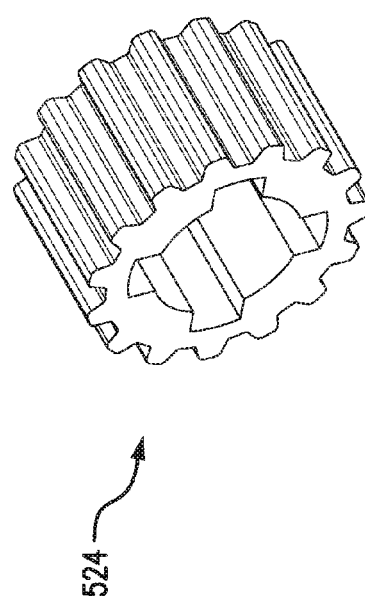
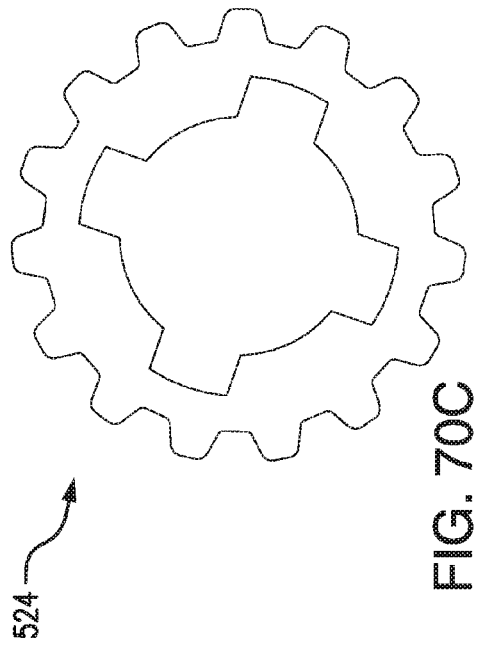
FIG. 70A
FIG. 70B
FIG. 70C
FIG. 70D

METHODS AND SYSTEMS FOR DELIVERING AN IMPLANT USING A PLANETARY GEAR ACTUATION ASSEMBLY

CROSS REFERENCE TO RELATED APPLICATIONS

The present application claims priority to U.S. Provisional Application No. 62/075,059, filed on Nov. 4, 2014, the entire contents of which is incorporated herein by reference.

BACKGROUND

Field of Disclosed Subject Matter

The disclosed subject matter is directed to systems and methods for delivering one or more medical devices, for example an implant, and more specifically, a braided implant. The braided implant, for example a stent or scaffold, can be disposed within a delivery system having an actuation assembly configured to deliver the braided implant using a reciprocating motion.

Description of Related Art

Conventional self-expanding stent delivery systems can include a handle housing portion and an elongated shaft, wherein the stent is disposed within a delivery portion at the distal end of the shaft. To deploy the stent, an outer sheath is retracted relative to the stent, whereby the stent is released from its delivery configuration. In certain systems, an inner member having a pushing mechanism disposed proximate to its distal end can be used push the stent from the outer sheath, while the outer sheath is retracted.

However, there remains a need for a system and method for more accurately delivering an implant using a relatively simple motion and ease of use.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to systems and methods for delivering an implant. For example, an implant can be disposed within a distal end portion of an outer tubular member of the system and positioned to be engaged by a distal end portion of an inner shaft member of the system when the inner shaft member is moved distally relative to the outer tubular member. The inner shaft member can be disposed within the outer tubular member and movable distally and proximally relative to the outer tubular member. The system for delivering an implant can include a handle, a trigger, operatively coupled to the handle, and an actuation assembly operatively coupled to the trigger, the inner shaft member, and the outer tubular member.

The actuation assembly as disclosed herein is a planetary gear type assembly. Particularly, the actuation assembly can include a planet carrier, at least one planet gear operatively coupled to the planet carrier, a sun gear shaft operatively engaged with the planet gear, a ring gear operatively engaged with the planet gear, a first clutch driver configured to limit the sun gear shaft to uni-directional rotational motion, and a second clutch driver configured to uni-directionally lock the sun gear shaft and the planet carrier. The actuation assembly disclosed herein is configured to displace the outer tubular member in the proximal direction a distance (d) relative to the handle and to separately move the inner shaft member distally a distance (x) relative to the handle upon deployment of the trigger from a first position to a second position, and further the actuation assembly is configured to move the inner shaft member proximally a distance (y) relative to the handle with no displacement of the outer tubular member relative to the handle upon return of the trigger from the second position to the first position.

The second clutch driver can be configured to uni-directionally lock the sun gear shaft and the planet carrier such that the sun gear shaft, planet carrier and the ring gear have a 1:1 ratio of rotation during deployment of the trigger from the first position to the second position. The actuation assembly can also include a clutch release operatively coupled to the second clutch driver and configured to prevent the second clutch driver from uni-directionally locking the sun gear shaft and the planet carrier when the clutch release is engaged by a stop. The stop can be disposed on the handle, and the stop can engage the clutch release when the actuation assembly has moved proximally a distance (z) along the handle. For example, the clutch release can include a saw-tooth portion and the stop can include a resilient abutment portion, the resilient abutment portion of the stop can engage the saw-tooth portion of the clutch release when the actuation assembly has moved proximally a distance (z) along the handle.

The first clutch driver can be configured to limit the sun gear shaft to uni-directional motion such that the sun gear shaft does not rotate during return of the trigger from the second position to the first position and the planetary gear rotates about the sun gear shaft. The sun gear shaft can be functionally coupled to the outer tubular member such that upon deployment of the trigger from the first position to the second position the sun gear shaft rotates and thereby causes the outer tubular member to move proximally relative to the handle.

As embodied herein, the actuation assembly can include a shuttle frame having the planet carrier, planet gear, sun gear shaft, ring gear, first clutch driver and second clutch driver disposed thereon. The shuttle frame can be fixedly coupled to the outer tubular member. The sun gear shaft can be functionally coupled to the handle such that upon deployment of the trigger from the first position to the second position the sun gear shaft rotates and the shuttle frame moves proximally a distance relative to the handle. Additionally, the actuation assembly can include an intermediate gear functionally disposed on the shuttle frame between the sun gear shaft and the handle, and operatively engaged with the sun gear shaft.

Furthermore, the actuation assembly can include a ratchet rack fixedly coupled to the inner shaft member and disposed on the shuttle frame. The ratchet rack can be operatively engaged with the planet carrier. The ratchet rack can be operatively engaged with the ring gear.

The actuation assembly can be functionally coupled to the trigger by a driving rack. The driving rack can be operatively engaged with the ring gear and the driving rack can be supported by the handle. The driving rack can be operatively engaged with the planet carrier and the driving rack can be supported by the shuttle frame.

As further embodied herein, the actuation assembly can include at least one pin configured to engage at least one pin track disposed within the handle to thereby guide the shuttle frame along the handle. The at least one pin can include a first pin disposed through an axis of an intermediate gear functionally disposed on the shuttle frame between the sun gear shaft and the handle. The at least one pin can include a second and third pin, each of the second and third pin disposed through the shuttle frame. The at least one pin can include a fourth pin disposed through an axis of the sun gear shaft. The actuation assembly further can include a plate disposed on the shuttle frame.

A sheath gondola can also be provided, disposed between the outer tubular member and the sun gear shaft, wherein the sheath gondola is functionally coupled to the sun gear shaft by a first tension element. The actuation assembly can include a ratchet gondola disposed between the inner tubular member and the ring gear, wherein the ratchet gondola is functionally coupled to the ring gear by a second tension element.

The sun gear shaft can include a sun gear portion, a sheath pinion, and a clutch engagement portion. The planet carrier can include a circumferential pinion, a clutch component, and at least one pin. The ring gear can include a circumferential pinion and a ring gear portion. The first clutch driver and the second clutch driver can each include a sun gear shaft engagement portion and a clutch portion.

As further disclosed herein, a system for delivering an implant is provided. The system can include a handle, as well as a trigger, an outer tubular member, and an inner shaft member, each operatively coupled to the handle. An implant can be provided with the system as a kit or separately. The trigger can be movable between a first position and a second position. The handle can further have an actuation assembly operatively coupled to the trigger. The outer tubular member can include a proximal end portion and a distal end portion, wherein the outer member is operatively coupled to the actuation assembly and movable in a proximal direction relative to the handle. The inner shaft member can include a proximal end portion and a distal end portion. The inner shaft member is disposed within the outer tubular member and operatively coupled to the actuation assembly. The inner shaft member can be movable distally and proximally relative to the outer tubular member. The implant can be disposed within the distal end portion of the outer tubular member and positioned to be engaged by the distal end portion of the inner shaft member when the inner shaft member is moved distally relative to the outer tubular member. The actuation assembly disclosed herein is configured to displace the outer tubular member in the proximal direction a distance (d) relative to the handle and to separately move the inner shaft member distally a distance (x) relative to the handle upon deployment of the trigger from the first position to the second position, and further wherein the actuation assembly is configured to move the inner shaft member proximally a distance (y) relative to the handle with no displacement of the outer tubular member relative to the handle upon return of the trigger from the second position to the first position.

The distance (y) minus the distance (x) can substantially equal the distance (d). Upon deployment of the trigger from the first position to the second position and return of the trigger from the second position to the first position, a net displacement of the inner shaft member relative to the outer tubular member can be zero. The braided implant can have a length, the length of the braided implant can be less than the distance (x). Repeatedly deploying the trigger from the first position to the second position and returning the trigger from the second position to the first position can cause the inner shaft member to urge the braided implant from the outer tubular member. The actuation assembly can be configured to displace the outer tubular member a distance (d) in the proximal direction relative to the handle upon deployment of the trigger from the first position to the second position. The handle can be configured to fit within a hand of a user and upon repeated deployment of the trigger from the first position to the second position and return of the trigger from the second position to the first position the actuation assembly can be configured to move from a position within the handle distal of the user's hand to a position within the handle proximal of the user's hand. The actuation assembly can include a planetary gear system.

According to another embodiment of the disclosed subject matter, a system for delivering an implant is provided. The system can include a handle, a trigger operatively coupled to the handle, and an actuation means configured to displace the outer tubular member in the proximal direction a distance (d) relative to the handle and to separately move the inner shaft member distally a distance (x) relative to the handle upon deployment of the trigger from a first position to a second position, and further wherein the actuation assembly is configured to move the inner shaft member proximally a distance (y) relative to the handle with no displacement of the outer tubular member relative to the handle upon return of the trigger from the second position to the first position.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the disclosed subject matter. Together with the description, the drawings serve to explain the principles of the disclosed subject matter.

BRIEF DESCRIPTION OF THE FIGURES

FIGS. 6A-6D provide perspective FIG. 6A, right FIG. 6B, left FIG. 6C, and front FIG. 6D views of the planet carrier of the delivery system of FIG. 1.

FIGS. 7A-7D provide perspective FIG. 7A, right FIG. 7B, left FIG. 7C, and front FIG. 7D views of the ring gear of the delivery system of FIG. 1.

FIGS. 9A-9D provide perspective FIG. 9A, right FIG. 9B, left FIG. 9C, and front FIG. 9D views of the shuttle frame of the delivery system of FIG. 1.

FIGS. 14A-14D are various views depicting the relationship between the ring gear and the planet gears of the delivery system of FIG. 1.

FIGS. 27A-27D provide perspective FIG. 27A, right FIG. 27B, left FIG. 27C, and front FIG. 27D views of the sun gear shaft of the delivery system of FIG. 24.

FIGS. 31A-31D provide perspective FIG. 31A, right FIG. 31B, left FIG. 31C, and front FIG. 31D views of the shuttle frame of the delivery system of FIG. 24.

FIGS. 32A-32D provide perspective FIG. 32A, right FIG. 32B, left FIG. 32C, and front FIG. 32D views of the intermediate gear of the delivery system of FIG. 24.

FIGS. 34A-34C are various views showing the relationship between the shuttle frame, driving rack, and ring gear of the delivery system of FIG. 24.

FIG. 35 is a perspective view showing the relationship between the planet carrier and the ratchet member of the delivery system of FIG. 24.

FIG. 38 is a left side view, with a portion of the handle housing removed, of the delivery system of FIG. 36.

FIGS. 42A-42D provide perspective FIG. 42A, right FIG. 42B, left FIG. 42C, and front FIG. 42D views of the first clutch driver of the delivery system of FIG. 36.

FIGS. 45A-45D provide perspective FIG. 45A, right FIG. 45B, left FIG. 45C, and front FIG. 45D views of the clutch release of the delivery system of FIG. 36.

FIG. 46 is an exploded view of a further exemplary embodiments of a delivery system in accordance with the disclosed subject matter.

FIGS. 47A-47D provide perspective FIG. 47A, right FIG. 47B, left FIG. 47C, and front FIG. 47 D views of the sun gear shaft of the delivery system of FIG. 46.

FIGS. 51A-51D provide perspective FIG. 51A, right FIG. 51B, left FIG. 51C, and front FIG. 51D views of the shuttle frame of the delivery system of FIG. 46.

FIG. 52 is a perspective view of another exemplary embodiment of a delivery system in accordance with the disclosed subject matter.

FIG. 54 is a left side view, with a portion of the handle housing removed, of the delivery system of FIG. 52.

FIGS. 56A-56D provide perspective FIG. 56A, right FIG. 5613, left FIG. 56C, and front FIG. 56D views of the planet carrier of the delivery system of FIG. 52.

FIGS. 59A-59D provide perspective FIG. 59A, right FIG. 5913, left FIG. 59C, and front FIG. 59D views of the shuttle frame of the delivery system of FIG. 52.

FIGS. 61A-61D provide perspective FIG. 61A, right FIG. 61B, left FIG. 61C, and front FIG. 61D views of the clutch release of the delivery system of FIG. 52.

FIGS. 65A-65D provide perspective FIG. 65A, right FIG. 65B, left FIG. 65C, and front FIG. 65D views of the sun gear shaft of the delivery system of FIG. 62.

FIGS. 68A-68D provide perspective FIG. 68A, right FIG. 68B, left FIG. 68C, and front FIG. 68D views of the first clutch driver of the delivery system of FIG. 62.

FIGS. 70A-70D provide perspective FIG. 70A, right FIG. 70B, left FIG. 70C, and front FIG. 70D views of the ratchet gear of the delivery system of FIG. 62.

DETAILED DESCRIPTION

Figure 1:
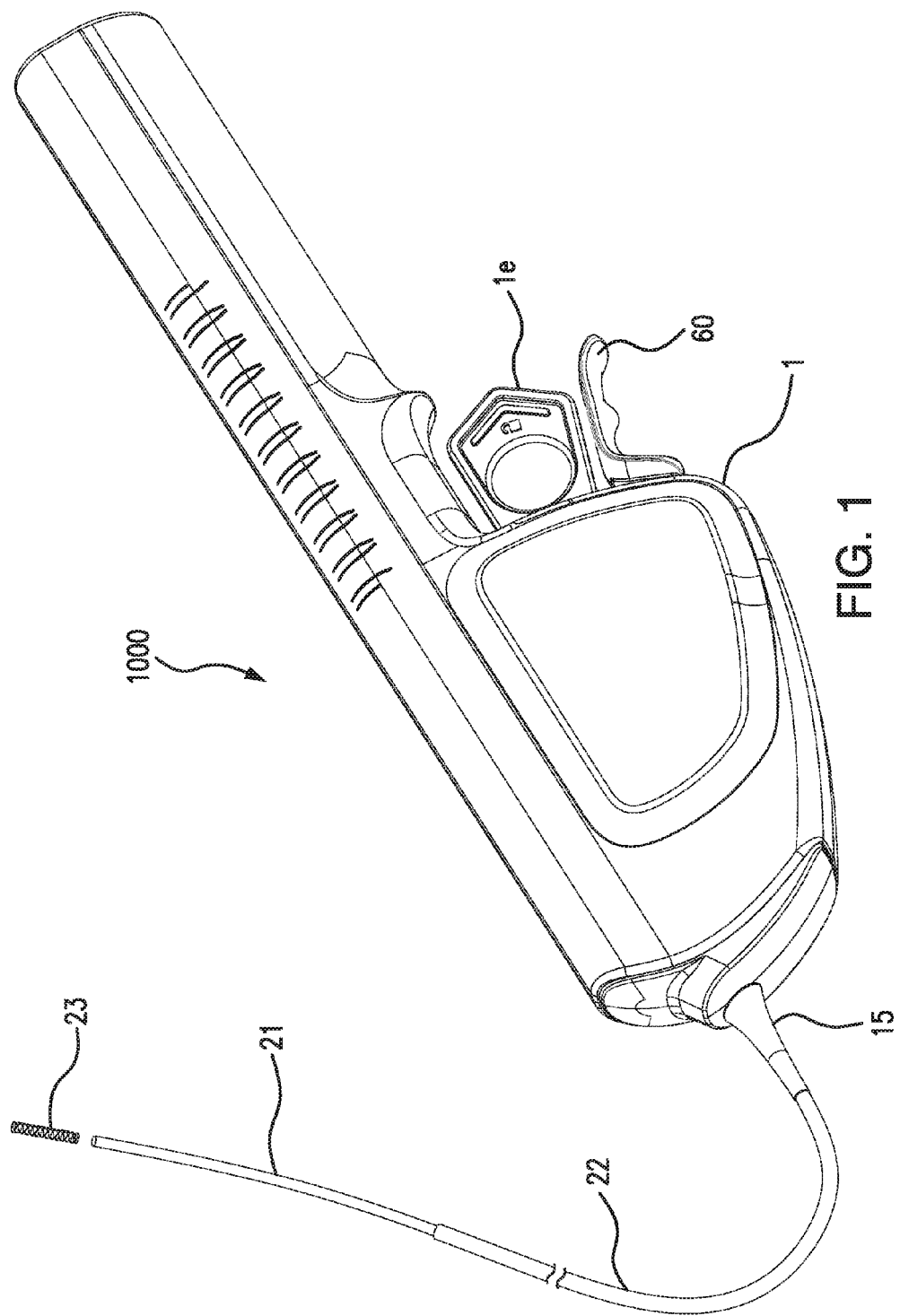
FIG. 1 is a perspective view of an exemplary embodiment of a delivery system in accordance with the disclosed subject matter.

Reference will now be made in detail to the various exemplary embodiments of the disclosed subject matter, exemplary embodiments of which are illustrated in the accompanying drawings. The structure and corresponding method of making and using the disclosed subject matter will be described in conjunction with the detailed description of the delivery system. The methods and systems described herein can be used for delivering a medical device, such as a stent, scaffold, stent graft, valve, filter, or other suitable implant to a desired location in a patient.

Generally, and as set forth in greater detail, the disclosed subject matter provided herein includes a delivery system having a handle, a trigger, and an actuation assembly. The trigger is operatively coupled to the handle. The actuation assembly is operatively coupled to the trigger, the inner shaft member, and the outer tubular member. As used herein the terms "functionally" and "operatively" as used with "coupled," "engaged," or "connected," are interchangeable and understood by one of skill in the art. The actuation assembly includes a planet carrier, at least one planet gear operatively coupled to the planet carrier, a sun gear shaft operatively engaged with the planet gear, a ring gear operatively engaged with the planet gear, a first clutch driver configured to limit the sun gear shaft to unidirectional rotational motion, and a second clutch driver configured to uni-directionally lock the sun gear shaft and the planet carrier. The actuation assembly is configured to displace the outer tubular member in the proximal direction a distance (d) relative to the handle and to separately move the inner shaft member distally a distance (x) relative to the handle upon deployment of the trigger from a first position to a second position, and further wherein the actuation assembly is configured to move the inner shaft member proximally a distance (y) relative to the handle with no displacement of the outer tubular member relative to the handle upon return of the trigger from the second position to the first position.

A variety of types of medical devices are suitable for delivery by the delivery system of the present invention. For purpose of illustration and not limitation, the delivery system is described herein with a medical device depicted as a self-expanding stent. Particularly, although not by limitation, reference is made herein to the implant being a braided stent or scaffold for purpose of illustration only. However, the delivery system presently disclosed is not limited to the delivery of self-expanding stents. Other devices can also be used. For example, scaffolds, coils, filters, stent grafts, embolic protection devices, and artificial valves can be delivered within a patient's vasculature, heart, or other organs and body lumens using the disclosed delivery system. Other devices such as a prosthesis retrieval mechanism can also be delivered with the delivery system to a predetermined location in a patient's luminal system. Moreover, a combination of medical devices and/or beneficial agents can also be delivered using the disclosed subject matter. For example, multiple stents and/or a combination of stents and embolic protection devices and/or beneficial agents can be delivered by the disclosed subject matter, as described below. Additional information related to delivery of implants can be found in U.S. application Ser. No. 11/876, 764, filed on Oct. 22, 2007, and U.S. application Ser. No. 13/118,325, filed on May 27, 2011, each of which is incorporated by reference in its entirety herein.

Figure 3:
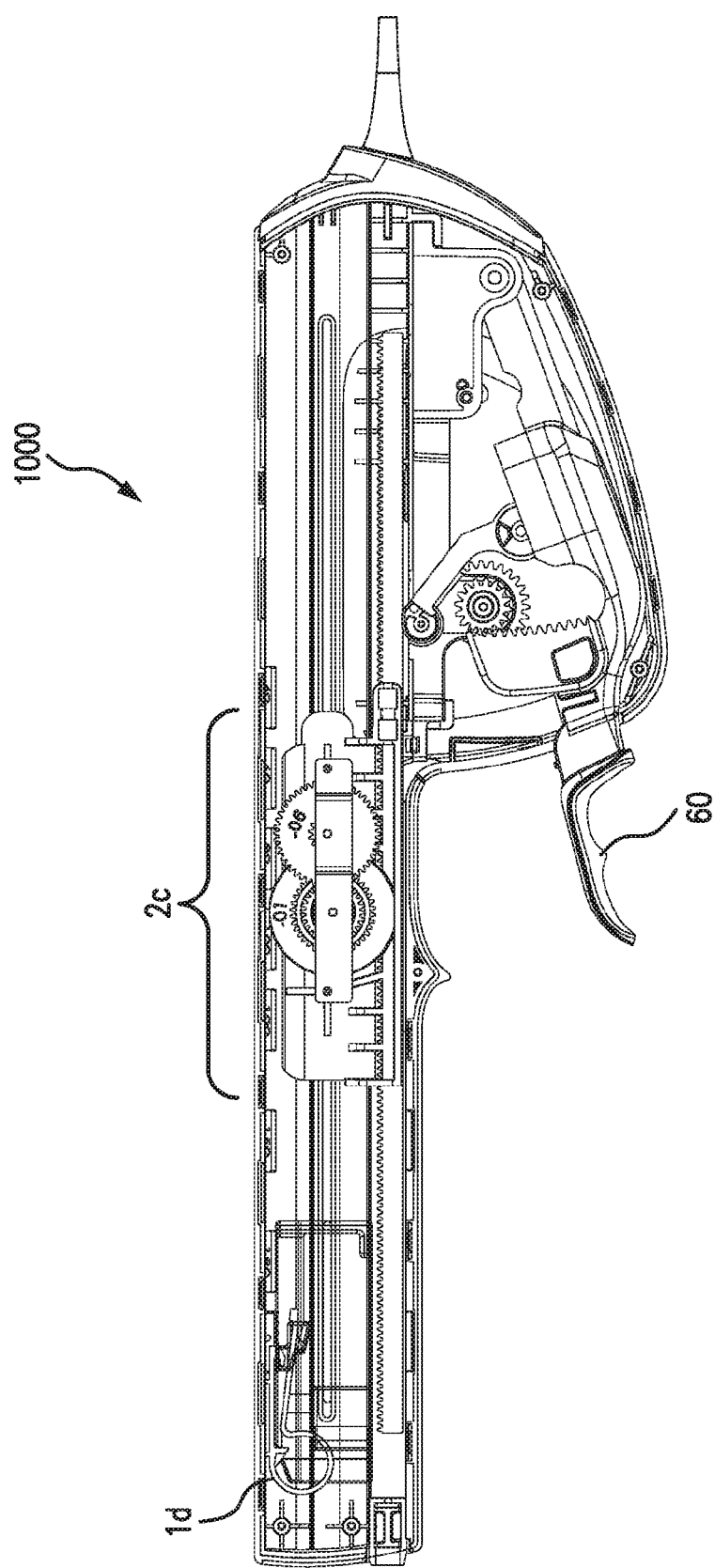
FIG. 3 is a left side view, with a portion of the handle housing removed, of the delivery system of FIG. 1.

Referring to FIG. 1 for the purpose of illustration and not limitation, various embodiments of the delivery systems disclosed herein generally can include a handle 1, an outer tubular member 22, and an inner shaft member 21. An implant 23, for example, a braided implant can be provided with the system or independently. The handle can include a trigger assembly including a trigger 60 movable between and first position and a second position, and an actuation assembly 2 (see e.g., FIG. 3) operatively coupled to the trigger 60. The outer tubular member 22 can include a proximal end portion and a distal end portion. The outer tubular member 22 can be operatively coupled to the actuation assembly 2 and can be movable in a proximal direction relative to the handle 1. A stabilizer tube (not shown) can be disposed over at least the proximal end portion of the outer tubular member 22, and a strain relief 15 can be used to couple the stabilizer tube and the handle 1. The inner shaft member 21 can include a proximal end portion and a distal end portion. The inner shaft member 21 can be disposed within the outer tubular member 22 and can be operatively coupled to the actuation assembly 2. The inner shaft member 21 of the disclosed delivery system is movable distally and proximally relative to the outer tubular member 22. The implant 23 can be disposed within the distal end portion of the outer tubular member 22 and can be positioned to be engaged by the distal end portion of the inner shaft member 21 when the inner shaft member is moved distally relative to the outer tubular member 22. The distal end portion of the inner shaft member 21 can have a pushing mechanism disposed thereon. For example, U.S. application Ser. No. 13/118,325, filed on May 27, 2011, which is incorporated by reference in its entirety herein, discloses suitable pusher elements for the delivery system. The outer tubular member 22 is depicted with a break in FIG. 1 to indicate that the length shown is only exemplary and the outer tubular member 22 and inner shaft member 21 can be longer than shown. Indeed, any suitable length can be used. As an example and not by way of limitation, the outer tubular member 22 and inner shaft member 21 can be long enough to extend from outside the body of a patient through a tortuous path to a treatment location within the body of a patient. The handle 1 can further include a luer lock at the proximal end of the handle to receive a guidewire therethrough which can extend through the inner shaft member and/or a flushing device as desired.

The actuation assembly 2 of the disclosed subject matter is configured to displace the outer tubular member 22 in the proximal direction a distance (d) relative to the handle 1 and to separately move the inner shaft member 21 distally a distance (x) relative to the handle 1 upon deployment of the trigger 60 from the first position to the second position. Furthermore, the actuation assembly 2 is configured to move the inner shaft member 21 proximally a distance (y) relative to the handle 1 with no displacement of the outer tubular member 22 relative to the handle 1 upon return of the trigger 60 from the second position to the first position. Put another way, the actuation assembly 2 can be configured to move the outer tubular member 22 in a proximal direction relative to the handle 1 and to separately move the inner shaft member 21 distally relative to the outer tubular member 22 upon deployment of the trigger 60 form the first position to the second position. The actuation assembly 2 can further be configured to move the inner shaft member 21 proximally relative to the outer tubular member 22 with no displacement of the outer tubular member 22 relative to the handle 1 upon return of the trigger 60 from the second position to the first position. Repeatedly deploying the trigger 60 from the first position to the second position and returning the trigger from the second position to the first position can cause the inner shaft member 21 to urge the implant 23 from the outer tubular member 22.

The distance (y) minus the distance (x) can be substantially equal to the distance (d). Upon deployment of the trigger 60 from the first position to the second position and return of the trigger 60 from the second position to the first position a net displacement of the inner shaft member 21 relative to the outer tubular member 22 thus can be zero. The implant 23 can have a length, and the length of the implant 23 can be less than the distance (x). Example lengths of the implant 23, for purpose of illustration and not limitation, can be 20 mm, 30 mm, 40 mm, 60 mm, 80 mm, 100 mm, 120 mm, and 150 mm.

The distances (d), (x) and (y) can be selected based at least in part on the diameter of the implant to be delivered, the desired compression of the implant to be delivered, the path between the insertion point and the location of implant delivery, and/or other variables. As an example, and not by way of limitation, for a stent having a diameter of 4.5 mm when delivered to the vasculature, (d) can be about 12 mm, (x) can be about 28 mm, and (y) can be about 40 mm. As another example and not by way of limitation, the ratio (referred to herein as the "gear ratio") between the net distal motion of the inner shaft member 21 relative to the outer shaft member 22 (i.e., the distance (d) plus the distance (x)) to the distance (d) can be greater than 3. As an example, the gear ratio of (12+28):(12) is about 3.3. The actuation assembly disclosed herein having such a gear ratio can be used to properly deploy a braided stent from an extended delivery configuration to an expanded deployed configuration and address a 3:1 change in length of the stent from the delivery length to the deployment length. Exemplary diameters for stents when delivered to the vasculature can range from 4 mm to 12 mm or greater, such as, exemplary diameters can be 4.5 mm, 5.0 mm, 5.5 mm, 6.0 mm, 6.5 mm, 7.5 mm, or 8 mm, or suitable increments therebetween.

Figure 2:
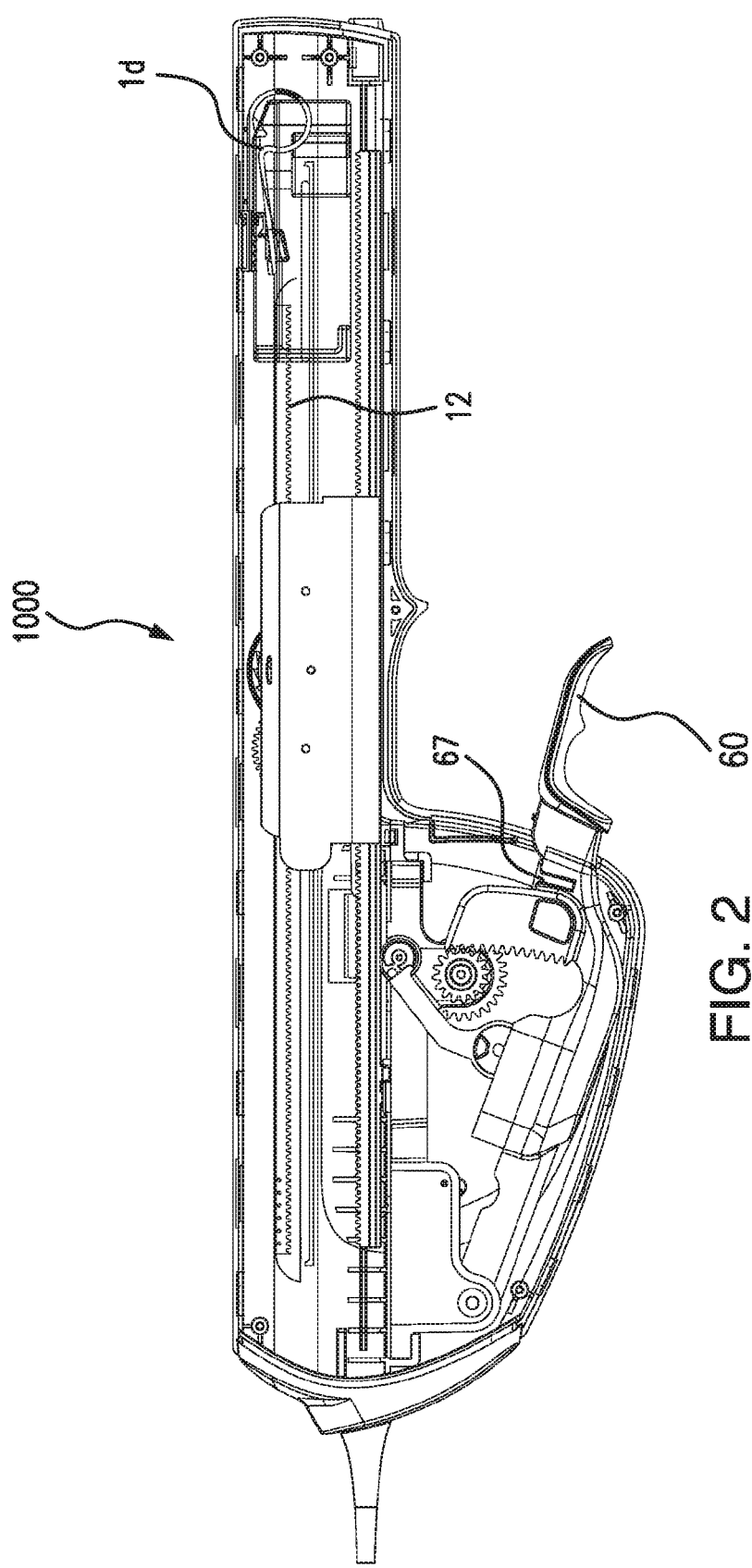
FIG. 2 is a right side view, with a portion of the handle housing removed, of the delivery system of FIG. 1.

For the purpose of illustration, and not limitation, an exemplary embodiment of a system for delivering an implant is shown in FIG. 1 and is designated generally by reference character 1000. Portions of this exemplary embodiment are depicted in FIGS. 2-23. The handle 1 can include a first handle housing portion 1*a* and a second handle housing portion 1*b*. The system can also include a trigger 60. The trigger 60 can be operatively coupled to the handle, such that the trigger 60 can be moveable between a first position and a second position. As embodied herein, the trigger can be biased towards the first or second position, for example, by a spring. A ratchet mechanism 80 can be provided to prevent moving the trigger between the first and second positions, such as to require a full stroke in one or both directions as desired. Additionally, a trigger stop 67 (FIG. 2) can be provided. The trigger stop 67 can be disposed between the trigger 60 and the handle 1, and can limit how far the trigger 60 can be actuated. The size of trigger stop 67 can be selected based at least in part on the diameter of the stent to be delivered, the desired compression of the stent to be delivered, the path between the insertion point and the location of stent delivery, and/or other variables. Indeed, the system can include a trigger lock 1*e*, which can prevent any motion of the trigger. For example, the trigger lock 1*e* can be engaged prior to use (e.g., during shipping) and can be disengaged in anticipation of use of the system.

The system 1000 also includes an actuation assembly 2. The actuation assembly 2 is operatively coupled to the trigger 60, the inner shaft member 21 and the outer tubular member 22 to provide the desired relative movement as set for in detail above.

Figure 4:
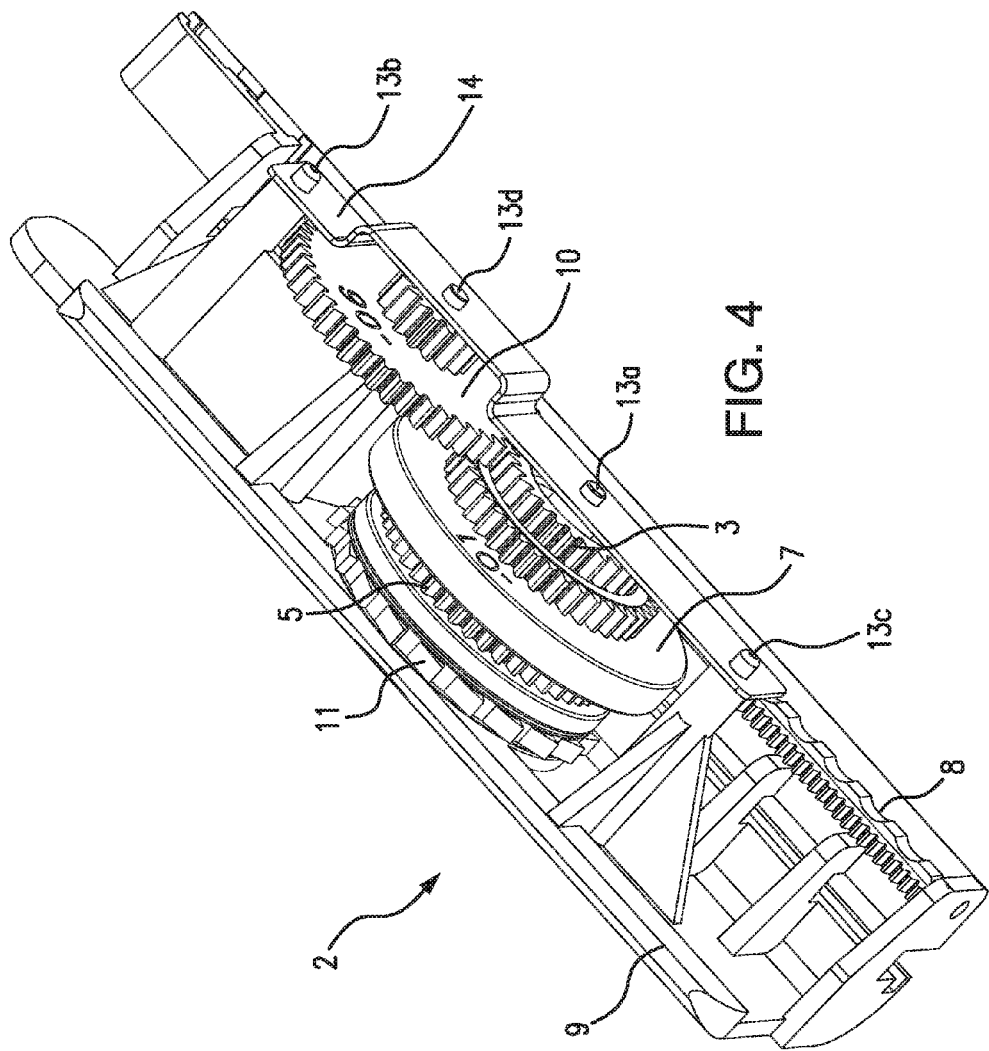
FIG. 4 provides a top perspective view of selected elements of the actuation assembly of the delivery system of FIG. 1.
Figure 5B:
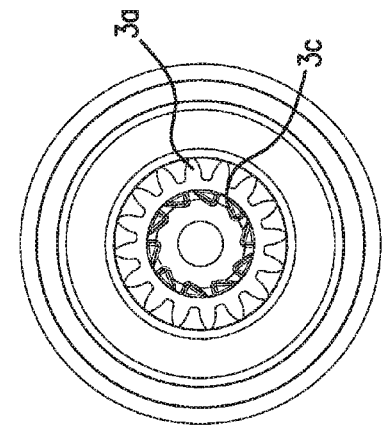
FIGS. 5A-5D provide perspective FIG. 5A, right FIG. 5B, left FIG. 5C, and front FIG. 5D views of the sun gear shaft of the delivery system of FIG. 1.
Figure 5D:
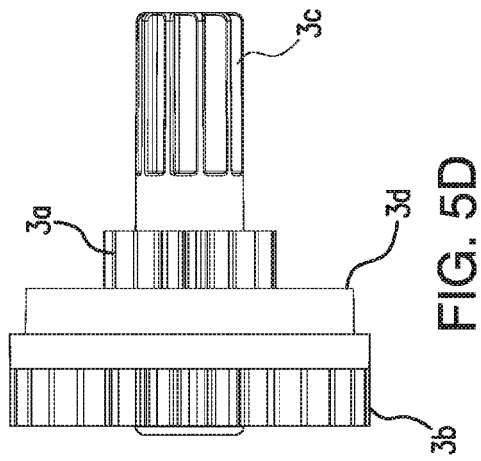
Figure 5A:
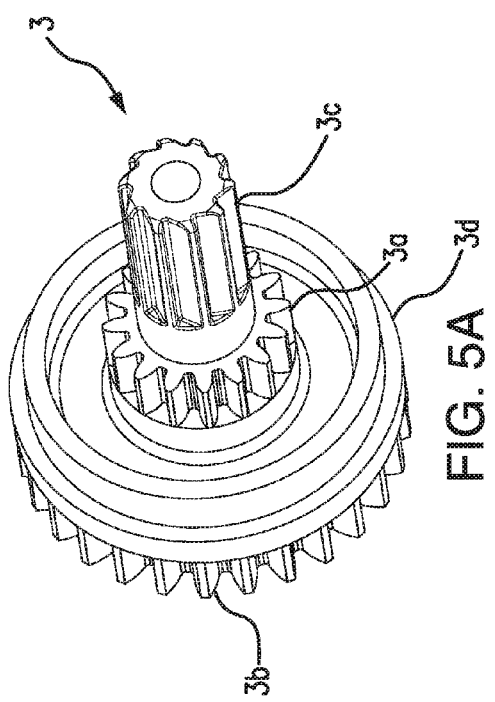
Figure 5C:
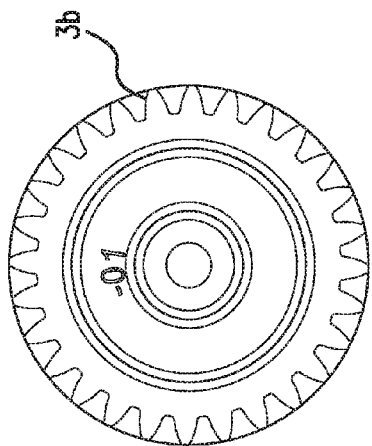
Figure 8A:
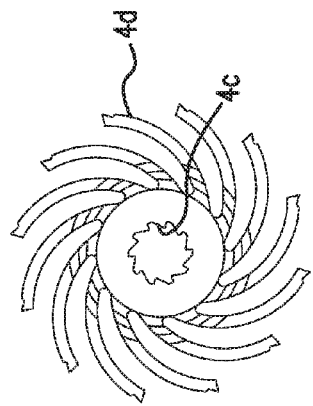
FIGS. 8A-8D provide perspective FIG. 8A, right FIG. 8B, left FIG. 8C, and front FIG. 8D views of the first clutch driver of the delivery system of FIG. 1.
Figure 8B:
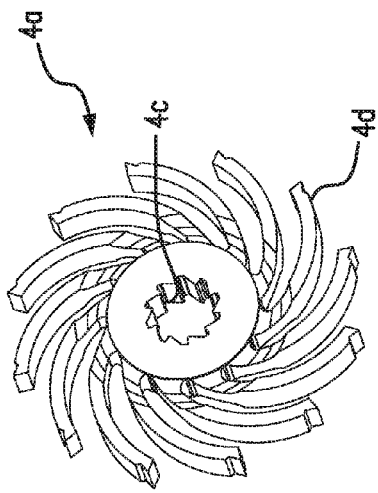
Figure 8C:
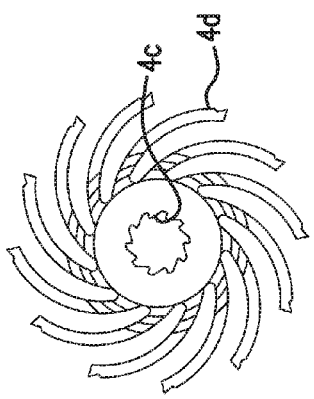
Figure 8D:
Figure 10B:
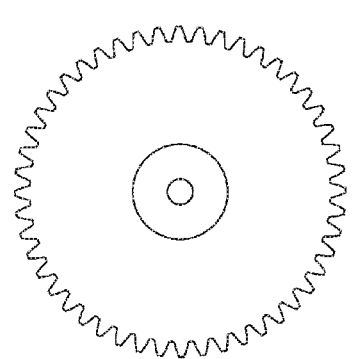
FIGS. 10A-10D provide perspective FIG. 10A, right FIG. 10B, left FIG. 10C, and front FIG. 10D views of the intermediate gear of the delivery system of FIG. 1.
Figure 10D:
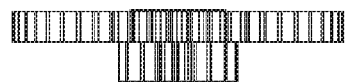
Figure 10A:
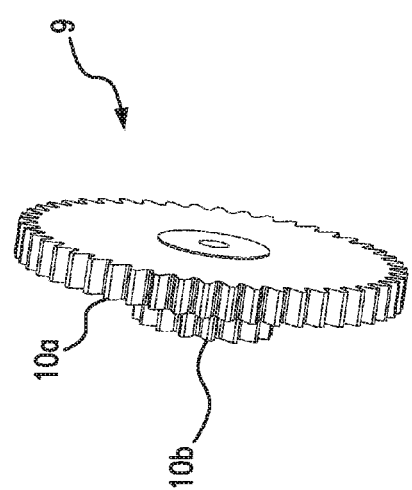
Figure 10C:
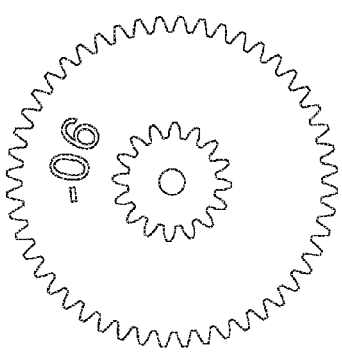
Figure 11B:
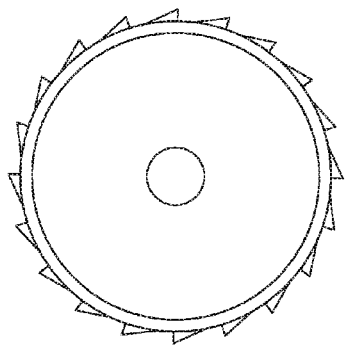
FIGS. 11A-11D provide perspective FIG. 11A, right FIG. 11B, left FIG. 11C, and front FIG. 11D views of the clutch release of the delivery system of FIG. 1.
Figure 11D:
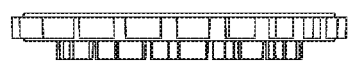
Figure 11A:
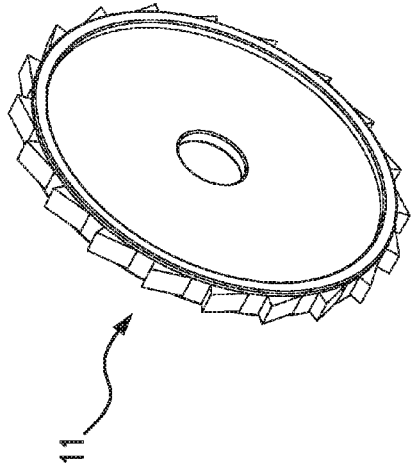
Figure 11C:
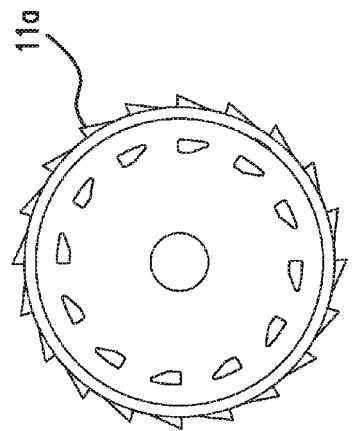

FIG. 4 shows for the purpose of illustration and not limitation, selected elements or components of the actuation assembly of the delivery system 1000. That is, FIGS. 5-11 show for the purpose of illustration and not limitation, selected components of an actuation assembly 2. FIGS. 12-23 show for the purpose of illustration and not limitation, the relationship between selected components of an actuation assembly 2. As noted above, the actuation assembly 2 can be configured to displace the outer tubular member 22 in the proximal direction a distance (d) relative to the handle 1 and to separately move the inner shaft member 21 distally a distance (x) relative to the handle 1 upon deployment of the trigger 60 from the first position to the second position. The actuation assembly 2 can be configured to move the inner shaft member 21 proximally a distance (y) relative to the handle 1 with no displacement of the outer tubular member 22 relative to the handle 1 upon return of the trigger 60 from the second position to the first position.

As depicted herein, the actuation assembly 2 can include a planetary gear system. For example, the actuation assembly can include a planet carrier 5, at least one planet gear 6, a sun gear shaft 3, a ring gear 7, a first clutch driver 4a and a second clutch driver 4b. The actuation assembly can include a shuttle frame 9. The shuttle frame can have the planet carrier 5, the planet gears 6, the sun gear shaft 3, the ring gear 7, and the first and second clutch drivers 4a, 4b disposed thereon. Shuttle frame 9 can be disposed within the handle 1 and can be moveable relative to the handle 1 along the length of the handle 1.

The sun gear shaft 3 (FIG. 5) can include a sun gear portion 3a, a sheath pinion 3b, a clutch engagement portion 3c, and a step portion 3d. As depicted herein, the clutch engagement portion 3c can be saw-toothed, although other suitable configurations can be used. The planet carrier 5 (FIG. 6) can include a circumferential pinion 5a, a clutch component 5b, and at least one pin 5c. The planet carrier 5 will include one pin 5c for each planet gear 6. For example, as shown at least in FIG. 6, the planet carrier 5 includes three pins 5c. The ring gear 7 (FIG. 7) can include a circumferential pinion 7a and a ring gear portion 7b. Each clutch driver 4a, 4b (FIG. 8) can be identical in shape, and can include a sun gear shaft engagement portion 4c and a clutch portion 4d. The sun gear shaft engagement portion 4c can be saw-toothed, although other suitable configurations can be used.

Figure 12:
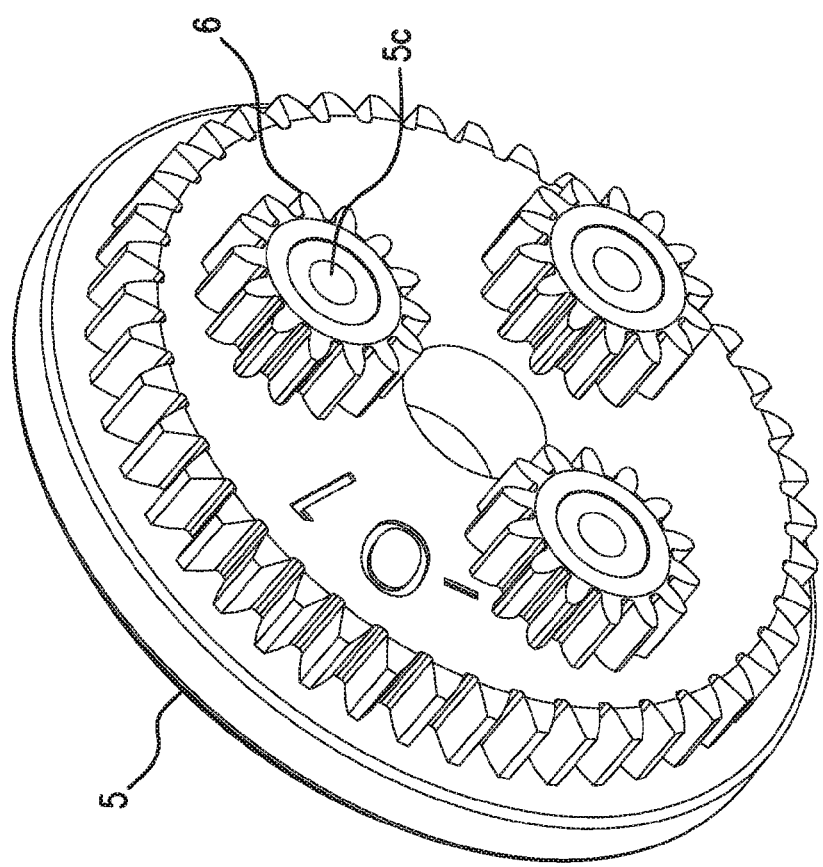
FIG. 12 is a perspective view illustrating the relationship between the planet carrier and the planet gears of the delivery system of FIG. 1.
Figure 13B:
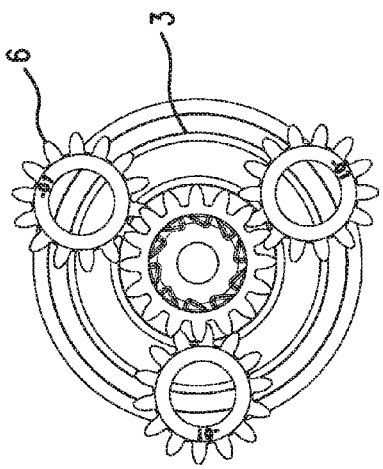
FIGS. 13A-13D are various views depicting the relationship between the sun gear shaft and the planet gears of the delivery system of FIG. 1.
Figure 13D:
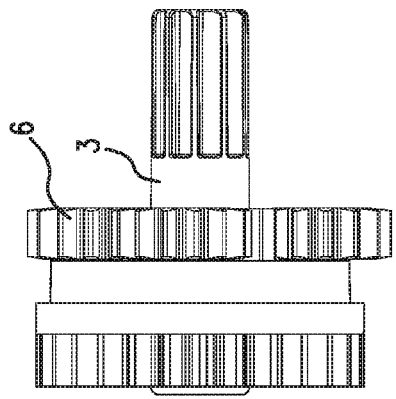
Figure 13A:
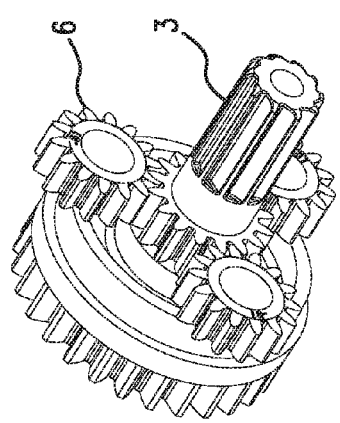
Figure 13C:
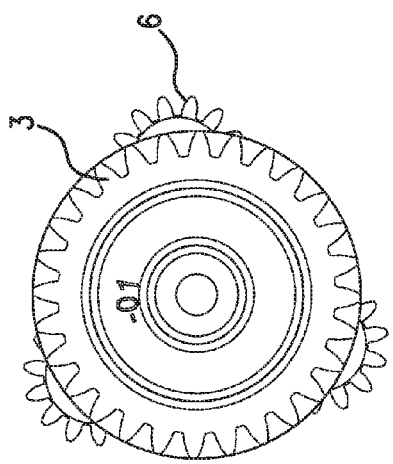
Figure 15B:
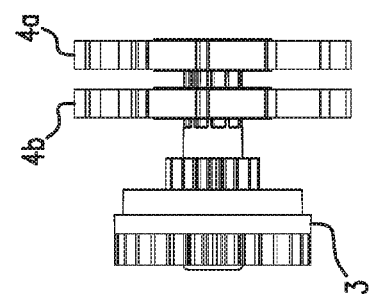
FIGS. 15A-15D are various views depicting relationship between the sun gear shaft and the first and second clutch drivers of the delivery system of FIG. 1.
Figure 15D:
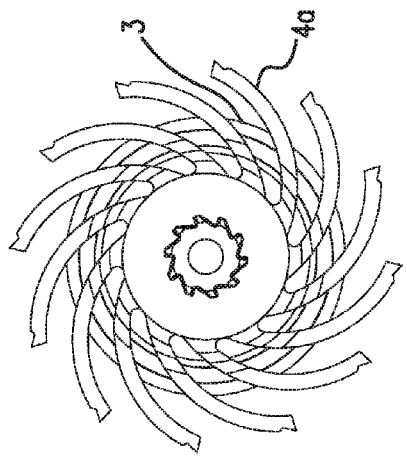
Figure 15A:
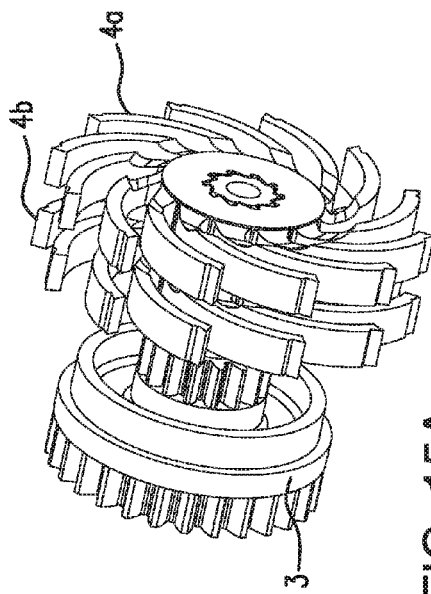
Figure 15C:
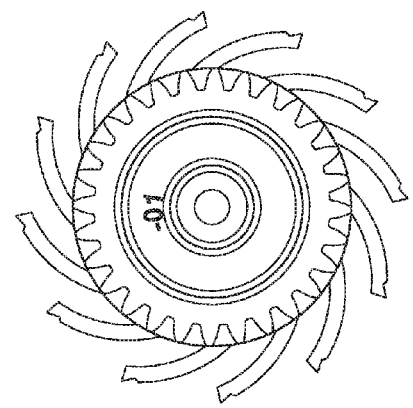

The planet carrier 5 thus operates as the "planet carrier" of the planetary gear system. As such, the at least one planet gear 6 can be operatively coupled to the planet carrier 5. Each planet gear 6 can be operatively coupled to a pin 5c of the planet carrier 5, as shown in FIG. 12 for the purpose of illustration and not limitation. In the exemplary embodiment, the system includes three planet gears 6 operating as the "planet gears" of the planetary gear system; however, one, two four or more planet gears 6 can be provided. The sun gear shaft 3 can operate as the "sun gear" of the planetary system. The sun gear portion 3a of the sun gear 3 can be operatively engaged with the planet gears 6 such that the planet gears 6 are operatively meshed with the sun gear portion 3a, as shown in FIG. 13 for the purpose of illustration and not limitation. The ring gear 7 can operate as the "ring gear" of the planetary system. The ring gear portion 7b can be operatively engaged with the planet gears 6 such that the planet gears 6 are operatively meshed with the ring gear portion 7b of the ring gear 7, as shown in FIG. 14 for the purpose of illustration and not limitation. The step portion 3d of the sun gear shaft 3 can be configured to maintain the position of the remaining portion the planetary gear system. For example, the step portion 3d can engage the ring gear 7 and reduce undesired movement of the ring gear 7, which can reduce undesired movement of the planet gears 6.

As further depicted, the shuttle frame 9 (FIG. 9) can include a clutch engagement portion 9a, a cavity 9b which can be configured to receive a ferrule coupled to the proximal end of the outer tubular member 22, and a guide 9c.

Figure 16:
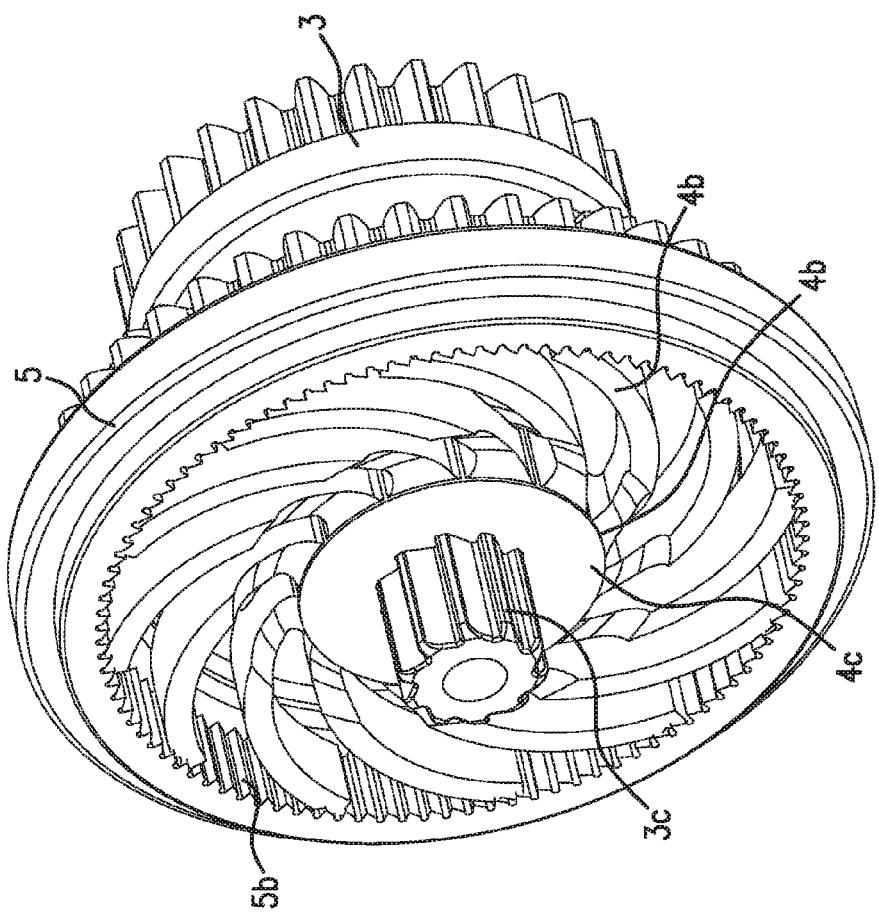
FIG. 16 is a perspective view illustrating the relationship between the sun gear shaft, the planet carrier, and the second clutch driver of the delivery system of FIG. 1.

The second clutch driver 4b can be configured to uni-directionally lock the sun gear shaft 3 and the planet carrier 5. As such, the sun gear shaft 3, planet carrier 5, and ring gear 7 have a 1:1 ratio of rotation during deployment of the trigger 60 from the first position to the second position. For example, the sun gear engagement portion 4c of the second clutch driver 4b can engage the clutch engagement portion 3c of the sun gear shaft 3, such that the sun gear shaft 3 and the second clutch driver 4b rotate together, as shown in FIG. 15, for the purpose of illustration and not limitation. Additionally, the clutch portion 4d of the second clutch driver 4b can have a ratchet-like engagement with the clutch component 5b of the planet carrier 5, as shown in FIG. 16, for the purpose of illustration and not limitation. Such a configuration can allow the sun gear shaft 3 and planet carrier 5 to rotate independently of one another in a first direction (e.g., when the planet carrier 5 rotates in the counter clockwise direction in FIG. 16), and locked together in a second direction (e.g., when the planet carrier 5 rotates in the clockwise direction in FIG. 16).

Figure 17:
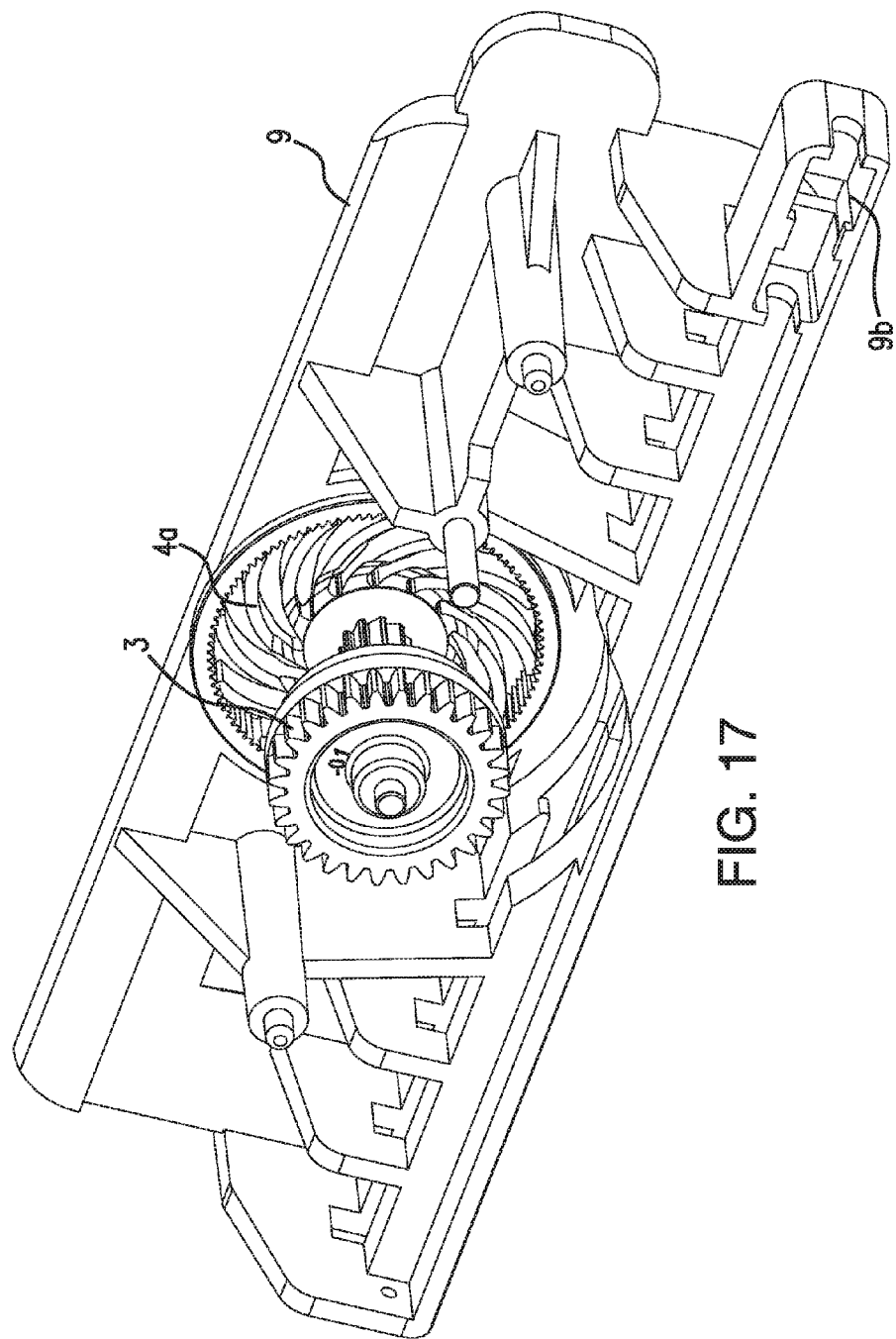
FIG. 17 is a perspective view illustrating the relationship between the sun gear shaft, the first clutch driver, and the shuttle frame of the delivery system of FIG. 1.

The first clutch driver 4a can be configured to limit the sun gear shaft 3 to uni-direction rotational motion. The first clutch driver 4a and sun gear shaft 3 can be configured such that the sun gear shaft 3 does not rotate during return of the trigger from the second position to the first position. For example, the sun gear engagement portion 4c of the first clutch driver 4a can be fixedly engaged with the clutch engagement portion 3c of the sun gear shaft 3, such that the sun gear shaft 3 and the first clutch driver 4a rotate together, as shown in FIG. 15, for the purpose of illustration and not limitation. Additionally, the first clutch driver 4a can have a ratchet-type engagement with a separate element, for example and as shown in FIG. 17 for the purpose of illustration and not limitation, a clutch engagement portion 9a on the shuttle frame 9. As such, the first clutch driver 4a can be limited to uni-direction motion by the clutch engagement portion 9a, and thereby limit the sun gear shaft 3 to uni-directional motion (e.g., the sun gear shaft 3 can only rotate in the counterclockwise direct in FIG. 17).

Figure 18:
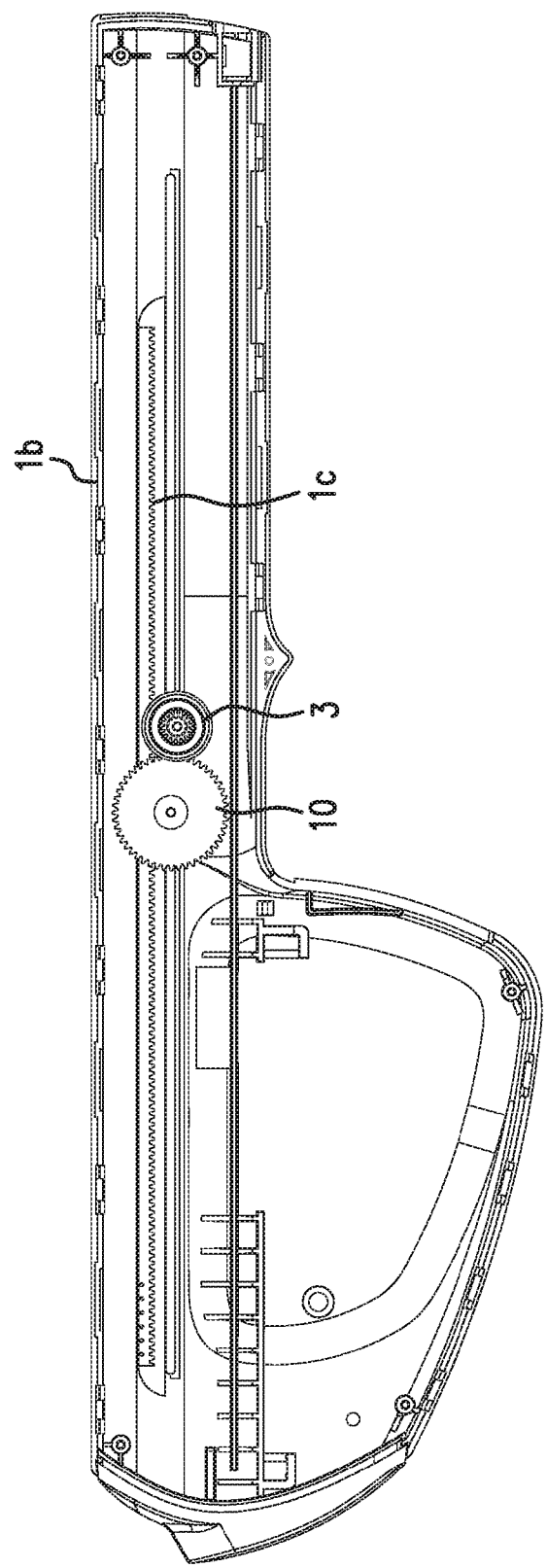
FIG. 18 is a side view illustrating the relationship between the sun gear shaft, intermediate gear, and handle of the delivery system of FIG. 1.

The sun gear shaft 3 can be functionally coupled to the outer tubular member 22 such that upon deployment of the trigger from the first position to the second position, the sun gear shaft 3 rotates and thereby causes the outer tubular member 22 to move proximally. For example, the shuttle frame 9 can be fixedly coupled to the outer tubular member 22 at the cavity 9b. As depicted herein for illustration, the shuttle frame 9 and outer tubular member 22 can be coupled by a ferrule. The sheath pinion portion 3b of the sun gear shaft 3 can be functionally coupled to the handle 1 such that upon deployment of the trigger 60 from the first position to the second position the sun gear shaft 3 rotates, engages the handle 1, and moves the shuttle frame 9 proximally a distance relative to the handle 1. As such and as embodied herein the outer tubular member 22 also moves proximally relative to the handle 1 because it is fixedly coupled to the shuttle frame 9. Additionally, intermediate gear 10 can be functionally meshed between the sheath pinion portion 3b and a sheath rack 1c disposed on the handle 1, as shown in FIG. 18, for the purpose of illustration and not limitation. Additionally or alternatively, the sheath pinion portion 3b can directly mesh the sheath rack 1c. As noted herein above, the first clutch driver 4b can prevent the sun gear shaft 3 from rotating during return of the trigger 60 from the second position to the first position. Accordingly, the shuttle frame 9, the outer tubular member 22 fixedly coupled thereto, and all other components carried by the shuttle frame 9, will move proximally when the trigger 60 is deployed from the first position to the second position, but remain stationary when the trigger 60 is returned from the second position to the first position as embodied herein. The gears of the small spur gear 10b of the intermediate gear 10 (or the gears of the sheath pinion portion 3b) and the gears of the sheath rack 1c can utilize a non-standard pitch as desired or needed. As an example and not by way of limitation, a standard 48 pitch can be slightly enlarged. Such a change can allow the actuation assembly to achieve the desired value of (d) when the trigger 60 is deployed from the first position to the second position.

Figure 19:
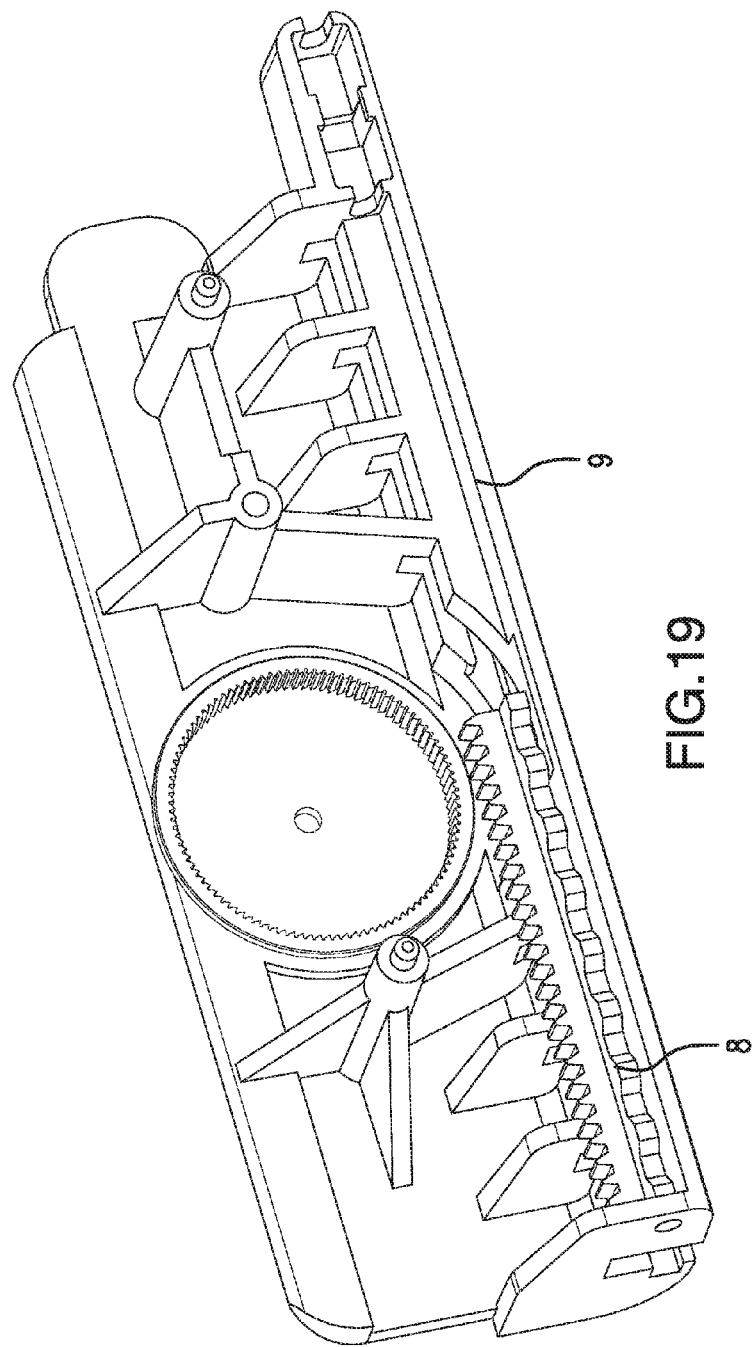
FIG. 19 is a perspective view illustrating the relationship between the shuttle frame and the ratchet member of the delivery system of FIG. 1.
Figure 20:
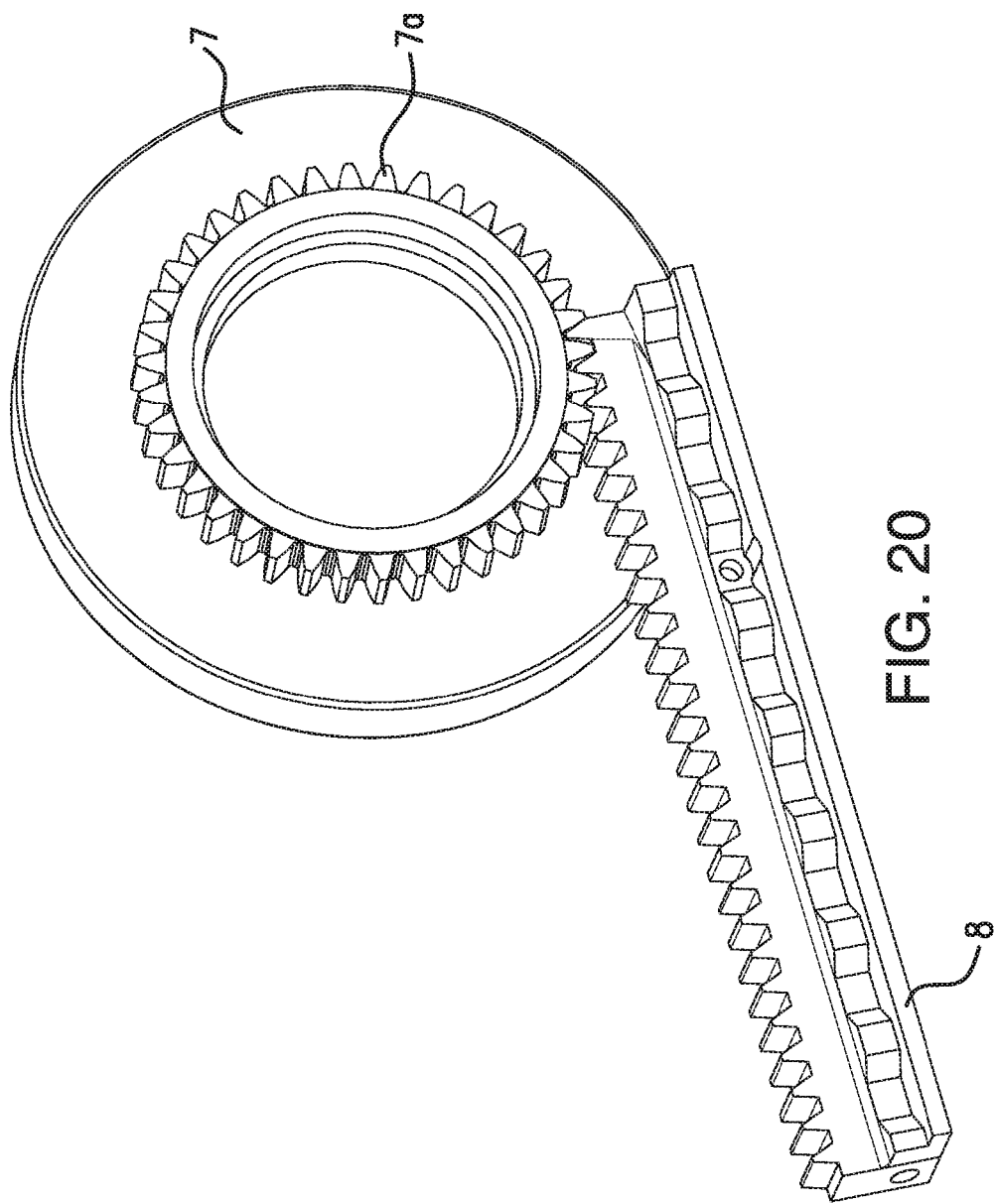
FIG. 20 is a perspective view illustrating the relationship between the ring gear and the ratchet member of the delivery system of FIG. 1.

The actuation assembly 2 can also include a ratchet rack 8. The ratchet rack 8 can be fixedly coupled to the inner shaft member 21 and can be disposed on the shuttle frame 9, as shown in FIG. 19 for the purpose of illustration and not limitation. The ratchet rack 8 can be operatively engaged with the ring gear 7. For example, the ratchet rack 8 can be operatively meshed with the circumferential pinion 7a of the ring gear 7, as shown in FIG. 20, for the purpose of illustration and not limitation. Upon deployment of the trigger 60 from the first position to the second position, the ring gear 7 can rotate and cause the ratchet rack 8, and therefore the inner shaft member 21, to move distally relative to the handle. Upon return of the trigger 60 from the second position to the first position, the ring gear 7 can rotate in the opposite direction and cause the ratchet rack 8, and therefore the inner shaft member 21, to move proximally relative to the handle.

Figure 21:
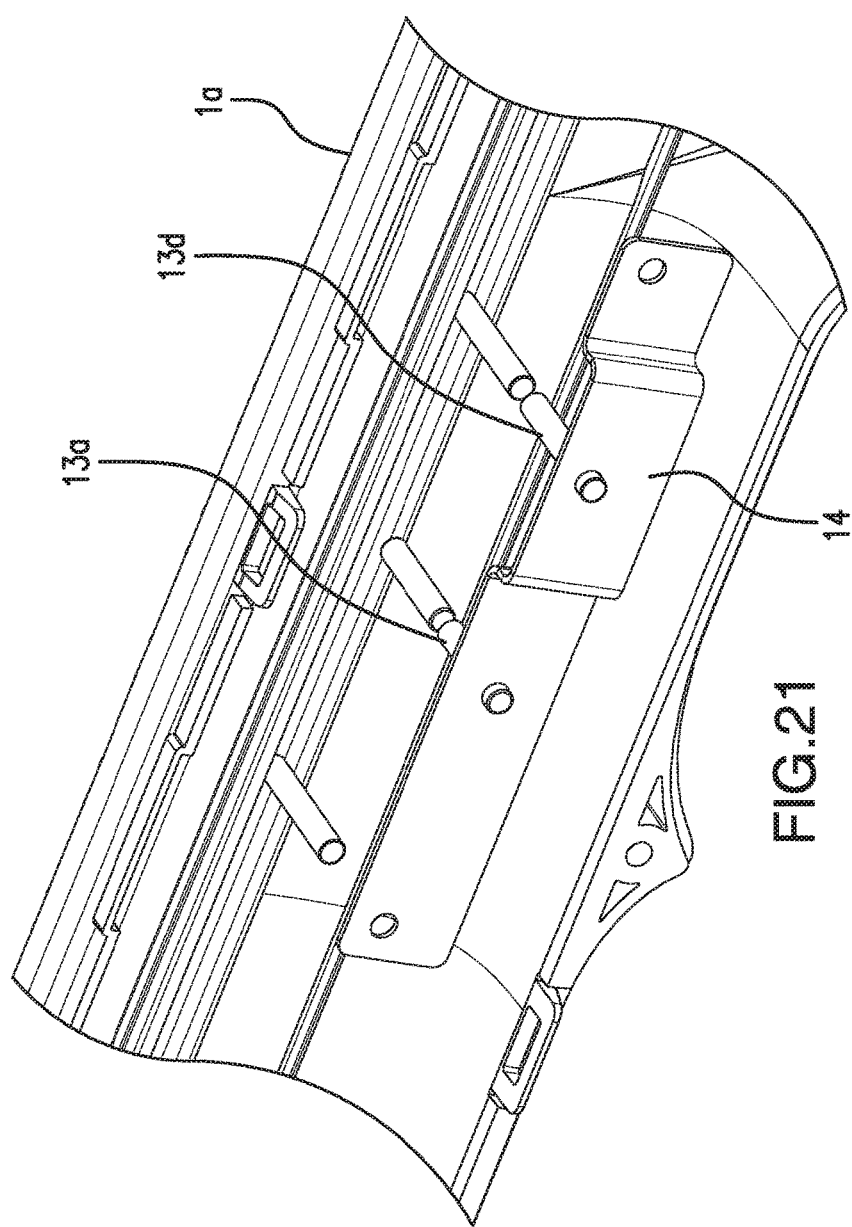
FIG. 21 is an enlarged view showing the relationship between the handle, pins, and plate of the delivery system of FIG. 1.

The actuation assembly 2 can further include a plate 14 disposed on the shuttle assembly 9. The plate 14 can hold portions of the actuation assembly 2 in place and can protect the actuation assembly 2. The actuation assembly 2 can also include at least one pin 13 configured to engage at least one pin track disposed within the handle 1 to thereby guide the shuttle frame 9 along the handle, as shown in FIG. 21 for the purpose of illustration and not limitation. A pin track can be on the first side of the handle housing 1a, the second side of the handle housing 1b, or on both sides of handle 1. The at least one pin can include a first pin 13a disposed through an axis of the sun gear shaft 3. The actuation assembly can include additional pins, such as a second pin 13b and a third pin 13c (FIG. 2), each disposed through the plate 14 and the shuttle frame 9. The second pin 13b and third pin 13c can hold the plate 14 in place on the shuttle frame 9. The actuation assembly 2 can include a fourth pin 13d disposed through an axis of the intermediate gear 10. The fourth pin 13d can engage the handle and act as a guide as the shuttle frame 9 moves relative to the handle 1.

Figure 22:
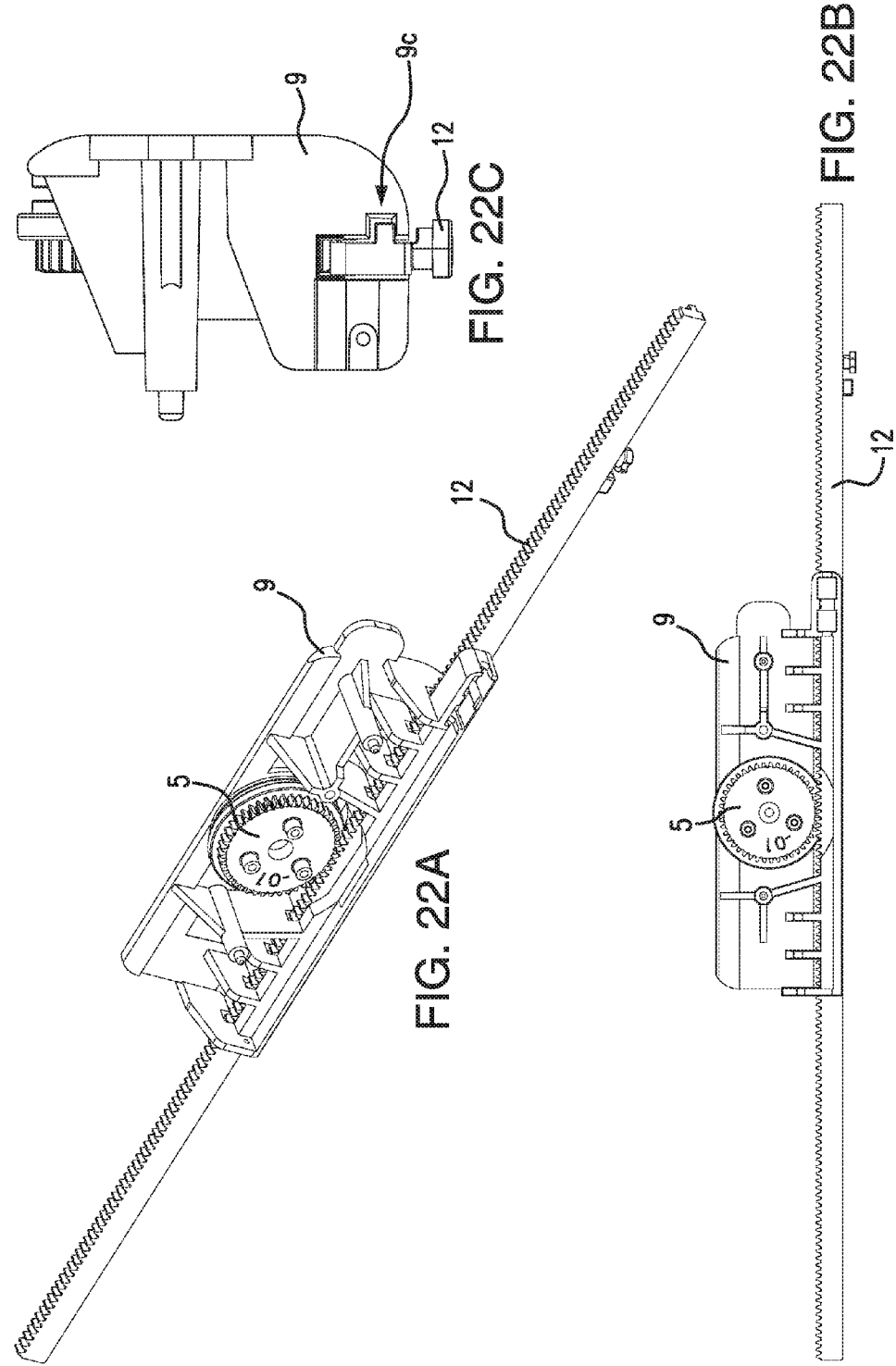
FIGS. 22A-22C are various views showing the relationship between the shuttle frame, driving rack, and planet carrier of the delivery system of FIG. 1.

In accordance with another aspect of the disclosed subject matter, the actuation assembly 2 can be functionally coupled to the trigger 60 by a driving rack 12. For example, the driving rack 12 can be fixedly coupled or releasably coupled to an intermediate element functionally disposed between the driving rack 12 and the trigger 60. As an example and not by way of limitation, the driving rack 12 can have a bayonet-type engagement with the intermediate element. The driving rack 12 can be operatively engaged with the planet carrier 5. For example, the driving rack 12 can be operatively meshed with the circumferential pinion 5a of the planet carrier 5, as shown in FIG. 22 for the purpose of illustration and not limitation. The driving rack 12 can be supported in a guide 9c disposed on the shuttle 9, as shown in FIG. 22 for the purpose of illustration and not limitation. Such a configuration can allow a limited region of contact between the driving rack 12 and the corresponding support surface, thereby reducing friction. Additionally, such a configuration can provide support proximal to the point of contact between the driving rack 12 and the planet carrier 5, even as that point moves along the length of the driving rack 12. In operation, upon deployment of the trigger 60 from the first position to the second position, the driving rack 12 can move distally, relative to the handle 1, and cause the planet carrier 5 to rotate in a first direction. Upon return of the trigger 60 from the second position to the first position, the driving rack 12 can move proximally relative to the handle, and cause the planet carrier 5 to rotate in an opposite direction.

In view of the disclosed subject matter, the dimensions and features of the trigger stop 67, shuttle 9 and elements disposed thereon, sheath rack 1c, and the handle guide can be designed based on the specifics of the implant 23, for example, the diameter of the implant 23. As an example and not by way of limitation, for a given radius of the intermediate gear 10, the sheath rack 1c and the handle guide, can be a specific distance apart to properly engage the small spur gear 10b of the intermediate gear 10 and the pin 13d disposed through the axis of the intermediate gear 10. If the radius of the intermediate gear is changed, the distance between the sheath rack 1c and the handle guide can also be adjusted accordingly.

For purpose of illustration, reference is now made to the operation of the system with the actuation assembly disclosed herein. During operation, the user can deploy the trigger 60 from the first position to the second position (referred to herein as the "first action"). The trigger 60 thus can cause the driving rack 12 to move in the distal direction. The driving rack 12, functionally meshed with the circumferential pinion 5a of the planet carrier 5, can impart rotational motion on the planet carrier 5. The planet carrier 5 can impart rotational motion on the three planet gears 6. The planet gears 6 can be constrained from rotating freely because they are meshed with the sun gear portion 3a of the sun gear shaft 3. The three planet gears 6 can be meshed with the ring gear portion 7b of the ring gear 7, and can impart rotational motion on the ring gear 7. The ring gear 7, can be operatively meshed with the ratchet rack 8, and can drive the ratchet rack 8 distally. The inner shaft member 21, which can be fixedly coupled to the ratchet rack 8, moves distally. The planet carrier 5 can be rotationally coupled to the sun gear shaft 3 by the second clutch driver 4b when rotating in the first action; thus, rotation can be transmitted to the sun gear shaft 3 in a 1:1 ratio. The first clutch driver 4a allows the sun gear shaft 3 to rotate freely relative to the shuttle frame 9 during the first action. The sheath pinion 3b of the sun gear shaft 3 can be meshed with the large spur gear 10a of the intermediate gear 10, and can impart rotational motion on the intermediate gear 10. The small spur gear 10b of the intermediate gear 10 can be operatively meshed with a rack 1e disposed on the second handle housing portion 1b; thus, the rotational motion of the intermediate gear 10 can impart linear motion on the shuttle frame 9 in the proximal direction. The outer tubular member 22, which can be fixedly coupled to the shuttle frame 9 can move proximally relative to the handle. Thus, during the first action, the inner shaft member 21 can move distally relative to the handle 1 and the outer tubular member 22 can move proximally relative to the handle 1.

Upon return of the trigger 60 from the second position to the first position (herein referred to as the "second action"), the driving rack 12 can move proximally relative to the handle 1. The driving rack 12 can impart rotational motion to the planet carrier 5. The planet carrier 5 can transmit rotational motion to the three planet gears 6. The planet gears 6 can rotate about the sun gear shaft 3, which can be held stationary relative the shuttle frame 9 via the first clutch driver 4a. The planet gears 6 can impart rotary motion to the ring gear 7. The ratio of motion between the planet carrier 5 and the ring gear 7 can be determined by the ratio of ring gear portion 7b teeth to sun gear portion 3a teeth (ratio=R/(R+S)). Linear motion can be transmitted to the ratchet rack 8 in the proximal direction by the ring gear 7. The inner shaft member 21 can move proximally relative to the handle 1. Thus, during the second action, the inner shaft member moves proximally relative to the handle 1 and the outer tubular member 22 is stationary relative to the handle.

Figure 23:
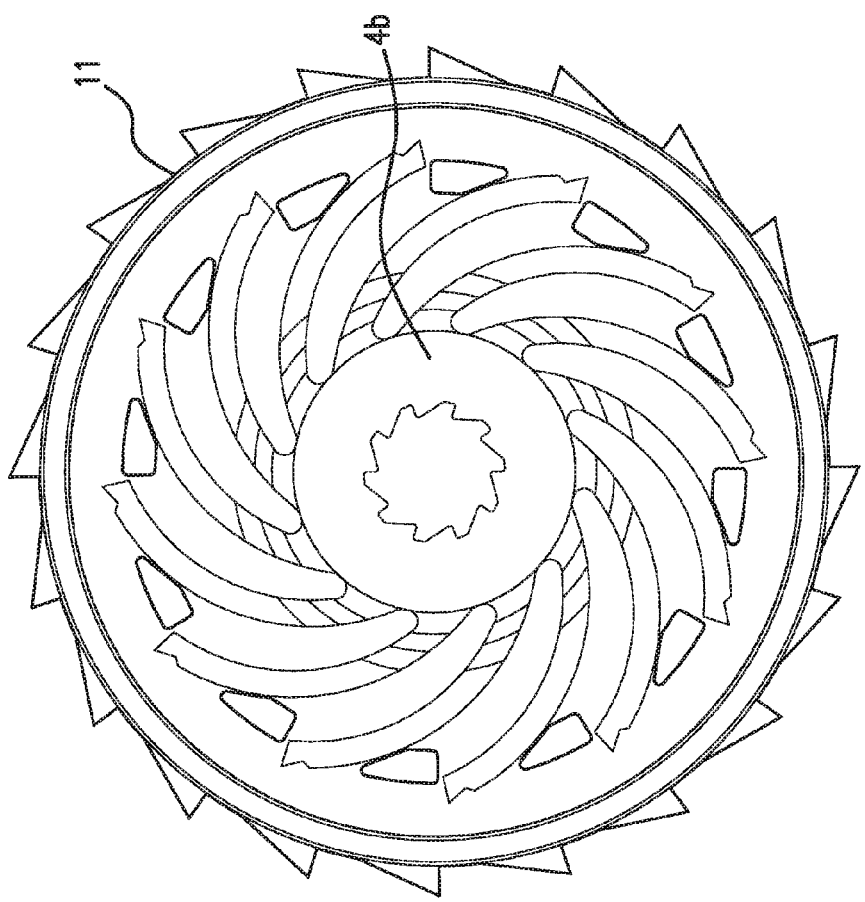
FIG. 23 is a side view showing the relationship between the clutch release and the second clutch driver of the delivery system of FIG. 1.

As further embodied herein, the actuation assembly 2 can include a clutch release 11. The clutch release 11 can be operatively coupled to the second clutch driver 4b and can be configured to prevent the second clutch driver 4b from uni-directionally locking the sun gear shaft 3 and the planet carrier 5 when the clutch release 11 is engaged by a stop 1d. For example, the clutch release 11 can prevent the clutch portion of the second clutch driver 4b from engaging with the clutch component 5b of the planet carrier 5 by urging elements of the clutch portion away from the clutch component 5b, as shown in FIG. 23, for the purpose of illustration and not limitation. Thus, the clutch release 11 can prevent the sun gear shaft 3, planet carrier 5 and ring gear 7 rotating with a 1:1 ratio during the first motion. Rather, when the clutch release 11 is engaged by the stop 1d, the ratio of motion between planet carrier 5 and the ring gear 7 is the same for the first motion and the second motion. The stop 1d can be disposed on the handle 1, for example on the second handle housing portion 1b. The stop 1d can be configured to engage the clutch release 11 when the actuation assembly 2 has moved proximally a distance (z) along the handle 1. Any suitable distances for (z) can be used. The stop 1d can be inserted into a receiving pocket disposed on the handle or otherwise secured with known techniques. The clutch release 11 can include a saw-tooth portion 11a or other suitable configuration, and the stop 1d can include a resilient abutment portion. The saw-tooth portion of the clutch 11 thus can be configured to engage the resilient abutment portion of the stop 1d. As an example, the stop can be P-shaped stop that can provide compliance and opposing bias when the resilient abutment portion of the stop 1d engages the saw-tooth portion of the clutch 11. Such a configuration can prevent or inhibit disengagement of the clutch release 11 and the clutch component 5b of the planet carrier 5.

Figure 24:
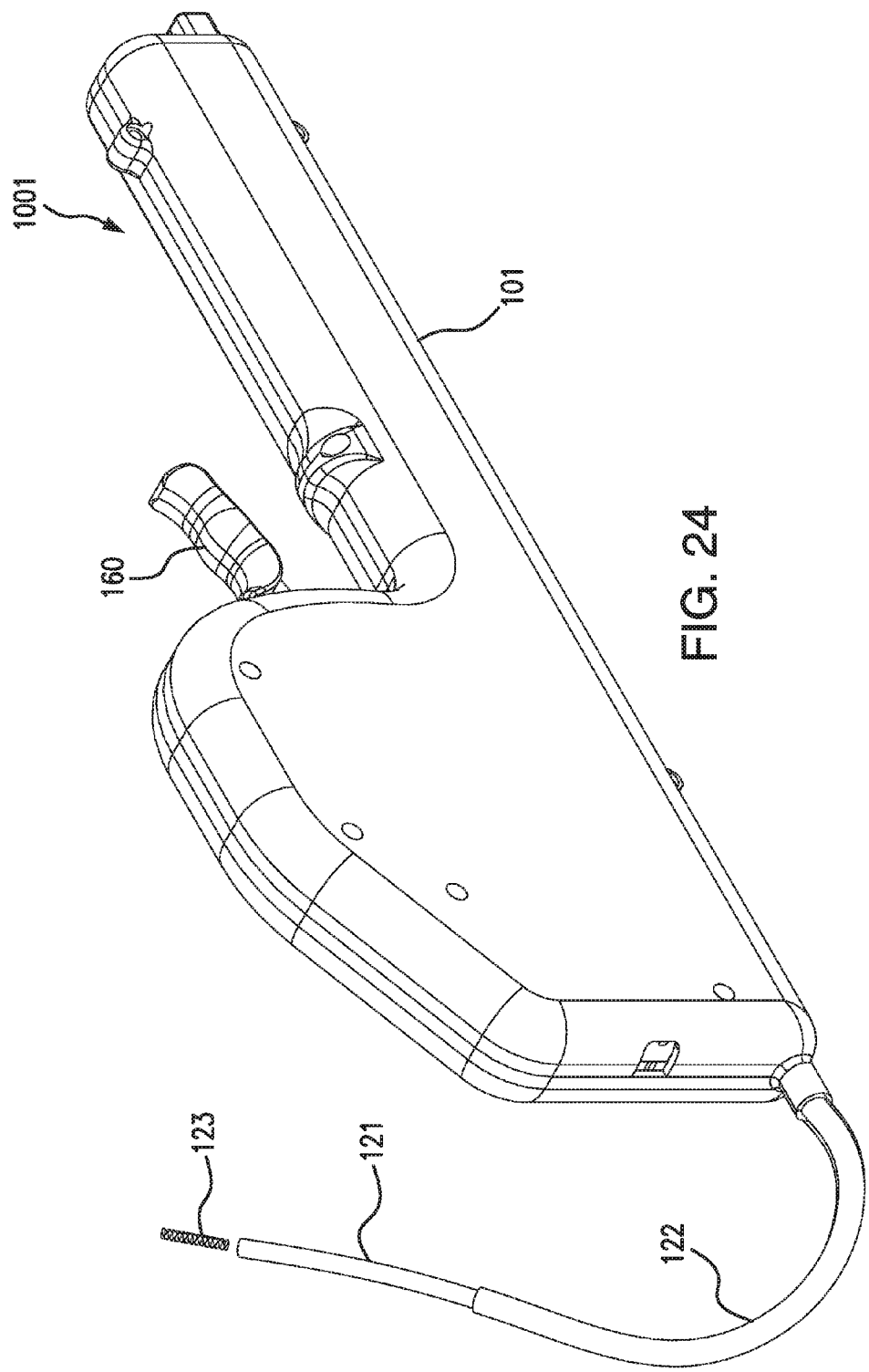
FIG. 24 is a perspective view of a another exemplary embodiments of a delivery system in accordance with the disclosed subject matter.
Figure 25:
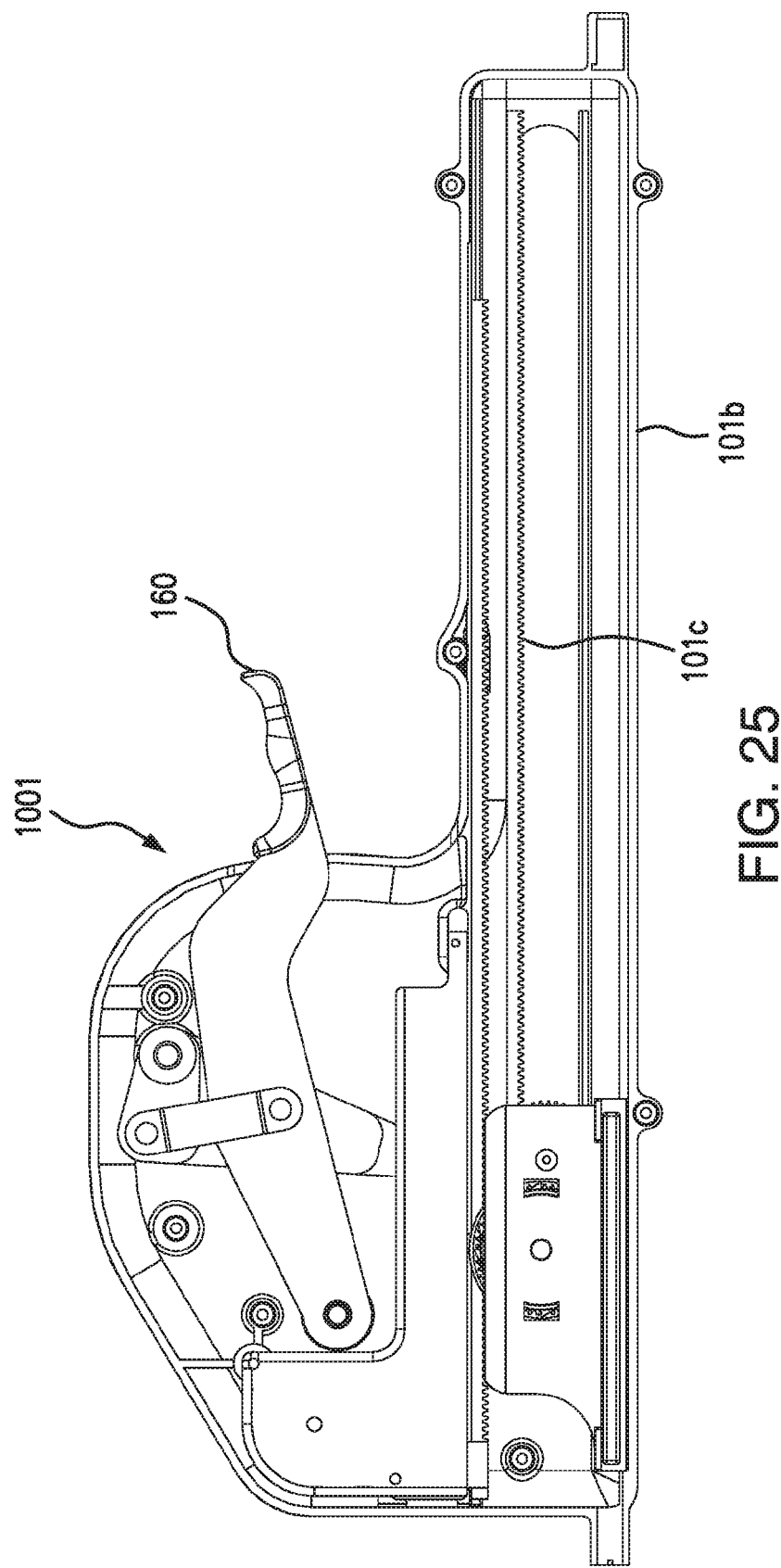
FIG. 25 is a right side view, with a portion of the handle housing removed, of the delivery system of FIG. 24.
Figure 26:
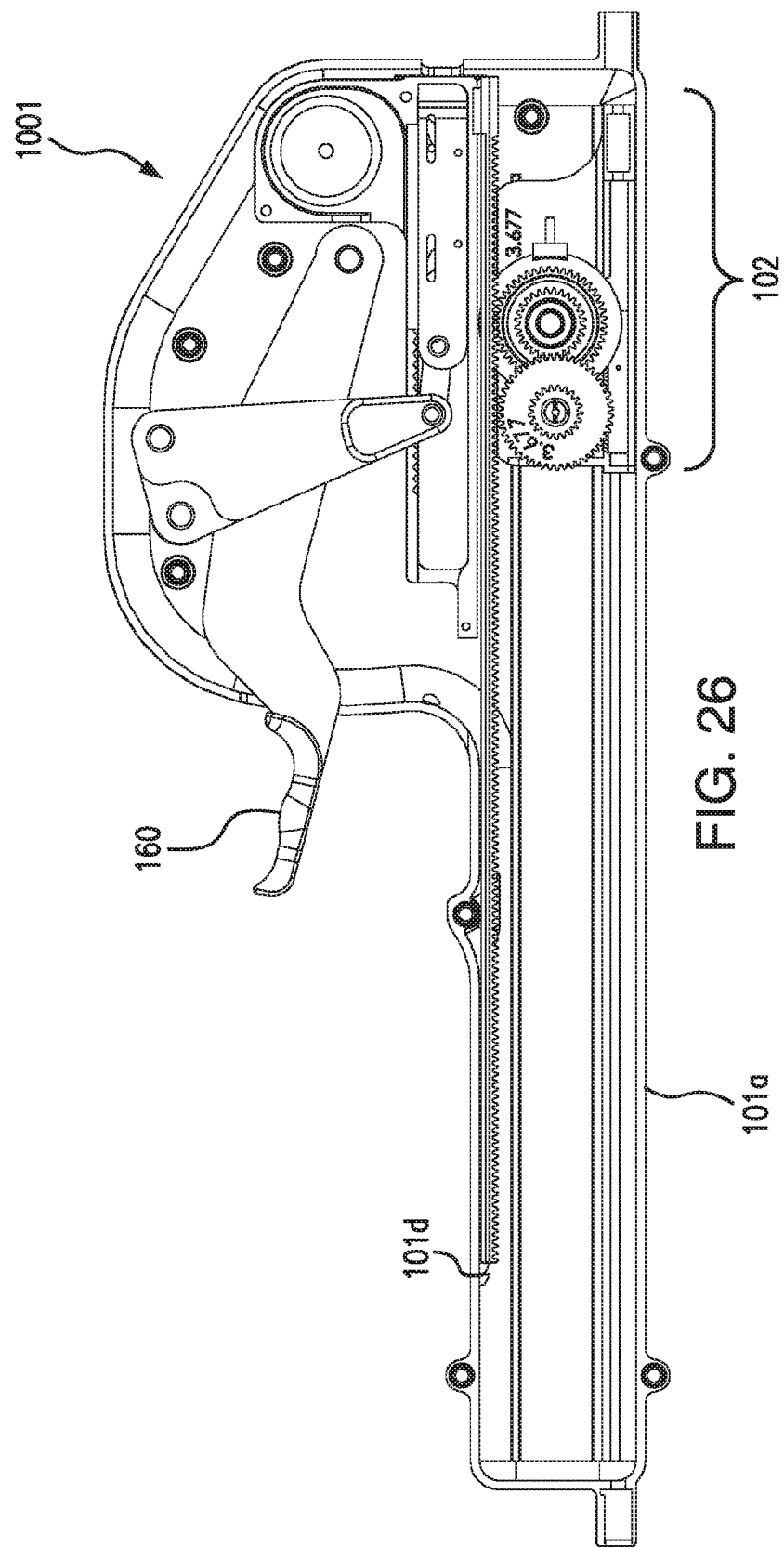
FIG. 26 is a left side view, with a portion of the handle housing removed, of the delivery system of FIG. 24.
Figure 28A:
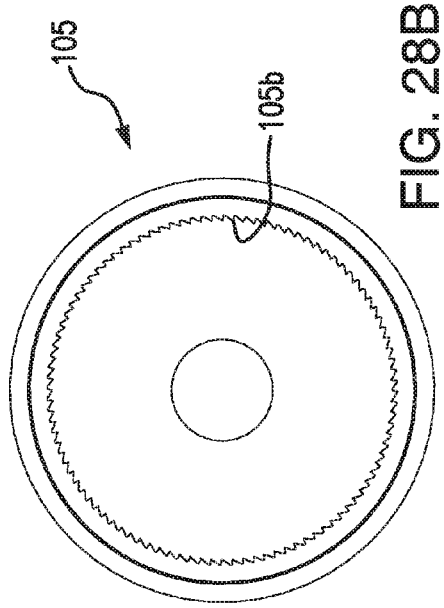
FIGS. 28A-28D provide perspective FIG. 28A, right FIG. 28B, left FIG. 28C, and front FIG. 28D views of the planet carrier of the delivery system of FIG. 24.
Figure 28C:
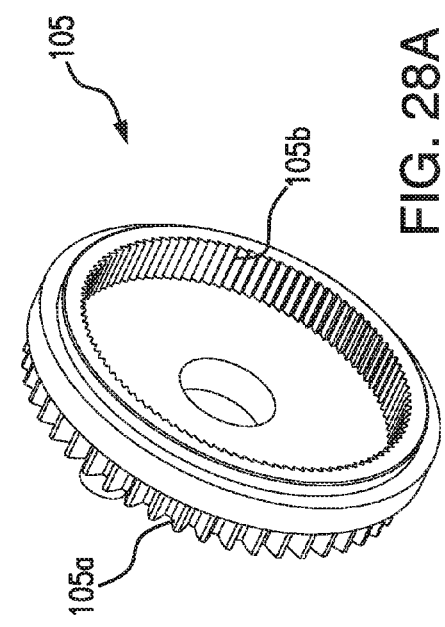
Figure 28B:
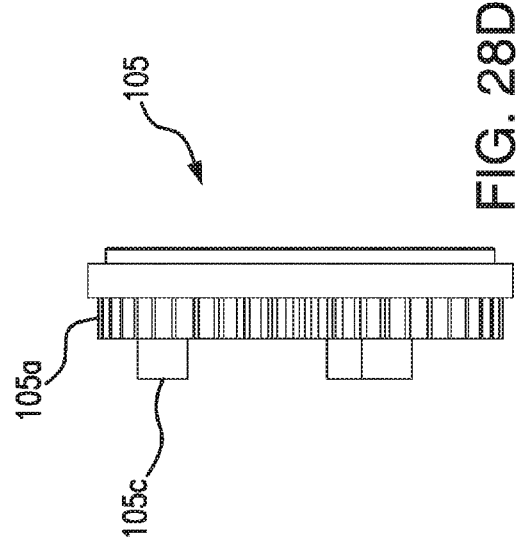
Figure 28D:
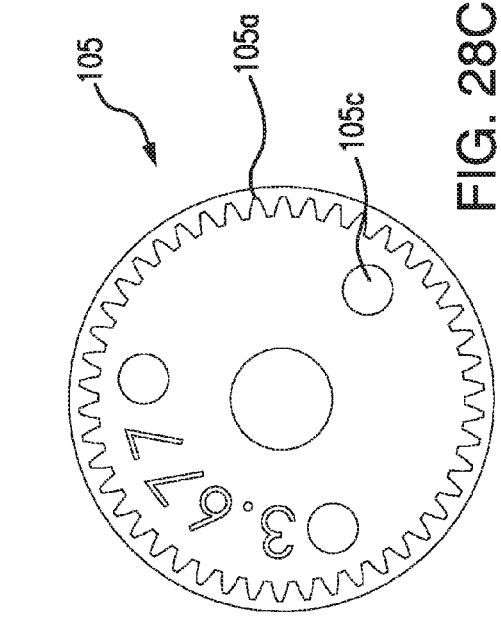
Figure 29A:
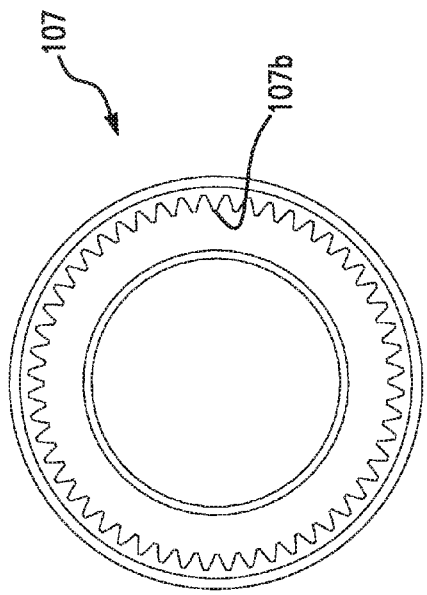
FIGS. 29A-29D provide perspective FIG. 29A, right FIG. 29B, left FIG. 29C, and front FIG. 29D views of the ring gear of the delivery system of FIG. 24.
Figure 29B:
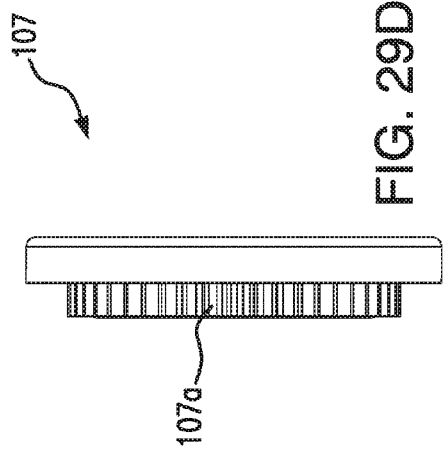
Figure 29C:
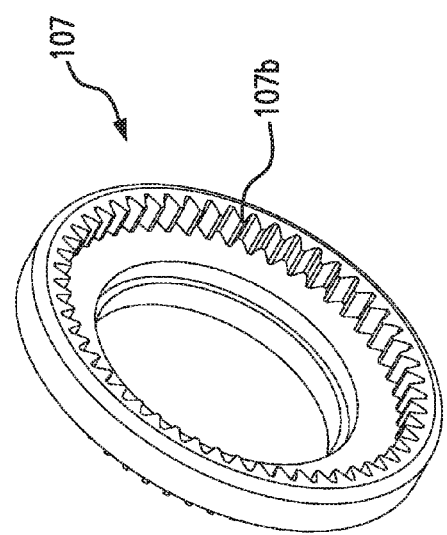
Figure 29D:
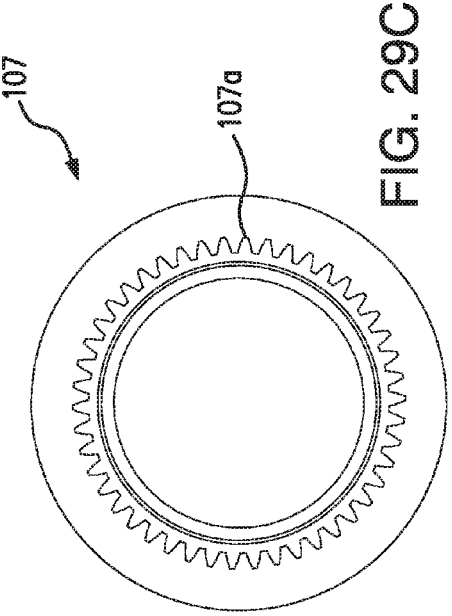
Figure 30A:
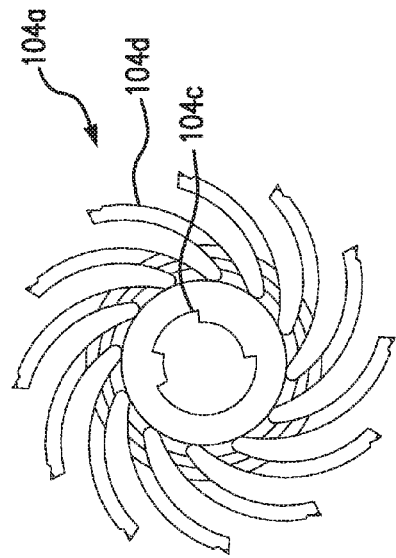
FIGS. 30A-30D provide perspective FIG. 30A, right FIG. 30B, left FIG. 30C, and front FIG. 30D views of the first clutch driver of the delivery system of FIG. 24.
Figure 30B:
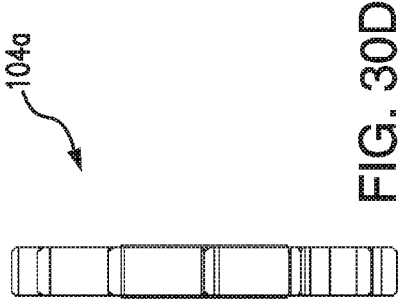
Figure 30D:
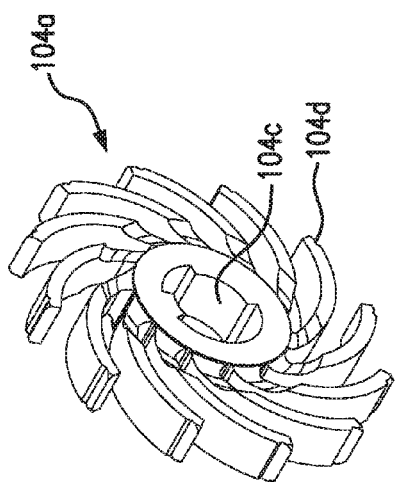
Figure 30C:
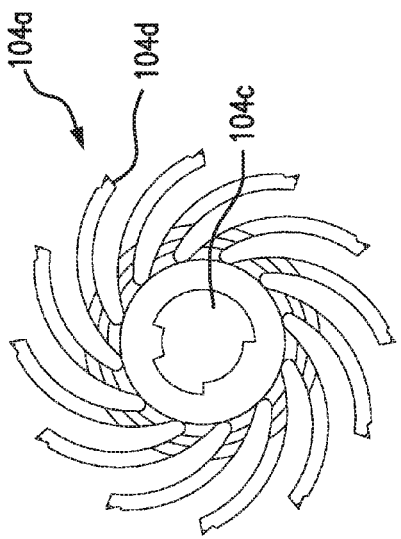
Figure 33A:
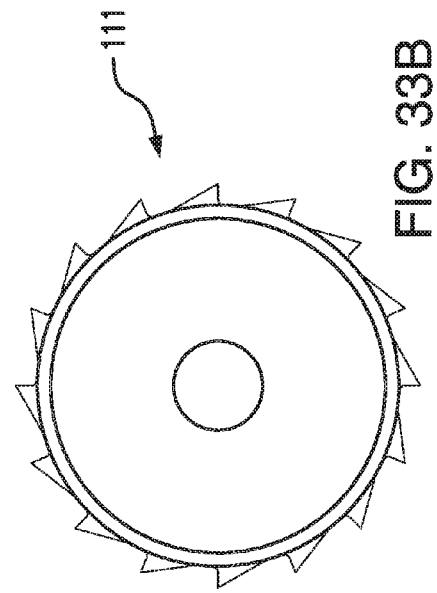
FIGS. 33A-33D provide perspective FIG. 33A, right FIG. 33B, left FIG. 33C, and front FIG. 33D views of the clutch release of the delivery system of FIG. 24.
Figure 33B:
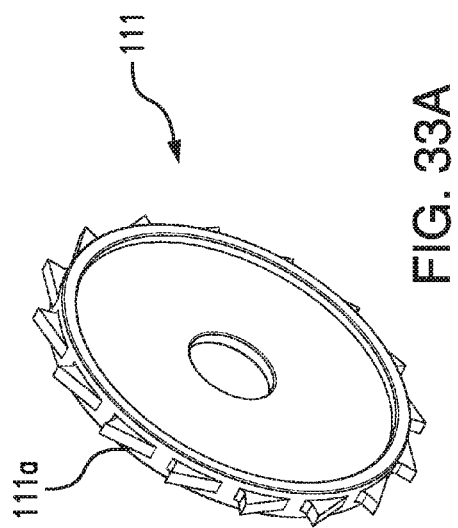
Figure 33C:
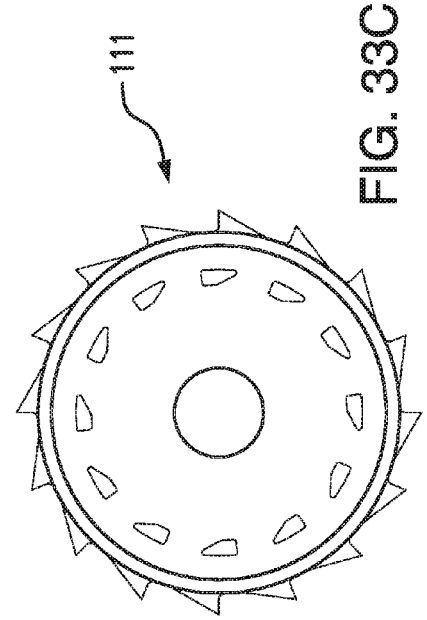
Figure 33D:
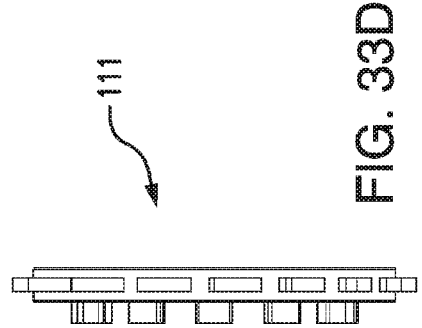

Referring now to FIG. 24 for the purpose of illustration and not limitation, another exemplary embodiment of a system for delivering an implant is provided and designated generally by reference character 1001. Portions of this exemplary embodiment are depicted in FIGS. 25-35. Elements that are similar to the previously described embodiment have been given like numbers. The delivery system 1001 can be configured to deliver an implant in a similar manner as described herein above.

The delivery system 1001 can include a handle 101, an outer tubular member 122, an inner shaft member 121, and an implant 123, for example, a braided implant. The handle 101 can include a trigger 160 and an actuation assembly 102, which can be configured to move the inner shaft member 121 and the outer tubular member 122 relative to the handle 101 as described above upon deployment of the trigger 160 from the first position to the second position and return from the second position to the first position. The trigger 160 can include a lock as described herein above.

Referring now to FIGS. 25-35 for the purpose of illustration and not limitation, the actuation assembly 102 can include a planetary gear system. For purpose of illustration and not limitation, the actuation assembly 102 can be suitably similar to that of the previous embodiment. However, as an alternative to the actuation assembly of the previous embodiment, certain modifications can be incorporated. For example, the ratchet rack 108 can be operatively meshed with the planet carrier 105, and the driving rack 112 can be operatively meshed with the ring gear 107.

The actuation assembly 102 can include a sun gear shaft 103 (which can include a sun gear portion 103a, a sheath pinion 103b, and a clutch engagement portion 103c; FIG. 27), a planet carrier 105 (which can include a circumferential pinion 105a, a clutch component 105b, and at least one pin 105c; FIG. 28), at least one planet gear 106, a ring gear 107 (which can include a circumferential pinion 107a and a ring gear portion 107b; FIG. 29), a first clutch driver 104a and a second clutch driver 104b, both identical in shape (each can include a sun gear shaft engagement portion 104c and a clutch portion 104d; FIG. 30). The actuation assembly 102 can include a shuttle frame 109. The shuttle frame 109 can have the planet carrier 105, planet gears 106, sun gear shaft 103, ring gear 107, and first and second clutch drivers (104a and 104b) disposed thereon. The shuttle frame 109 can be disposed within the handle 101 and can be moveable relative to the handle 101 along the length of the handle 101. The shuttle frame 109 can include a clutch engagement portion 109a, a cavity 109b which can receive a ferrule coupled to the proximal end of the outer tubular member 122, and clips 109d and 109e, which can hold the planetary gear system in place on the shuttle frame 109. The planet carrier 105, planet gears 106, sun gear shaft 103 and ring gear 107 can perform as the respective elements of the planetary gear system as described above. The actuation assembly can also include a ratchet rack 108. The actuation assembly can be functionally coupled to the trigger 160 by a driving rack 112, which can be supported by the handle 101. The actuation assembly can include a clutch release 111 which can engage a stop 101d disposed on the handle, as described herein above with regard to system 1000.

During operation, the user can deploy the trigger 160 from the first position to the second position (referred to herein as the "first action"). The trigger 160 can cause the driving rack 112 to move in a proximal direction. The driving rack 112, functionally meshed with the circumferential pinion 107a of the ring gear 107, can impart rotational motion on the ring gear 107 (FIG. 34). The ring gear portion 107b of the ring gear 107 can be operatively meshed with the planet gears 106, and can impart rotational motion on the planet gears 106. The planet gears 106 are operatively meshed with the sun gear portion 103a of the sun gear shaft 103 and thus can be constrained from rotating freely because they. The movement of the planet gears 106, which are disposed on the pins 105c of the planet carrier 105, can impart rotational motion on the planet carrier 105. The planet carrier 105 and the sun gear shaft 103 can be rotationally coupled by the second clutch driver 104b when rotating in the first action; thus, rotation can be transmitted to the sun gear shaft 103 in a 1:1 ratio. The first clutch driver 104a can allow the sun gear shaft 103 to rotate freely relative to the shuttle frame 109 during the first action. The sheath pinion 103b of the sun gear shaft 103 can be meshed with the large spur gear 110a of an intermediate gear 110, and can impart rotational motion on the intermediate gear 110. The small spur gear 110b of the intermediate gear 110 can be operatively meshed with a rack 101c disposed on the second handle housing portion 101b; thus, the rotational motion of the intermediate gear 110 can impart linear motion on the shuttle frame 109 in the proximal direction. The outer tubular member 122, which can be fixedly coupled to the shuttle frame 109, can move proximally relative to the handle 101. The circumferential pinion 105a of the planet carrier 105 can be operatively meshed with a ratchet rack 108, and rotation of the planet carrier 105 can move the ratchet rack 108 distally (FIG. 35). The inner shaft member 121, which can be fixedly coupled to the ratchet rack 108, moves distally. Thus, during the first action, the inner shaft member 121 can move distally relative to the handle 101 and the outer tubular member 122 can move proximally relative to the handle 101.

Upon return of the trigger 160 from the second position to the first position (herein referred to as the "second action"), the driving rack 112 can move distally relative to the handle 101. The driving rack 112 can impart rotational motion on the ring gear 107. The ring gear 107 can impart rotational motion on the three planet gears 106. The planet gears 106 can rotate about the sun gear shaft 103, which can be held stationary relative the shuttle frame 109 via the first clutch driver 104a. The planet gears 106 can impart rotational motion on the planet carrier 105. Linear motion in the proximal direction can be transmitted to the ratchet rack 108 by the planet carrier 105. The inner shaft member 121, fixedly coupled to the ratchet rack 108, can move proximally relative to the handle 101. Thus, during the second action, the inner shaft member 121 can move proximally relative to the handle 101 and the outer tubular member 122 can be stationary relative to the handle 101.

Figure 36:
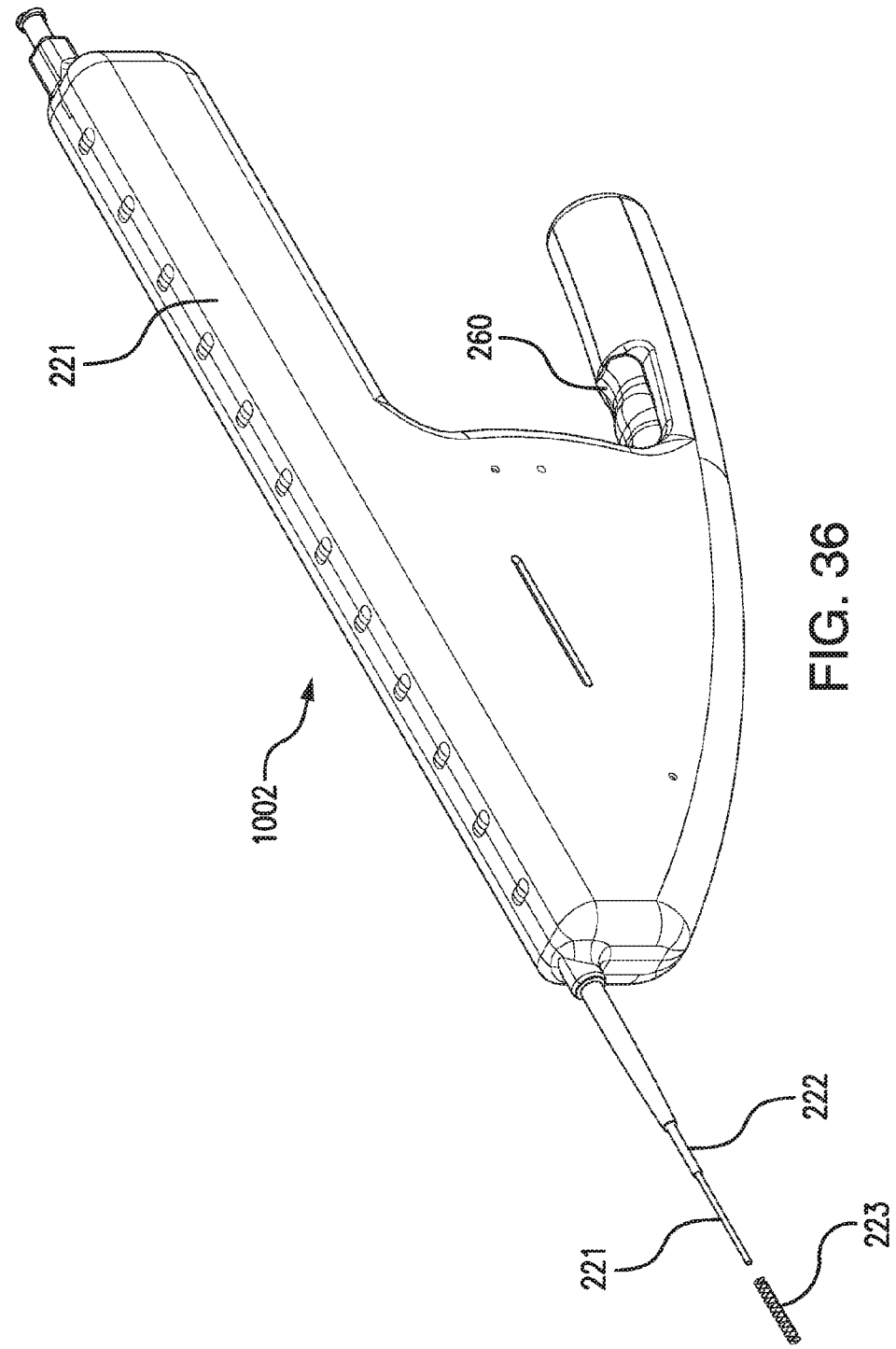
FIG. 36 is a perspective view of a yet another exemplary embodiment of delivery system in accordance with the disclosed subject matter.
Figure 37:
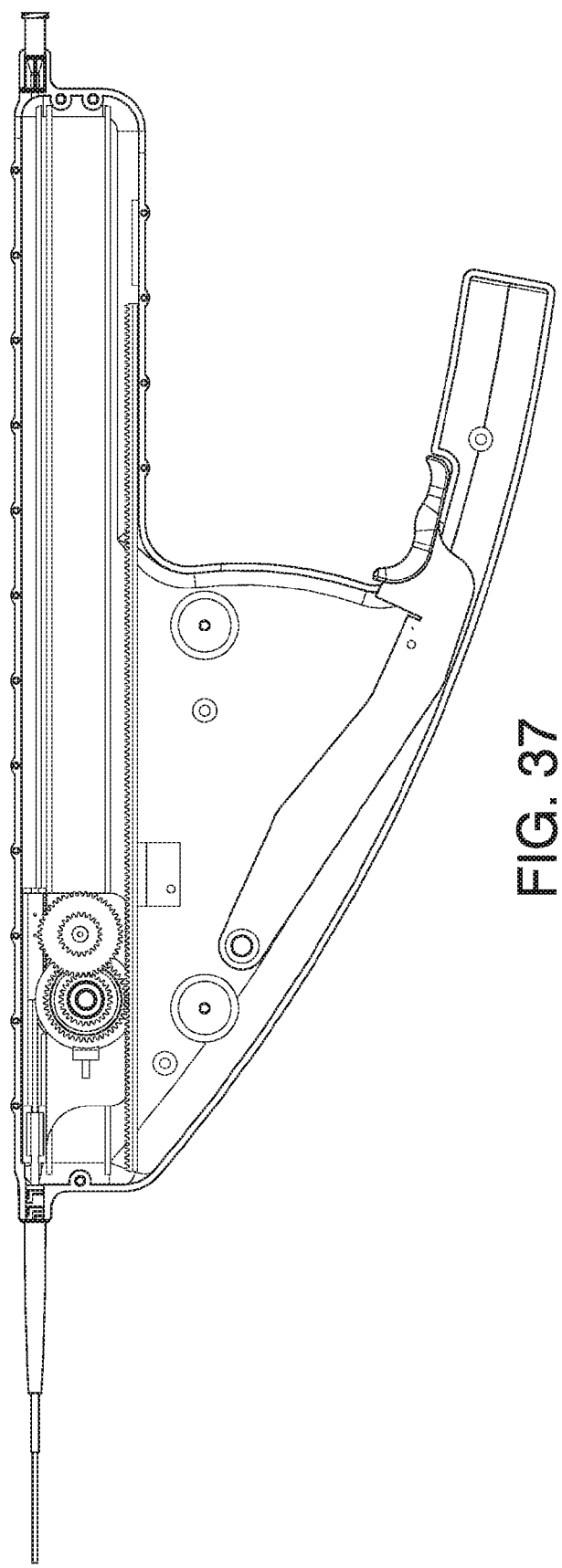
FIG. 37 is a right side view, with a portion of the handle housing removed, of the delivery system of FIG. 36.
Figure 39A:
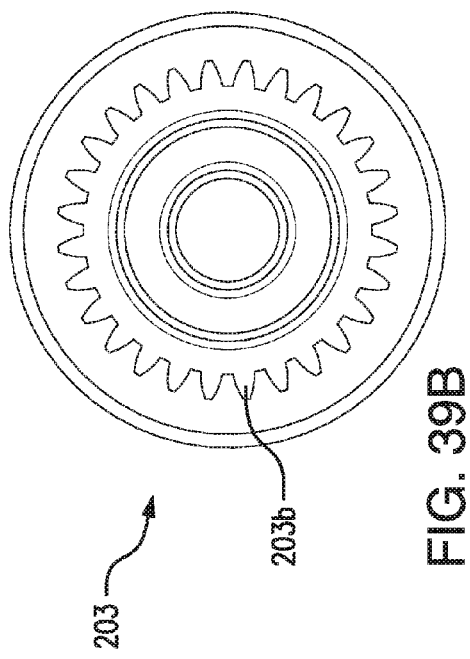
FIGS. 39A-39D provide perspective FIG. 39A, right FIG. 39B, left FIG. 39C, and front FIG. 39D views of the sun gear shaft of the delivery system of FIG. 36.
Figure 39B:
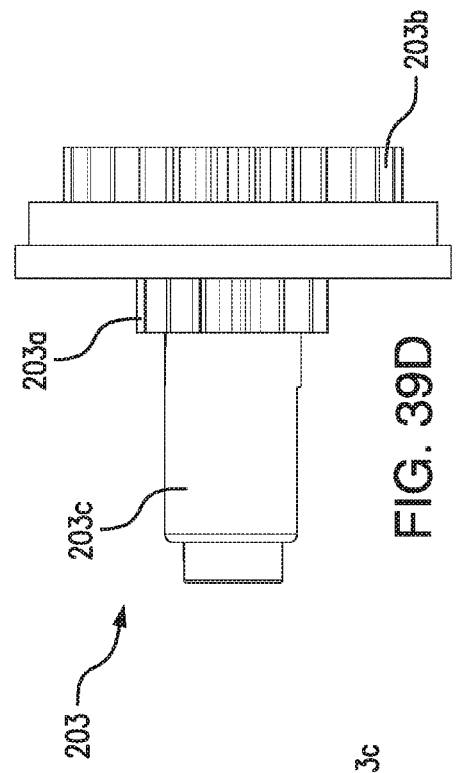
Figure 39C:
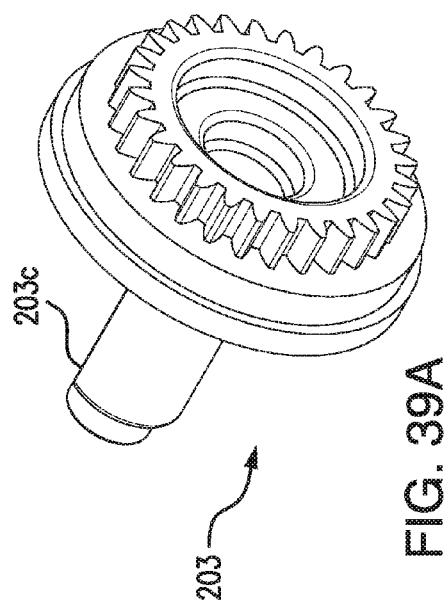
Figure 39D:
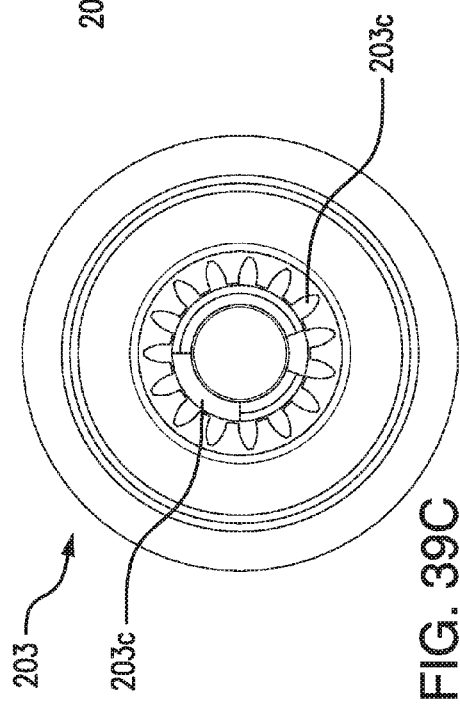
Figure 40B:
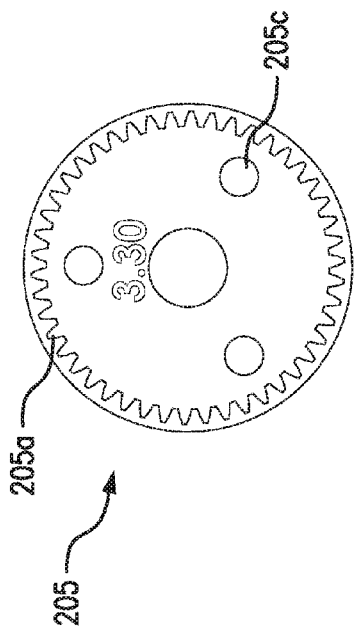
FIGS. 40A-40D provide perspective FIG. 40A, right FIG. 40B, left FIG. 40C, and front FIG. 40D views of the planet carrier of the delivery system of FIG. 36.
Figure 40D:
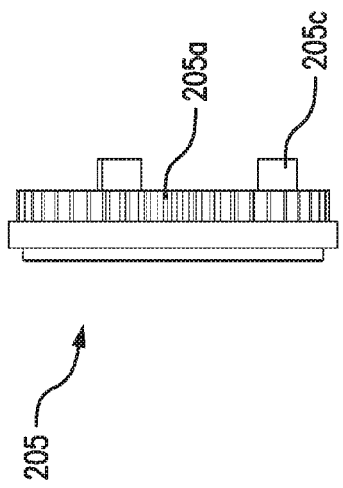
Figure 40A:
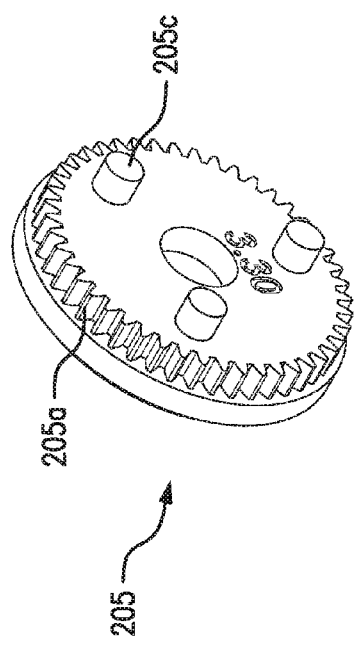
Figure 40C:
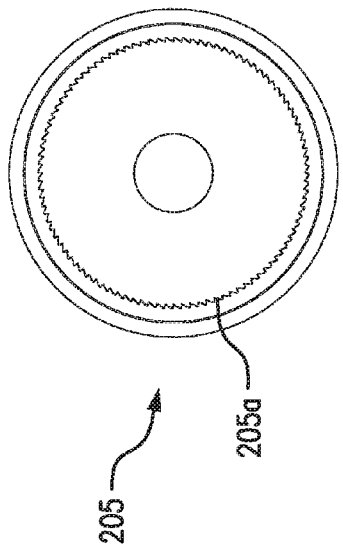
Figure 41B:
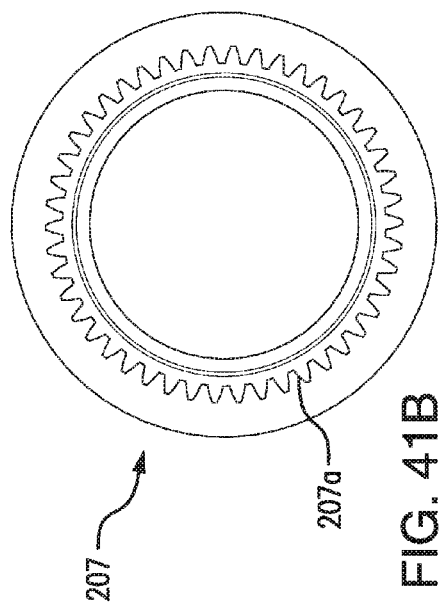
FIGS. 41A-41D provide perspective FIG. 41A, right FIG. 41B, left FIG. 41C, and front FIG. 41D views of the ring gear of the delivery system of FIG. 36.
Figure 41D:
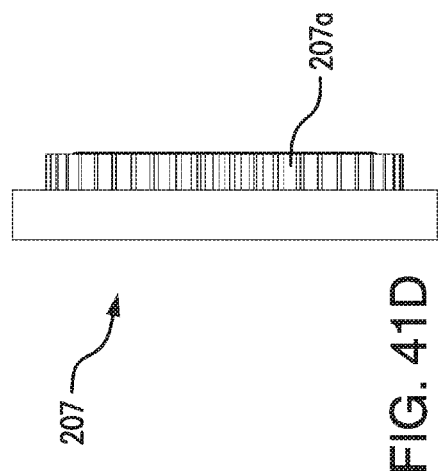
Figure 41A:
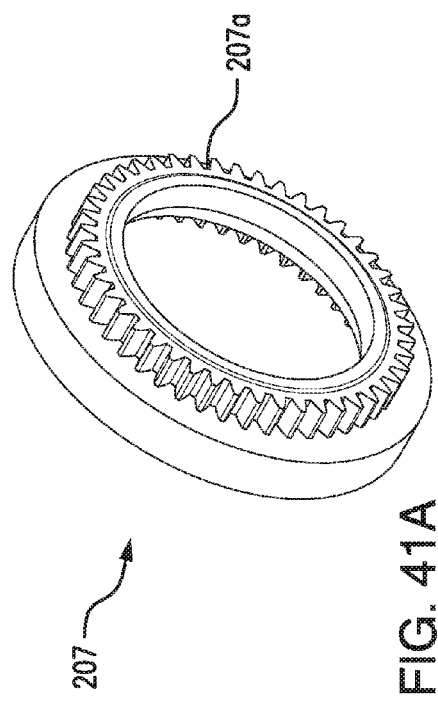
Figure 41C:
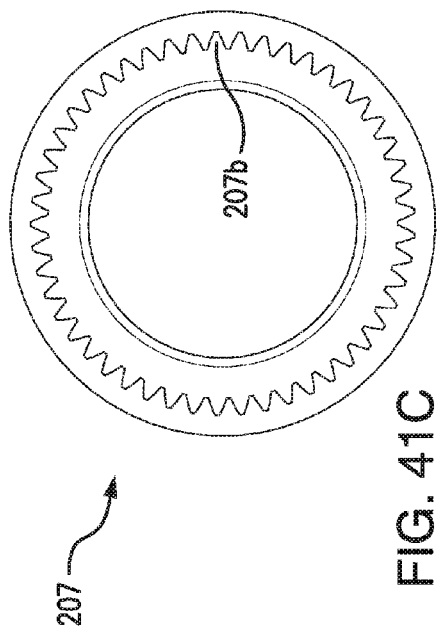
Figure 43A:
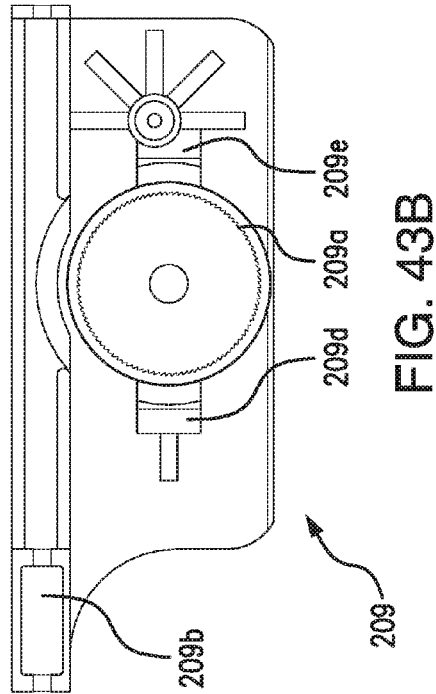
FIGS. 43A-43D provide perspective FIG. 43A, right FIG. 43B, left FIG. 43C, and front FIG. 43D views of the shuttle frame of the delivery system of FIG. 36.
Figure 43B:
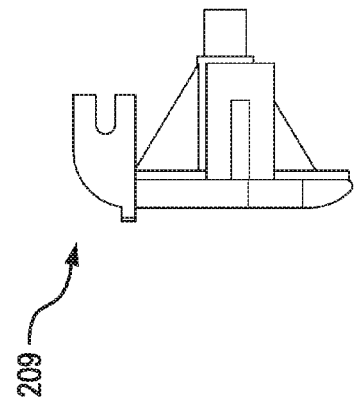
Figure 43C:
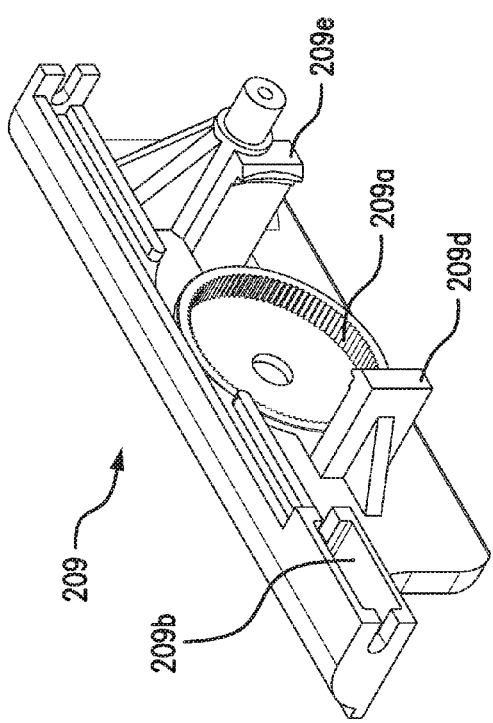
Figure 43D:
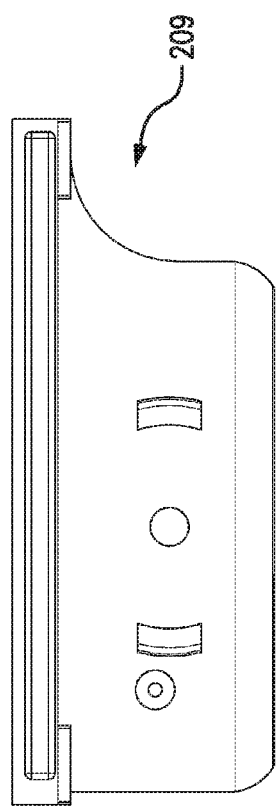
Figure 44B:
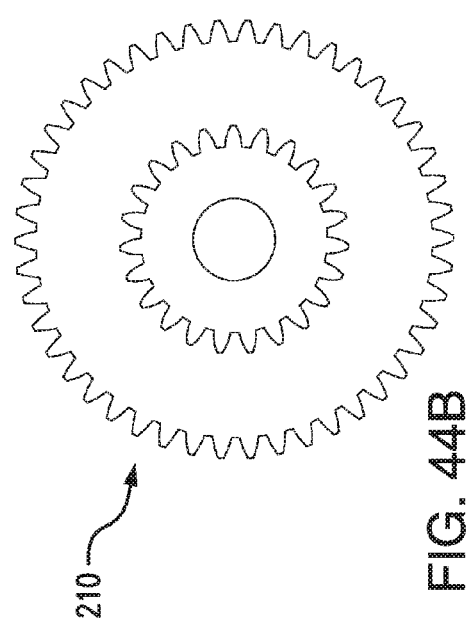
FIGS. 44A-44D provide perspective FIG. 44A, right FIG. 44B, left FIG. 44C, and front FIG. 44D views of the intermediate gear of the delivery system of FIG. 36.
Figure 44D:
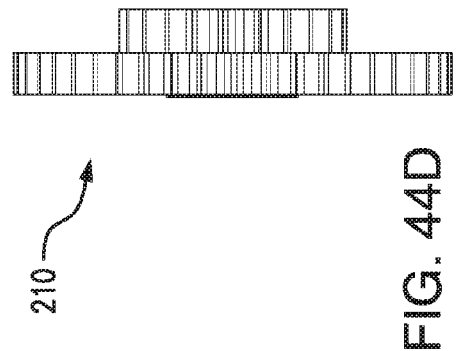
Figure 44A:
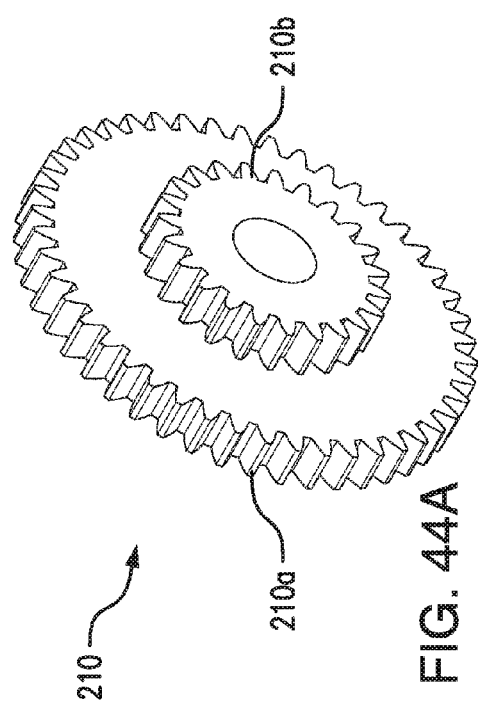
Figure 44C:
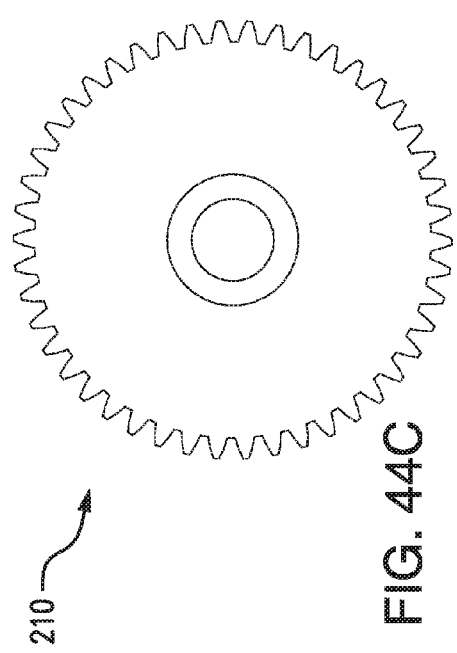
Figure 48A:
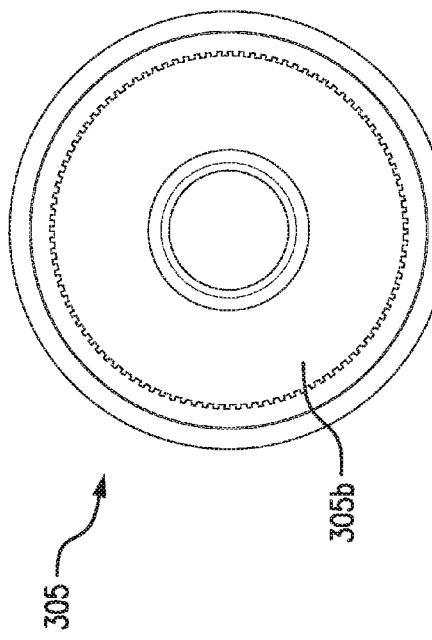
FIGS. 48A-48D provide perspective FIG. 48A, right FIG. 48B, left FIG. 48C, and front FIG. 48D views of the planet carrier of the delivery system of FIG. 46.
Figure 48B:
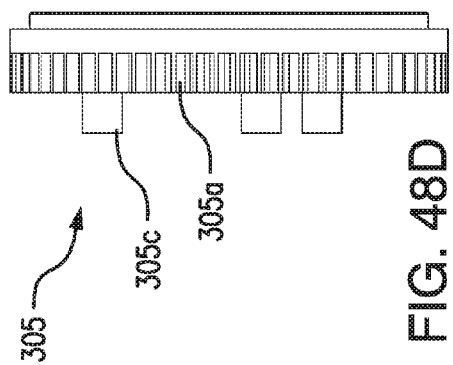
Figure 48C:
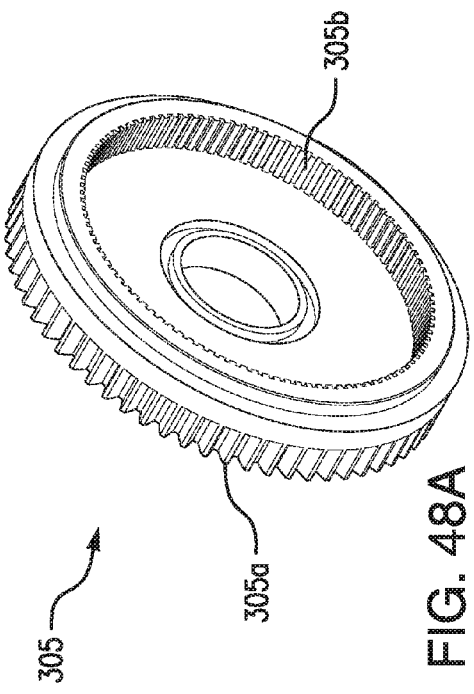
Figure 48D:
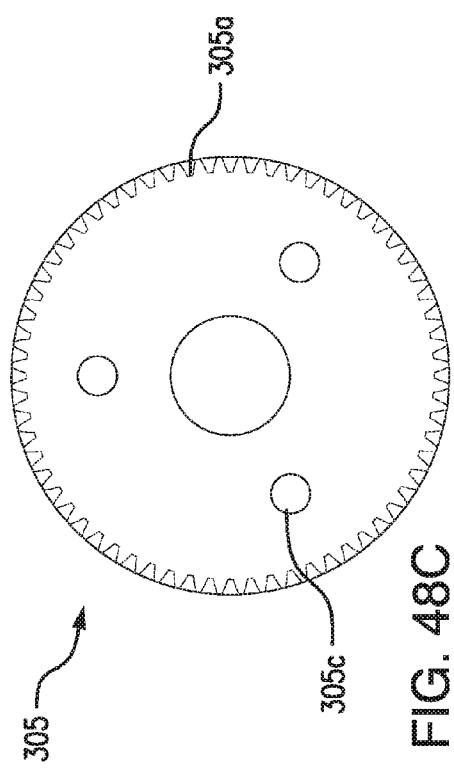
Figure 49A:
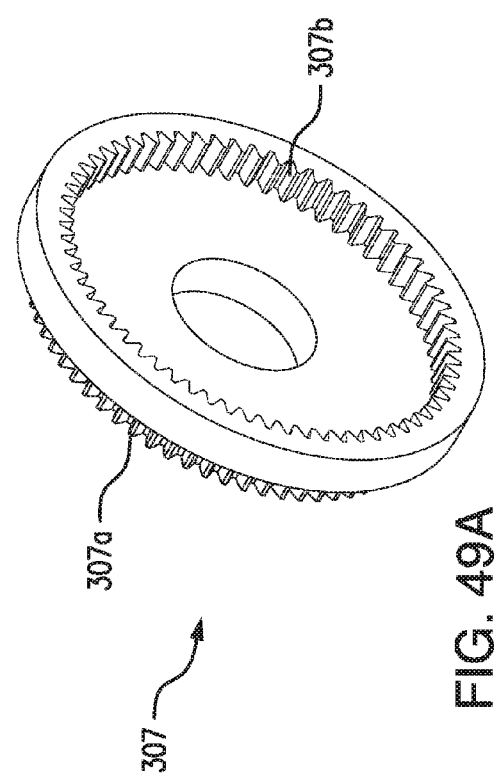
FIGS. 49A-49D provide perspective FIG. 49A, right FIG. 49B, left FIG. 49C, and front FIG. 49D views of the ring gear of the delivery system of FIG. 46.
Figure 49B:
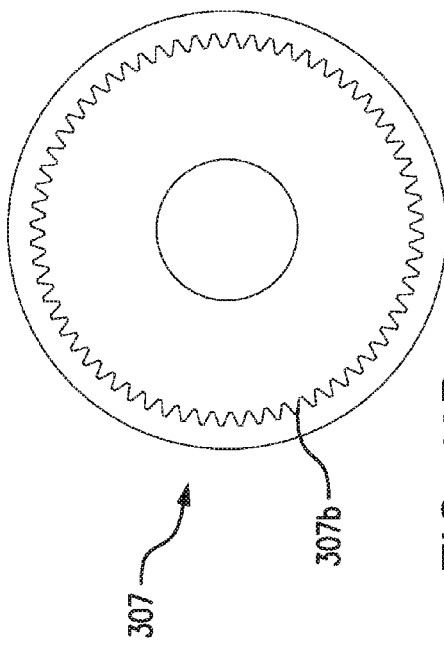
Figure 49D:
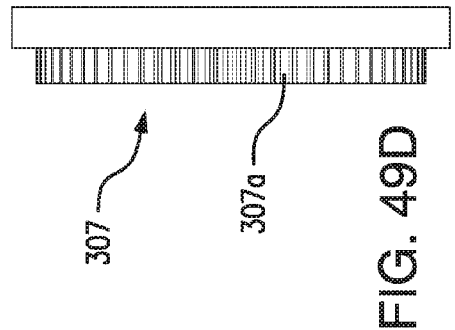
Figure 49C:
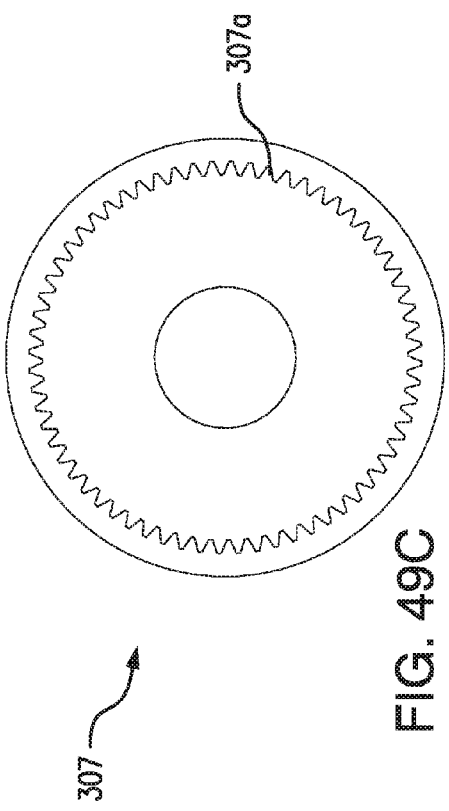
Figure 50B:
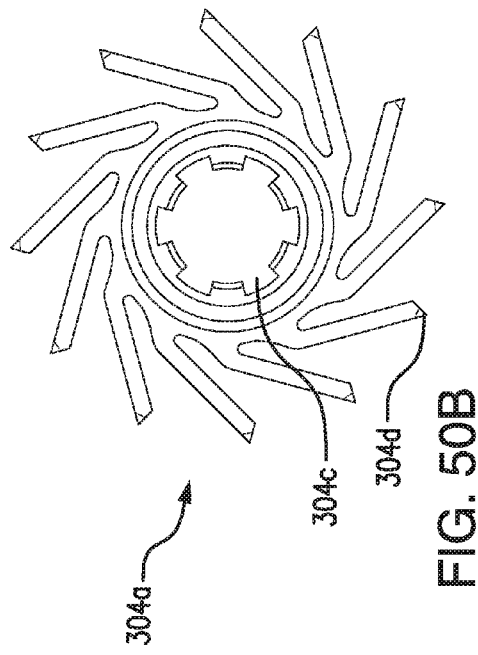
FIGS. 50A-50 D provide perspective FIG. 50A, right FIG. SOB, left FIG. 50C, and front FIG. 50D views of the first clutch driver of the delivery system of FIG. 46.
Figure 50D:
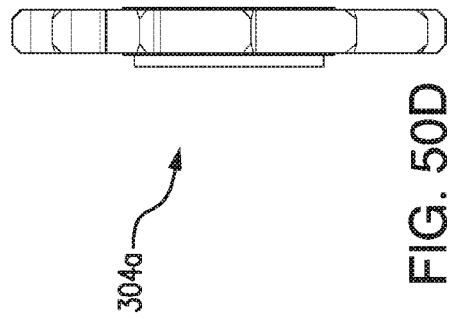
Figure 50A:
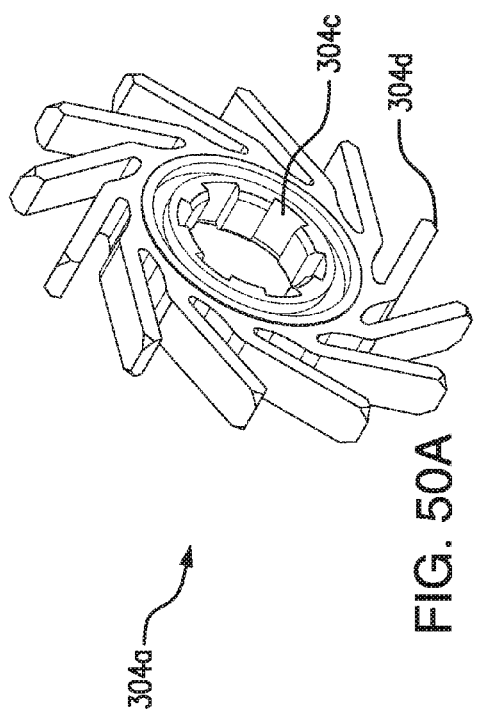
Figure 50C:
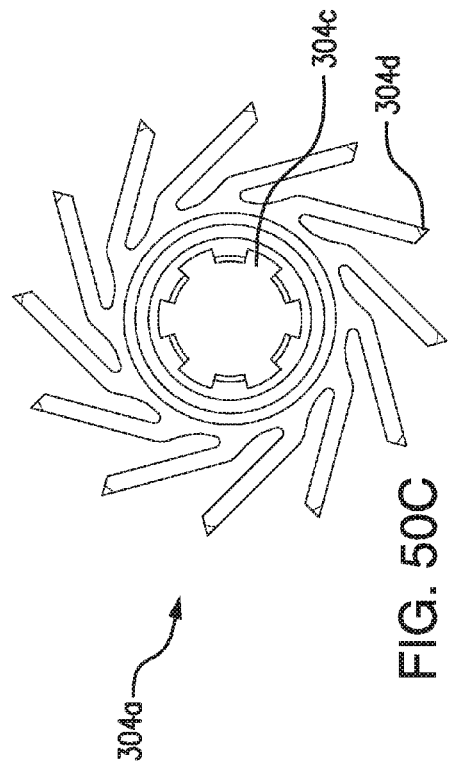
Figure 53:
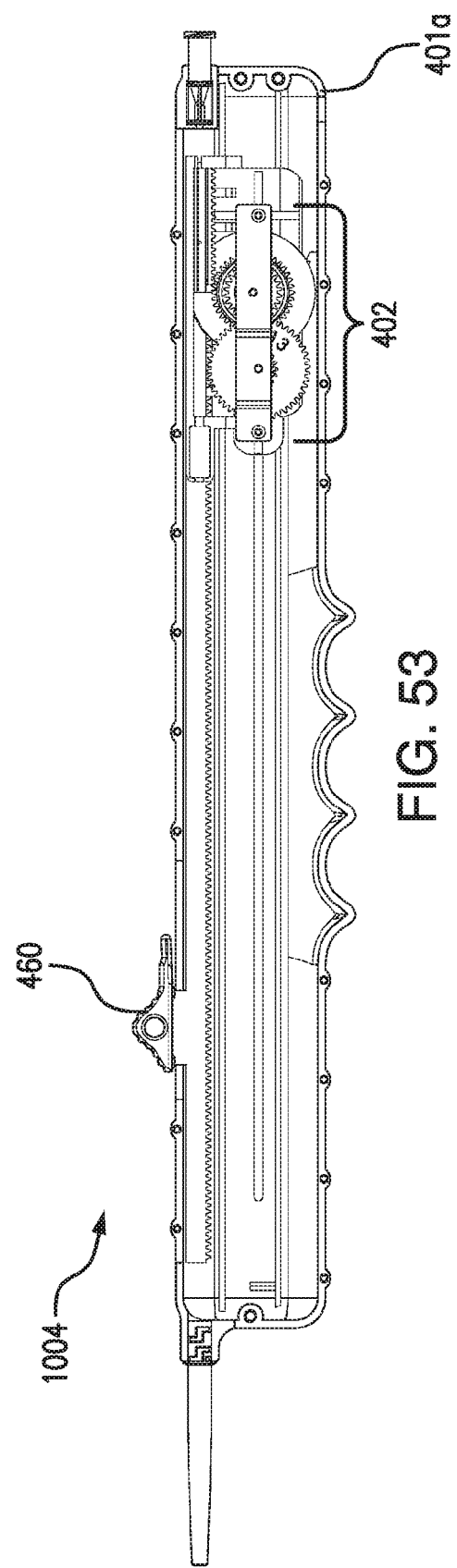
FIG. 53 is a right side view, with a portion of the handle housing removed, of the delivery system of FIG. 52.
Figure 55A:
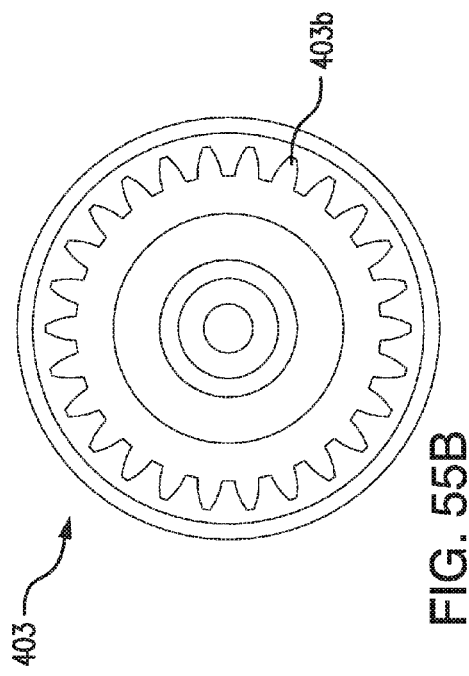
FIGS. 55A-55D provide perspective FIG. 55A, right FIG. 55B, left FIG. 55C, and front FIG. 55D views of the sun gear shaft of the delivery system of FIG. 52.
Figure 55B:
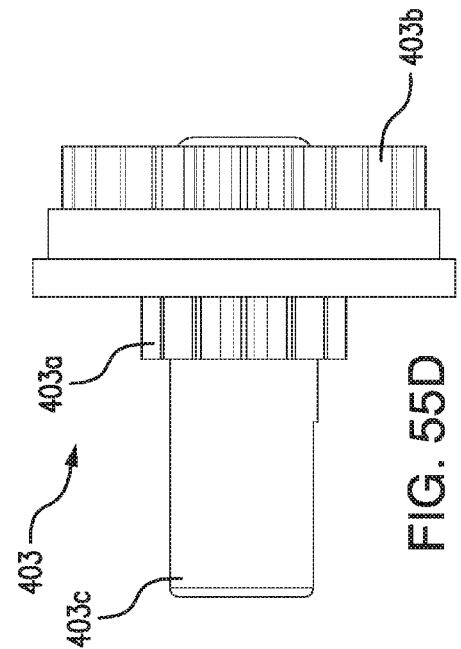
Figure 55C:
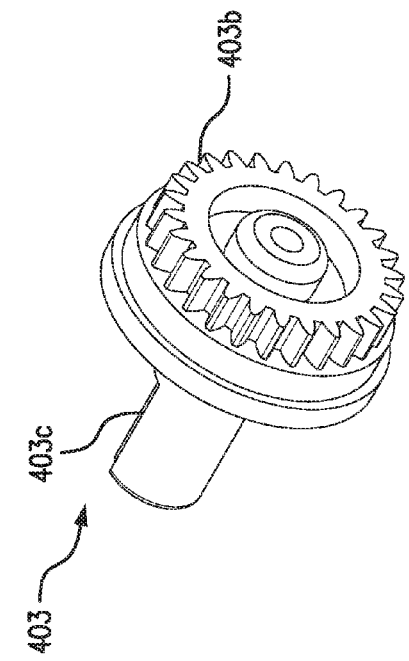
Figure 55D:
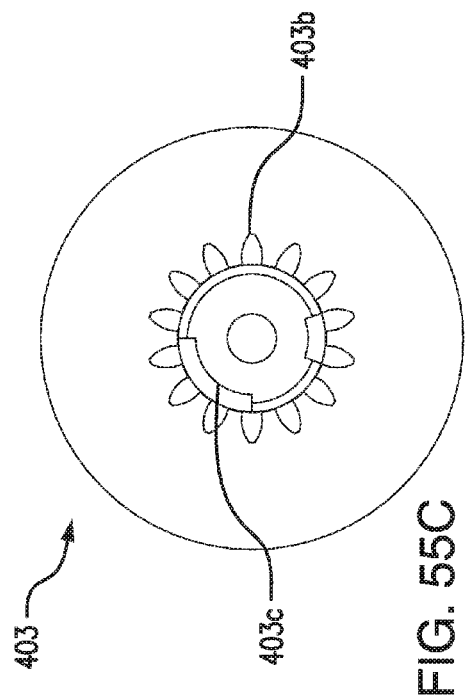
Figure 57B:
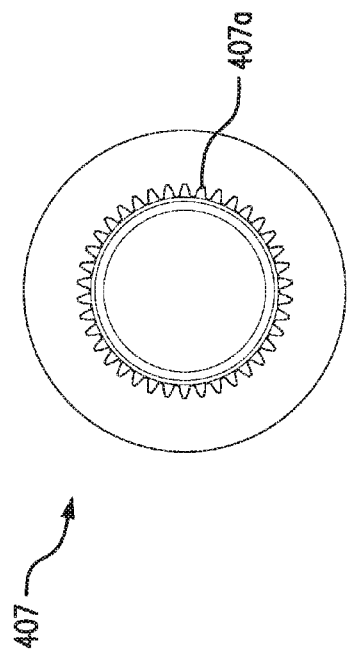
FIGS. 57A-57D provide perspective FIG. 57A, right FIG. 57B, left FIG. 57C, and front FIG. 57D views of the ring gear of the delivery system of FIG. 52.
Figure 57D:
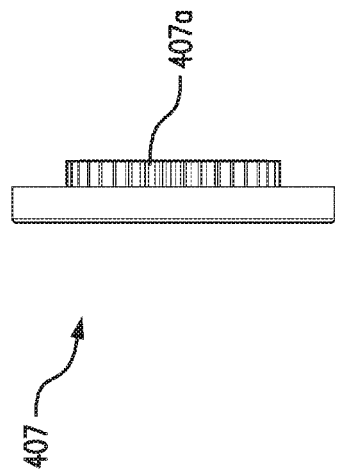
Figure 57A:
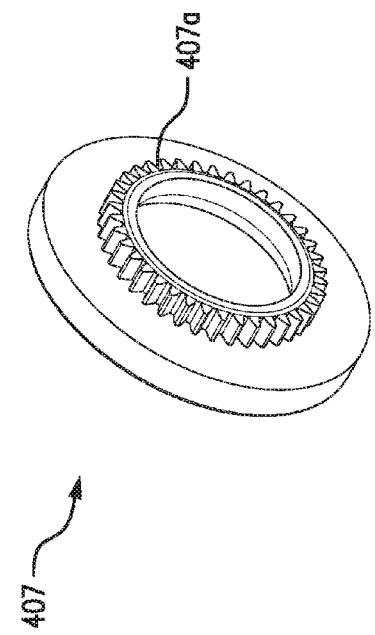
Figure 57C:
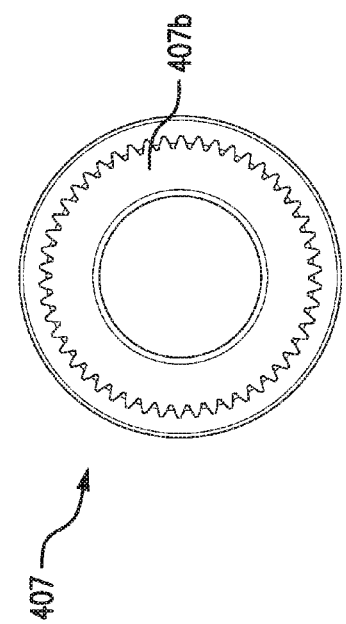
Figure 58A:
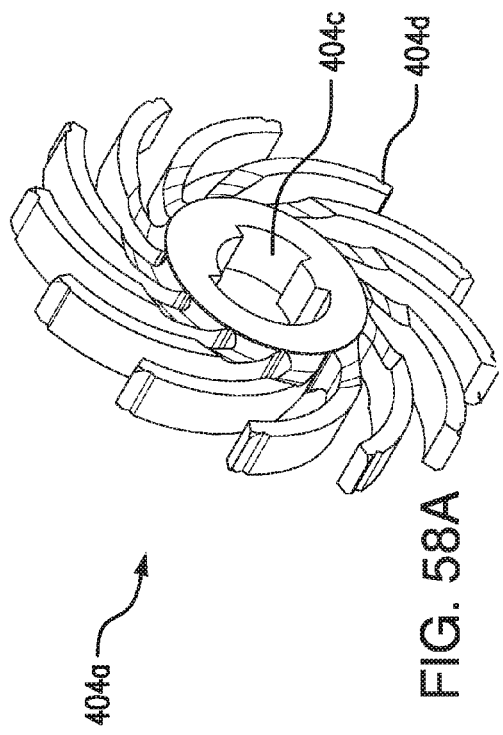
FIGS. 58A-58D provide perspective FIG. 58A, right FIG. 5813, left FIG. 58C, and front FIG. 58D views of the first clutch driver of the delivery system of FIG. 52.
Figure 58B:
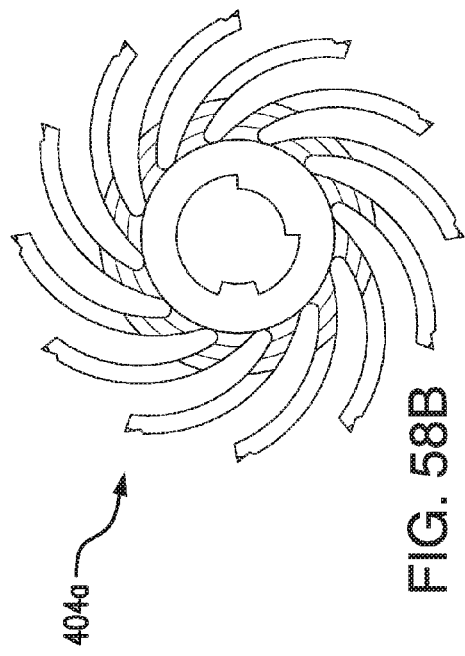
Figure 58C:
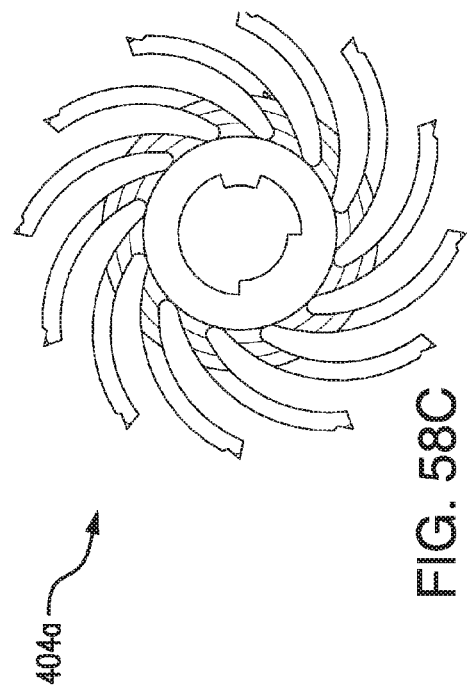
Figure 58D:
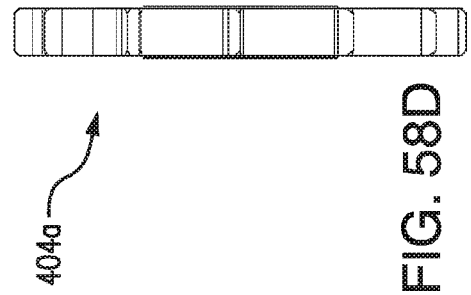
Figure 60A:
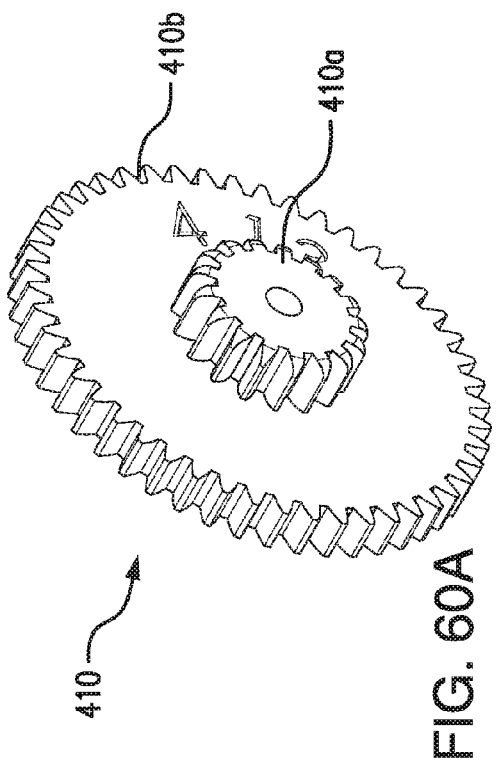
FIGS. 60A-60D provide perspective FIG. 60A, right FIG. 60B, left FIG. 60C, and front FIG. 60D views of the intermediate gear of the delivery system of FIG. 52.
Figure 60B:
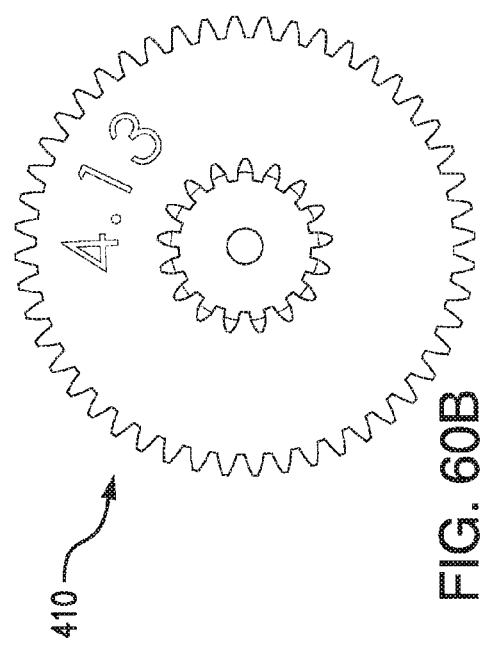
Figure 60C:
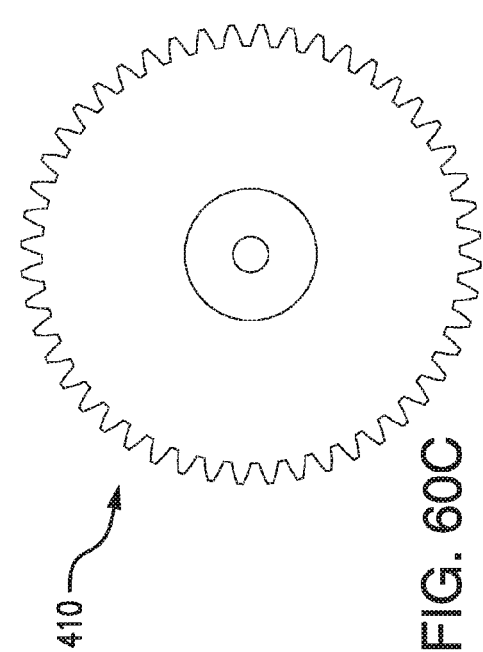
Figure 60D:
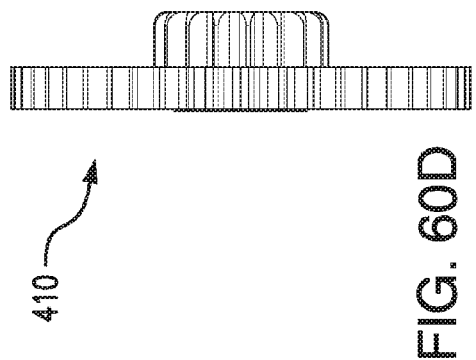

Referring to FIG. 36 for the purpose of illustration and not limitation, an exemplary embodiment of a system for delivering an implant is provided and designated generally by reference character 1002. Portions of this exemplary embodiment are depicted in FIGS. 37-45. Elements that are similar to the previously described embodiments have been given like numbers, and unless described otherwise, the element can include the same features as described above. The delivery system 1002 can be configured to deliver an implant in a similar manner as described hereinabove.

The delivery system 1002 can include a handle 201, an outer tubular member 222, an inner shaft member 221, and an implant 223, for example, a braided implant. The handle 201 can include a trigger 260 and an actuation assembly 202, which can be configured to move the inner shaft member 221 and the outer tubular member 222 relative to the handle 201 as described above upon deployment of the trigger 260 from the first position to the second position and return from the second position to the first position. The trigger 260 can include a lock as described herein above.

Referring now to FIGS. 37-45 for the purpose of illustration and not limitation, the actuation assembly 202 can include a planetary gear system as embodied in delivery system 1001. For example, the actuation assembly 202 can include a sun gear shaft 203 (which can include a sun gear portion 203a, a sheath pinion 203b, and a clutch engagement portion 203c; FIG. 39), a planet carrier 205 (which can include a circumferential pinion 205a, a clutch component 205b, and at least one pin 205c; FIG. 40), at least one planet gear 206, a ring gear 207 (which can include a circumferential pinion 207a and a ring gear portion 207b; FIG. 41), a first clutch driver 204a and a second clutch driver 204b, both identical in shape (each can include sun gear shaft engagement portion 204c and a clutch portion 204d; FIG. 42). The actuation assembly 202 can include a shuttle frame 209. The shuttle frame 209 can have the planet carrier 205, planet gears 206, sun gear shaft 203, ring gear 207, and first and second clutch drivers (204a and 204b) disposed thereon. The shuttle frame 209 can be disposed within the handle 201 and can be moveable relative to the handle 201 along the length of the handle 201. The shuttle frame 209 can include a clutch engagement portion 209a, a cavity 209b which can receive a ferrule coupled to the proximal end of the outer tubular member 222, and clips 209d and 209e, which can hold the planetary gear system in place on the shuttle frame 209. The planet carrier 205, planet gears 206, sun gear shaft 203 and ring gear 207 can perform as the respective elements of the planetary gear system as described above. The actuation assembly can also include a ratchet rack 208. The actuation assembly can be functionally coupled to the trigger 260 by a driving rack 212, which can be supported by the handle 201. The actuation assembly can include a clutch release 211 which can engage a stop 201d disposed on the handle, as described herein above with regard to system 1000.

During operation, the user can deploy the trigger 260 from the first position to the second position (referred to herein as the "first action"). The trigger 260 can cause the driving rack 212 to move in a proximal direction. The driving rack 212, functionally meshed with the circumferential pinion 207a of the ring gear 207, can impart rotational motion on the ring gear 207. The ring gear portion 207b of the ring gear 207 can be operatively meshed with the planet gears 106, and can impart rotational motion on the planet gears 206. The planet gears 206 can be constrained from rotating freely because they are operatively meshed with the sun gear portion 203a of the sun gear shaft 203. The movement of the planet gears 206, which are disposed on the pins 205c of the planet carrier 205, can impart rotational motion on the planet carrier 205. The planet carrier 205 and the sun gear shaft 203 can be rotationally coupled by the second clutch driver 204b when rotating in the first action; thus, rotation can be transmitted to the sun gear shaft 203 in a 1:1 ratio. The first clutch driver 204a can allow the sun gear shaft 203 to rotate freely relative to the shuttle frame 209 during the first action. The sheath pinion 203b of the sun gear shaft 203 can be meshed with the large spur gear 210a of an intermediate gear 210, and can impart rotational motion on the intermediate gear 210. The small spur gear 210b of the intermediate gear 210 can be operatively meshed with a rack 201c disposed on the second handle housing portion 201b; thus, the rotational motion of the intermediate gear 210 can impart linear motion on the shuttle frame 209 in the proximal direction. The outer tubular member 222, which can be fixedly coupled to the shuttle frame 209 can move proximally relative to the handle 201. The circumferential pinion 205a of the planet carrier 205 can be operatively meshed with a ratchet rack 208, and rotation of the planet carrier 205 can move the ratchet rack 208 distally. The inner shaft member 221, which can be fixedly coupled to the ratchet rack 208, moves distally. Thus, during the first action, the inner shaft member 221 can move distally relative to the handle 201 and the outer tubular member 222 can move proximally relative to the handle 101.

Upon return of the trigger 260 from the second position to the first position (herein referred to as the "second action"), the driving rack 212 can move distally relative to the handle 201. The driving rack 212 can impart rotational motion on the ring gear 207. The ring gear 207 can impart rotational motion on the three planet gears 206. The planet gears 206 can rotate about the sun gear shaft 203, which can be held stationary relative the shuttle frame 209 via the first clutch driver 204a. The planet gears 106 can impart rotational motion on the planet carrier 205. Linear motion in the proximal direction can be transmitted to the ratchet rack 208 by the planet carrier 205. The inner shaft member 221, fixedly coupled to the ratchet rack 208, can move proximally relative to the handle 201. Thus, during the second action, the inner shaft member 221 can move proximally relative to the handle 201 and the outer tubular member 222 can be stationary relative to the handle 201.

Referring to FIG. 46 for the purpose of illustration and not limitation, an exemplary embodiment of a system for delivering an implant is provided and designated generally by reference character 1003. Portion of this exemplary embodiment are depicted in FIGS. 47-51. Elements that are similar to the previously described embodiments have been given like number, and unless described otherwise, the elements can include the same features as described above.

The delivery system 1003 can include a handle 301, an outer tubular member 322, an inner shaft member 321, and an implant 323, for example, a braided implant. The handle 301 can include a trigger 360 and an actuation assembly 302, which can be configured to move the inner shaft member 321 and the outer tubular member 322 relative to the handle 301 as described above upon deployment of the trigger 360 from the first position to the second position and return from the second position to the first position. The trigger 360 can include a lock as described herein above.

Referring now to FIGS. 47-51 for the purpose of illustration and not limitation, the actuation assembly 302 can include a planetary gear system as embodied in delivery system 1001. For example, the actuation assembly 302 can include a sun gear shaft 303 (which can include a sun gear portion 303a, a sheath pinion 303b, and a clutch engagement portion 303e; FIG. 47), a planet carrier 305 (which can include a circumferential pinion 305a, a clutch component 305b, and a least one pin 305c; FIG. 48), at least one planet gear 306, a ring gear 307 (which can include a circumferential pinion 307a and a ring gear portion 307b; FIG. 49), a first clutch driver 304a and a second clutch driver 304b, both identical in shape (each can include including a sun gear shaft engagement portion 304c and a clutch portion 304d; FIG. 50). The actuation assembly 302 can include a shuttle frame 309. The shuttle frame 309 can have the planet carrier 305, planet gears 306, sun gear shaft 303, ring gear 307, and first and second clutch drivers 304a, 304b disposed thereon. The shuttle frame 309 can be disposed within the handle 301 and can be moveable relative to the handle 301 along the length of the handle 301. The shuttle frame 309 can include clips 309d and 309e, which can hold the planetary gear system in place on the shuttle frame 309. The planet carrier 305, planet gears 306, sun gear shaft 303, and ring gear 307 can perform as the respective elements of the planetary gear system as described above. The actuation assembly can also include a ratchet rack 308. The actuation assembly can be functionally coupled to the trigger 360 by a driving rack 312, which can be supported by the handle 301.

During operation, the user can deploy the trigger 360 from the first position to the second position (referred to herein as the "first action"). The trigger 360 can cause the driving rack 312 to move in a proximal direction. The driving rack 312, functionally meshed with the circumferential pinion 307a of the ring gear 307, can impart rotational motion on the ring gear 307. The ring gear portion 307b of the ring gear 307 can be operatively meshed with the planet gears 306, and can impart rotational motion on the planet gears 306. The planet gears 306 can be constrained from rotating freely because they are operatively meshed with the sun gear portion 303a of the sun gear shaft 303. The movement of the planet gears 306, which are disposed on the pins 305c of the planet carrier 305, can impart rotational motion on the planet carrier 305. The planet carrier 305 and the sun gear shaft 303 are rotationally coupled by the second clutch driver 304b when rotating in the first action; thus, rotation can be transmitted to the sun gear shaft 303 in a 1:1 ratio. The first clutch driver 304a allows the sun gear shaft 303 to rotate freely relative to the shuttle frame 309 during the first action. The sheath pinion 303b of the sun gear shaft 303 can be meshed a rack 301c disposed on the second handle housing portion 301b; thus, the rotational motion of the sun gear shaft 303 can impart linear motion on the shuttle frame 309 in the proximal direction. The outer tubular member 322, which can be fixedly coupled to the shuttle frame 309 can move proximally relative to the handle 301. The circumferential pinion 305a of the planet carrier 305 can be operatively meshed with a ratchet rack 308, and rotation of the planet carrier 305 can move the ratchet rack 308 distally. The inner shaft member 321, which can be fixedly coupled to the ratchet rack 308, moves distally. Thus, during the first action, the inner shaft member 321 can move distally relative to the handle 301 and the outer tubular member 322 can move proximally relative to the handle 301.

Upon return of the trigger 360 from the second position to the first position (herein referred to as the "second action"), the driving rack 312 can move distally relative to the handle 301. The driving rack 312 can impart rotational motion on the ring gear 307. The ring gear 307 can impart rotational motion on the three planet gears 306. The planet gears 306 can rotate about the sun gear shaft 303, which can be held stationary relative to the shuttle frame 309 via the first clutch driver 304a. The planet gears 306 can impart rotational motion on the planet carrier 305. Linear motion can be transmitted to the ratchet rack 308 by the planet carrier 305. The inner shaft member 321 can move proximally relative to the handle 301. Thus, during the second action, the inner shaft member 321 can move proximally relative to the handle 301 and the outer tubular member 322 can be stationary relative to the handle 301.

Referring now to FIG. 52 for the purpose of illustration and not limitation, an exemplary embodiment of a system for delivering an implant is provided and designated generally by reference character 1004. Portions of this exemplary embodiment are depicted in FIGS. 53-61. Elements that are similar to the previously described embodiment have been given like numbers. The delivery system 1004 can be configured to deliver an implant in a similar manner as described herein above.

The delivery system 1004 can include a handle 401, an outer tubular member 422, an inner shaft member 421, and an implant 423, for example, a braided implant. The handle 401 can include a trigger 460 and an actuation assembly 402, which can be configured to move the inner shaft member 421 and the outer tubular member 422 relative to the handle 401 as described above upon deployment of the trigger 460 from the first position to the second position and return from the second position to the first position. The trigger 460 can include a lock as described herein above.

Referring now to FIGS. 53-61 for the purpose of illustration and not limitation, the actuation assembly 402 can include a planetary gear system as embodied in delivery system 1000. For example, the actuation assembly 402 can include a sun gear shaft 403 (which can include a sun gear portion 403a, a sheath pinion 403b, and a clutch engagement portion 403c; FIG. 55), a planet carrier 405 (which can include a circumferential pinion 405a, a clutch component 405b, and at least one pin 405c; FIG. 56), at least one planet gear 406, a ring gear 407 (which can include a circumferential pinion 407a and a ring gear portion 407b; FIG. 57), a first clutch driver 404a and a second clutch driver 404b, both identical in shape (each can include including a sun gear shaft engagement portion 404c and a clutch portion 404d; FIG. 58). The actuation assembly 402 can include a shuttle frame 409. The shuttle frame 409 can have the planet carrier 405, planet gears 406, sun gear shaft 403, ring gear 407, and first and second clutch drivers (404a and 404b) disposed thereon. The shuttle frame 409 can be disposed within the handle 401 and can be moveable relative to the handle 401 along the length of the handle 401. The shuttle frame 409 can include a clutch engagement portion 409a, a cavity 409b, which can receive a ferrule coupled to the proximal end of the outer tubular member 422, and a guide 409c. The actuation assembly 402, can include a plate 414 disposed on the shuttle assembly 409. The plate 414 can hold portions of the actuation assembly 402 in place and can protect the actuation assembly 402. The actuation assembly 402 can include at least one pin 413 configured to engage at least one pin track disposed within the handle 401 to thereby guide the shuttle frame 409 along the handle. The at least one pin can include a first pin 413a disposed through an axis of the sun gear shaft 403. The actuation assembly can include a second pin 413b and a third pin 413c, each disposed through the plate 414 and the shuttle frame 409. The second pin 413b and third pin 413c can hold the plate 414 in place on the shuttle frame 409. The actuation assembly 402 can include a fourth pin 413d disposed through an axis of the intermediate gear 410. The fourth pin 413d can engage the handle to guide the actuation assembly 402 as it moves relative to the handle 401. The actuation assembly can be functionally coupled to the trigger 460 by a driving rack 412, which can be supported in the guide 409c. The actuation assembly can include a clutch release 411 which can engage a stop 401d disposed on the handle, as described herein above with regard to system 1000.

During operation, the user can deploy the trigger 460 from the first position to the second position (referred to herein as the "first action"). The trigger 640 can cause the driving rack 412 to move in the distal direction. The driving rack 412, functionally meshed with the circumferential pinion 405a of the planet carrier 405, can impart rotational motion on the planet carrier 405. The planet carrier 405 can impart rotational motion on the three planet gears 406. The planet gears 406 can be constrained from rotating freely because they can be meshed with the sun gear portion 403a of the sun gear shaft 403. The three planet gears 406 can be meshed with the ring gear portion 407b of the ring gear 407, and can impart rotational motion on the ring gear 407. The ring gear 407, which can be meshed with the ratchet rack 408, and can drive the ratchet rack 408 distally. The inner shaft member 421, which can be fixedly coupled to the ratchet rack 408, moves distally. The planet carrier 405 can be rotationally coupled to the sun gear shaft 403 by the second clutch driver 404b when rotating in the first action; thus, rotation can be transmitted to the sun gear shaft 403 in a 1:1 ratio. The first clutch driver 404a can allow the sun gear shaft 403 to rotate freely relative to the shuttle frame 409 during the first action. The sheath pinion 403b of the sun gear shaft 403 can be meshed with the large spur gear 410a of the intermediate gear 410, and can impart rotational motion on the intermediate gear 410. The small spur gear 410b of the intermediate gear 410 can be operatively meshed with a rack 401c disposed on the second handle housing portion 401b; thus, the rotational motion of the intermediate gear 410 can impart linear motion on the shuttle frame 409 in the proximal direction. The outer tubular member 422, which can be fixedly coupled to the shuttle frame 409, can move proximally relative to the handle. Thus, during the first action, the inner shaft member 421 can move distally relative to the handle 401 and the outer tubular member 422 can move proximally relative to the handle 401.

Upon return of the trigger 460 from the second position to the first position (herein referred to as the "second action"), the driving rack 412 can move proximally relative to the handle 401. The driving rack 412 can impart rotational motion to the planet carrier 405. The planet carrier 405 can transmit rotational motion to the three planet gears 406. The planet gears 406 can rotate about the sun gear shaft. 403, which can be held stationary relative the shuttle frame 409 via the first clutch driver 404a. The planet gears 406 can impart rotary motion to the ring gear 407. Linear motion can be transmitted to the ratchet rack 408 in the proximal direction by the ring gear 407. The inner shaft member 421, which can be fixedly coupled to the ratchet rack 408, can move proximally relative to the handle 401. Thus, during the second action, the inner shaft member moves proximally relative to the handle 401 and the outer tubular member 422 can be stationary relative to the handle.

Figure 62:
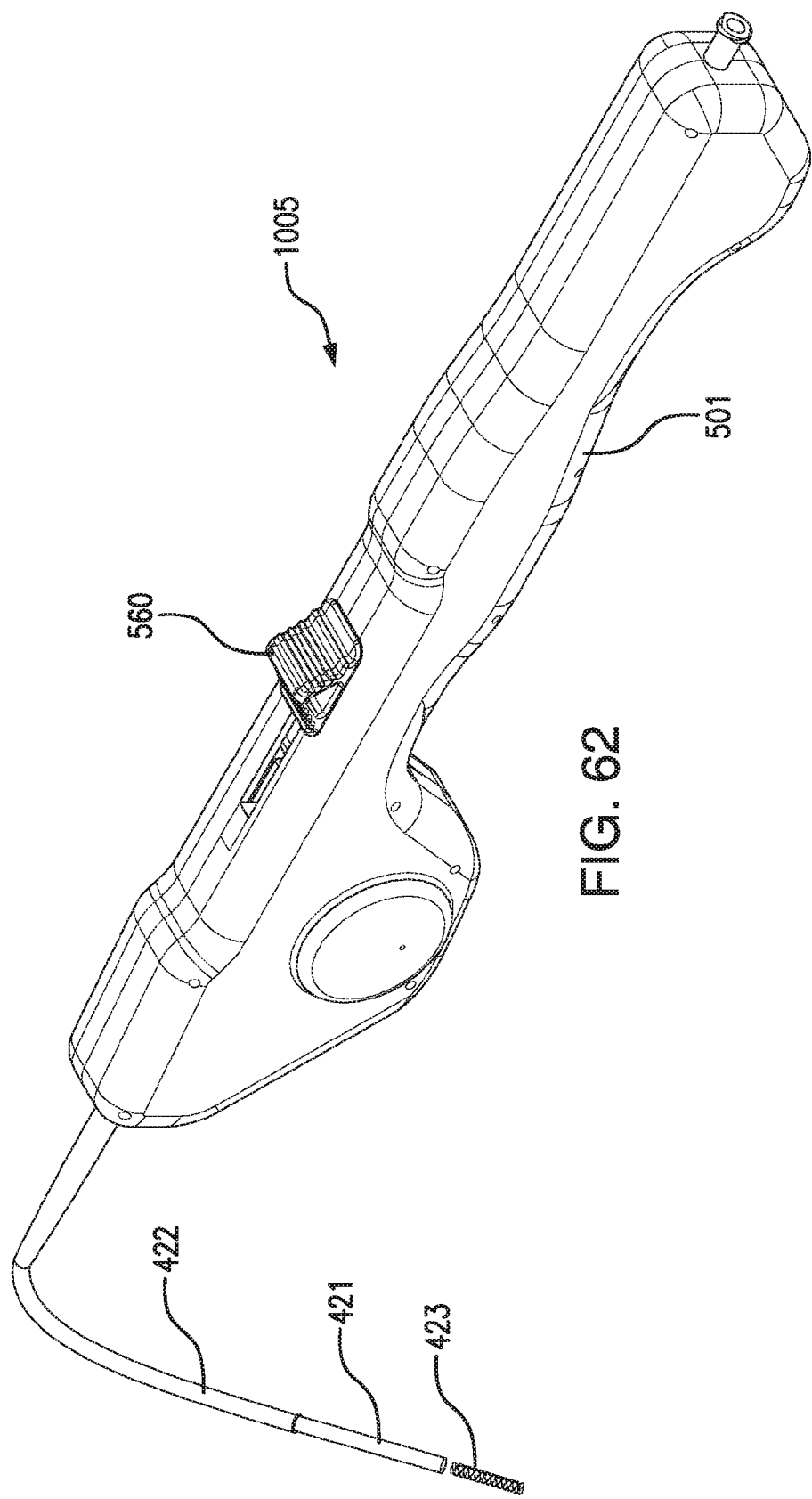
FIG. 62 is a perspective view of a further exemplary embodiment of a delivery system in accordance with the disclosed subject matter.
Figure 63:
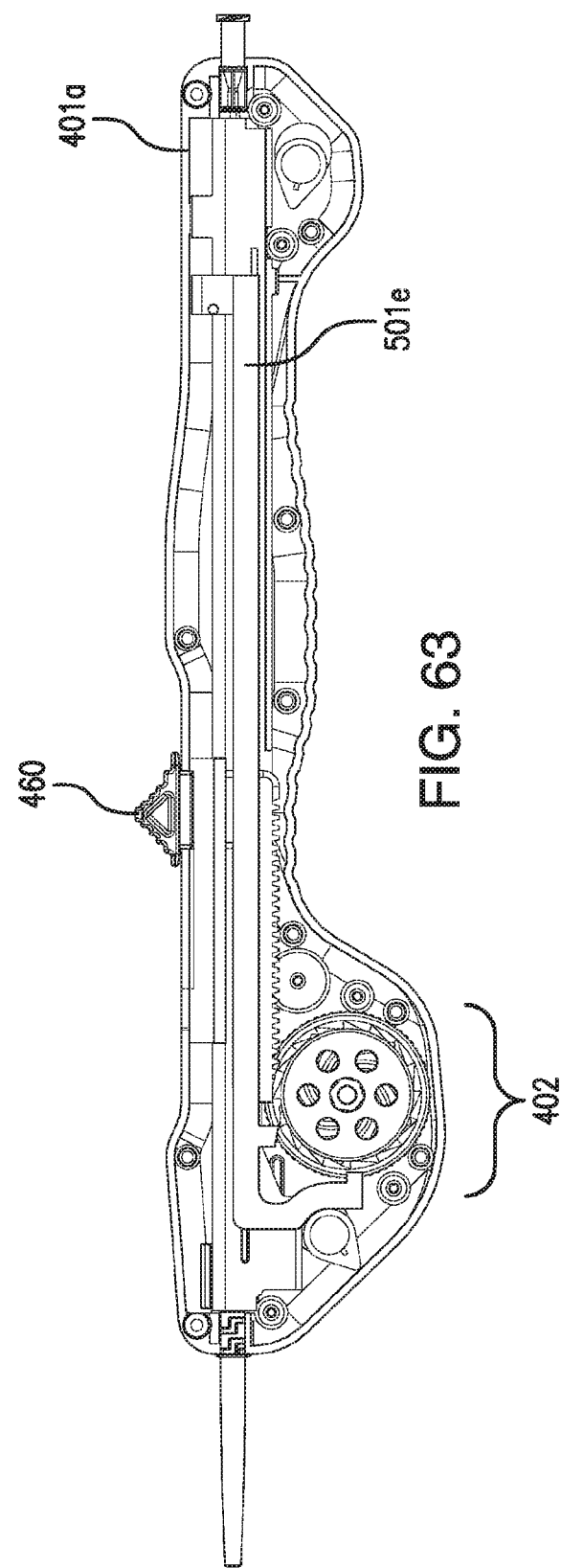
FIG. 63 is a right side view, with a portion of the handle housing removed, of the delivery system of FIG. 62.
Figure 64:
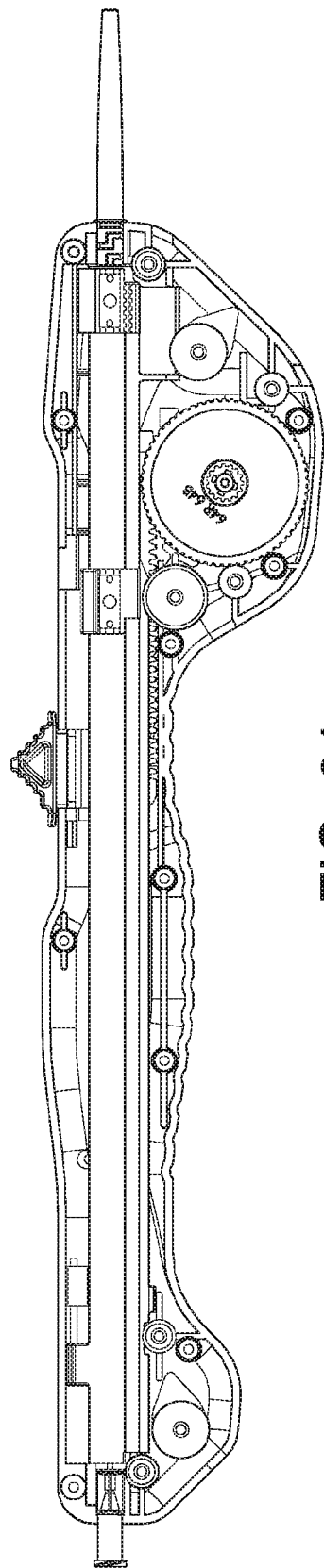
FIG. 64 is a left side view, with a portion of the handle housing removed, of the delivery system of FIG. 62.
Figure 66A:
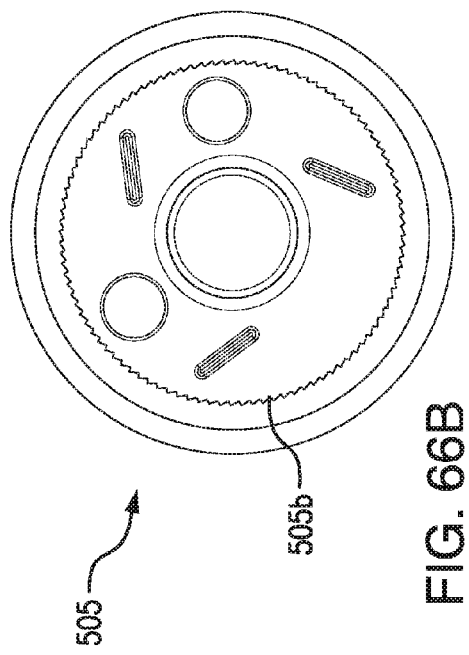
FIGS. 66A-66D provide perspective FIG. 66A, right FIG. 66B, left FIG. 66C, and front FIG. 66D views of the planet carrier of the delivery system of FIG. 62.
Figure 66B:
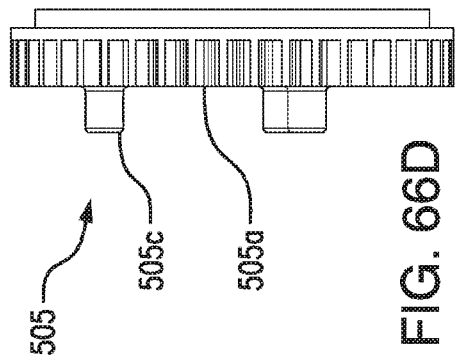
Figure 66C:
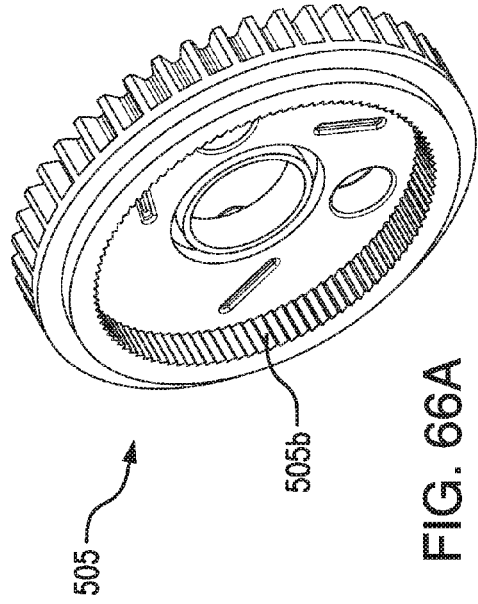
Figure 66D:
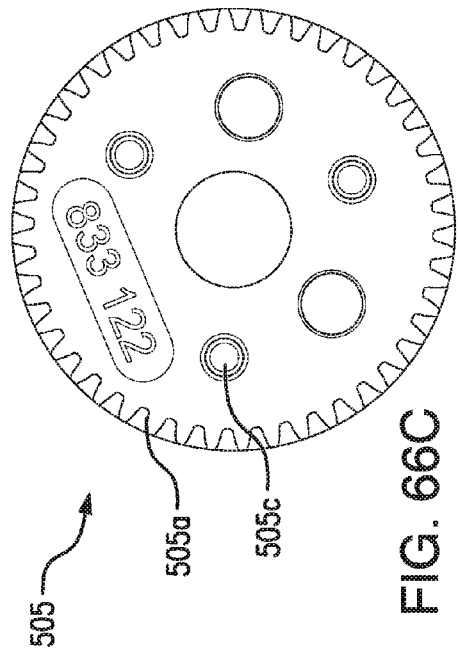
Figure 67B:
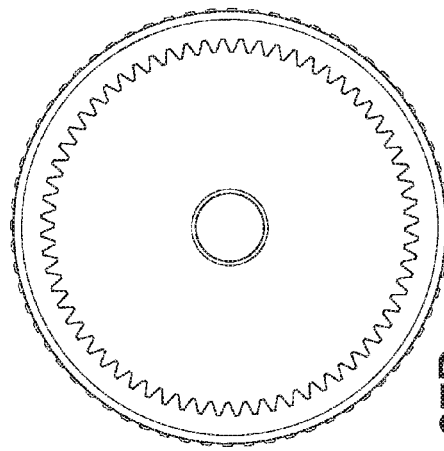
FIGS. 67A-67D provide perspective FIG. 67A, right FIG. 67B, left FIG. 67C, and front FIG. 67D views of the ring gear of the delivery system of FIG. 62.
Figure 67D:
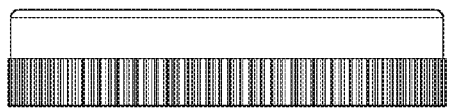
Figure 67A:
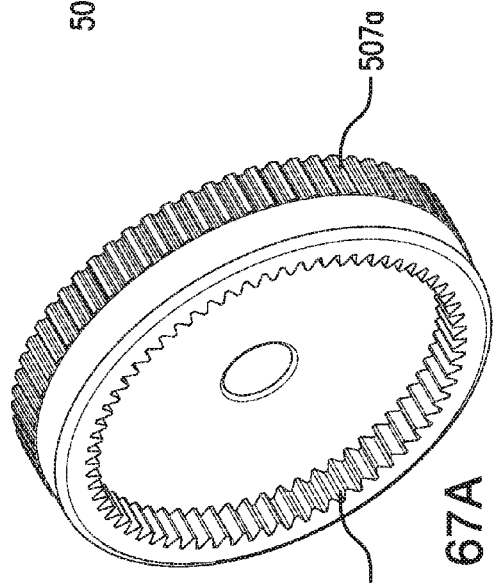
Figure 67C:
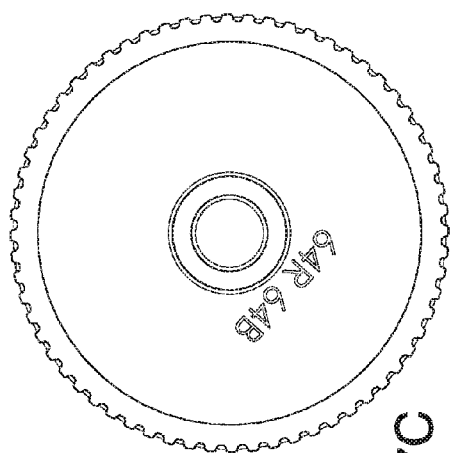
Figure 69B:
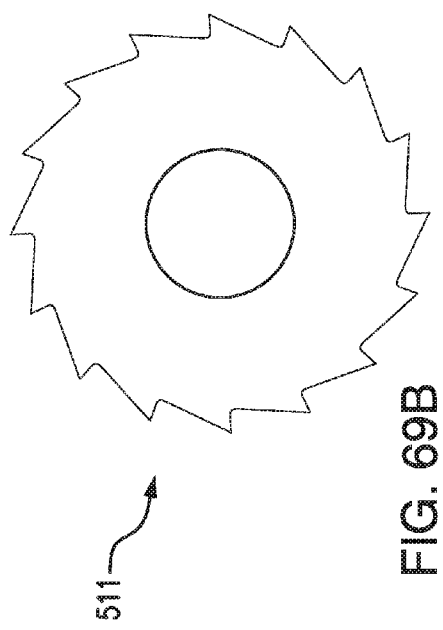
FIGS. 69A-69D provide perspective FIG. 69A, right FIG. 69B, left FIG. 69C, and front FIG. 69D views of the clutch release of the delivery system of FIG. 62.
Figure 69D:
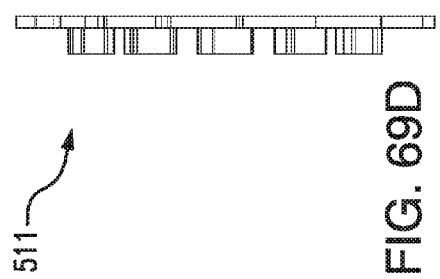
Figure 69A:
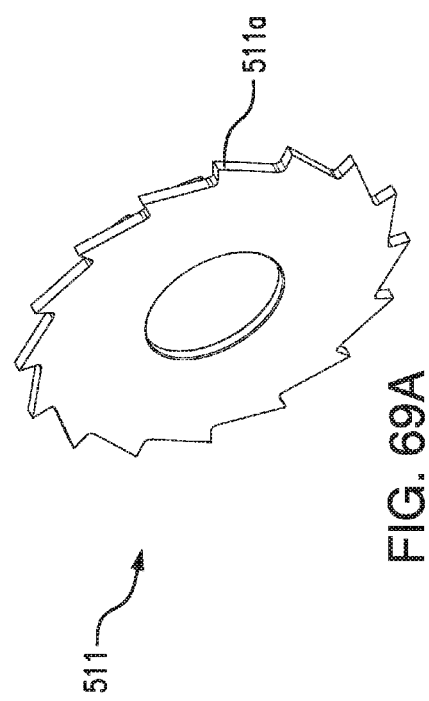
Figure 69C:
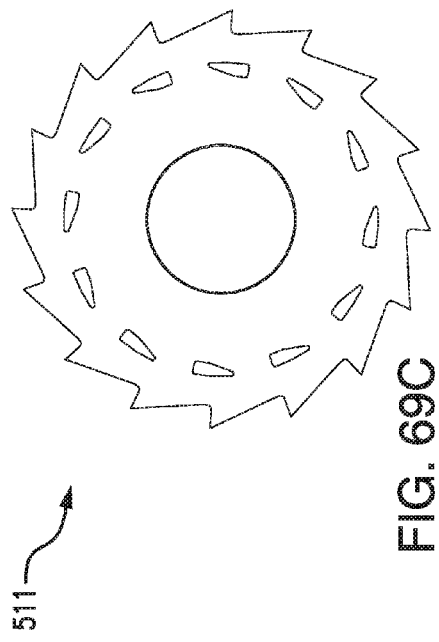
Figure 71B:
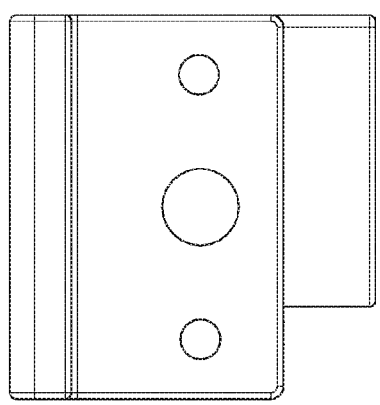
FIGS. 71A-71D provide perspective FIG. 71A, right FIG. 71B, left FIG. 71C, and front FIG. 71D views of the sheath gondola of the delivery system of FIG. 62.
Figure 71D:
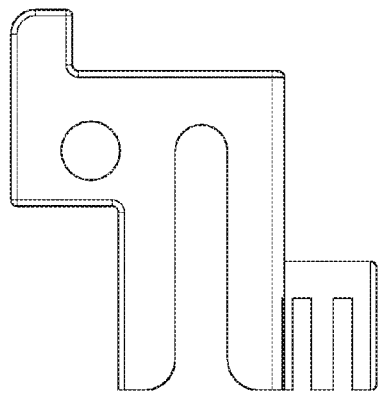
Figure 71A:
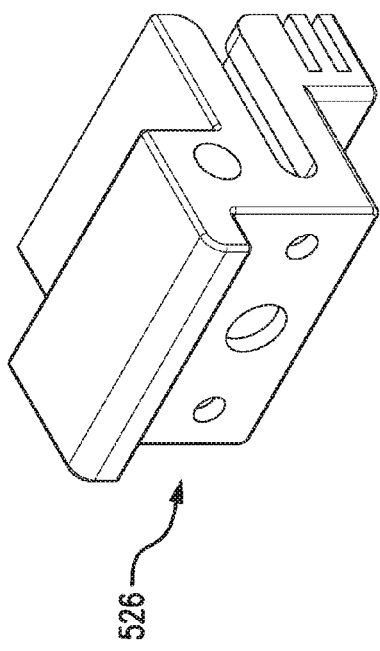
Figure 71C:
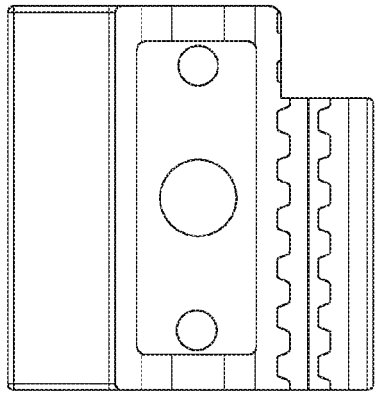
Figure 72B:
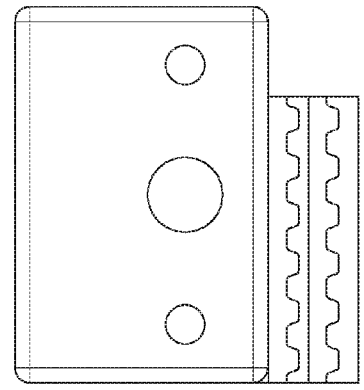
FIGS. 72A-72D provide perspective FIG. 72A, right FIG. 72B, left FIG. 72C, and front FIG. 72C views of the ratchet gondola of the delivery system of FIG. 62.
Figure 72D:
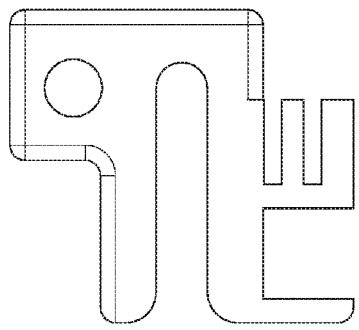
Figure 72A:
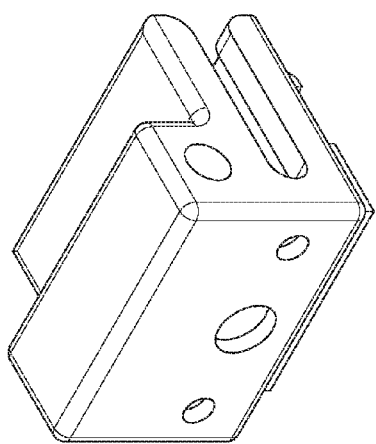
Figure 72C:
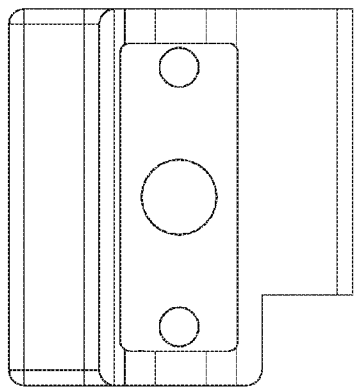
Figure 73A:
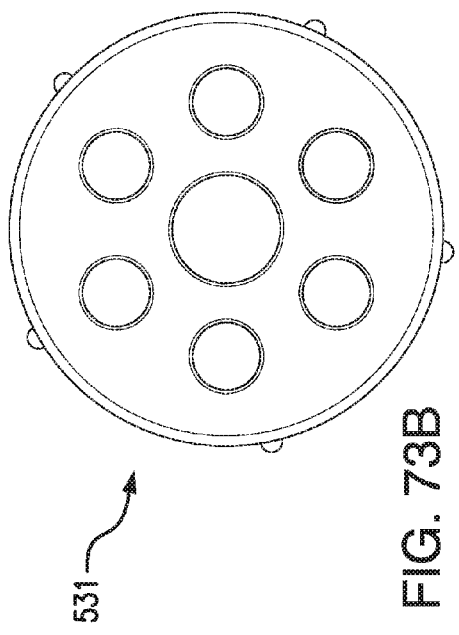
FIGS. 73A-73D provide perspective FIG. 73A, right FIG. 73B, left FIG. 73C, and front FIG. 73D views of the clutch ring of the delivery system of FIG. 62.
Figure 73D:
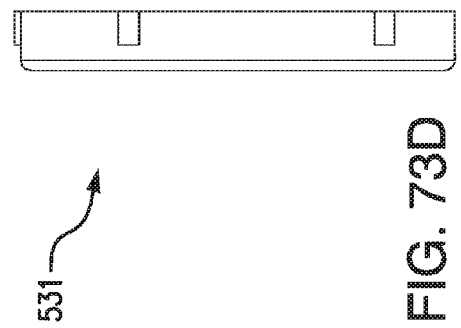
Figure 73B:
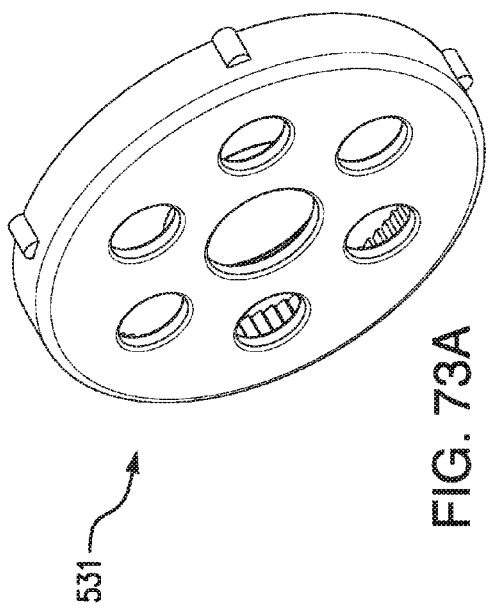
Figure 73C:
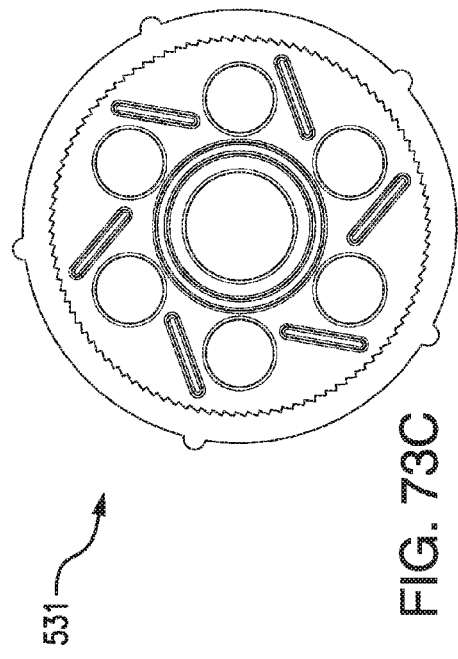
Figure 74:
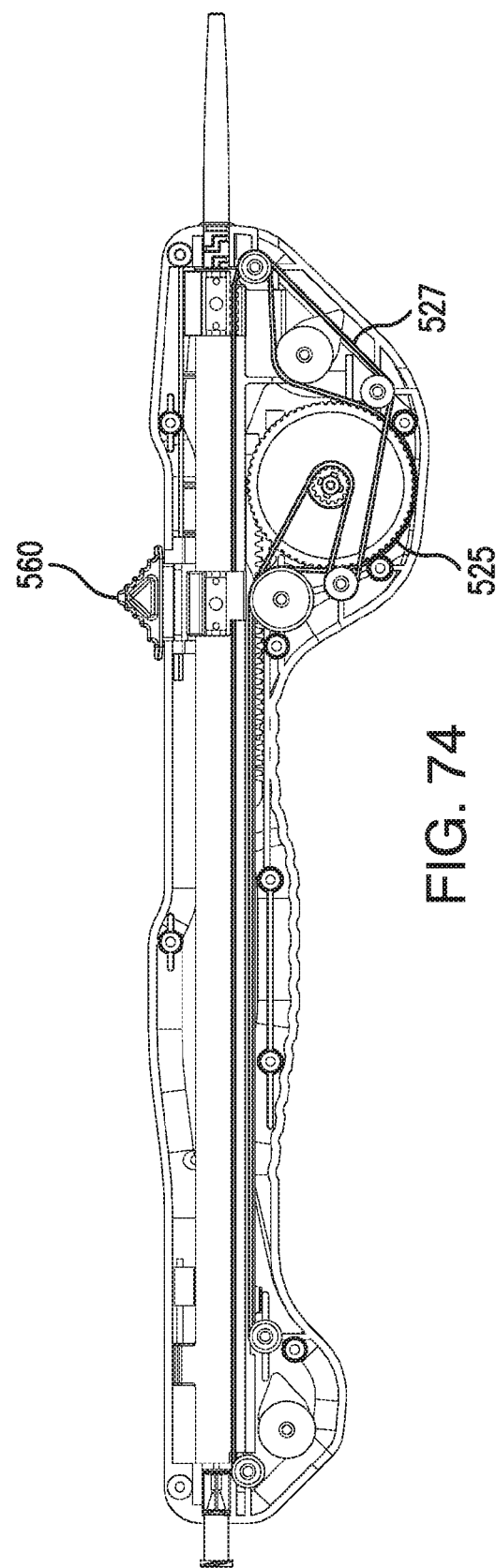
FIG. 74 is a left side view, with a portion of the handle housing removed, of the delivery system of FIG. 62.
Figure 75:
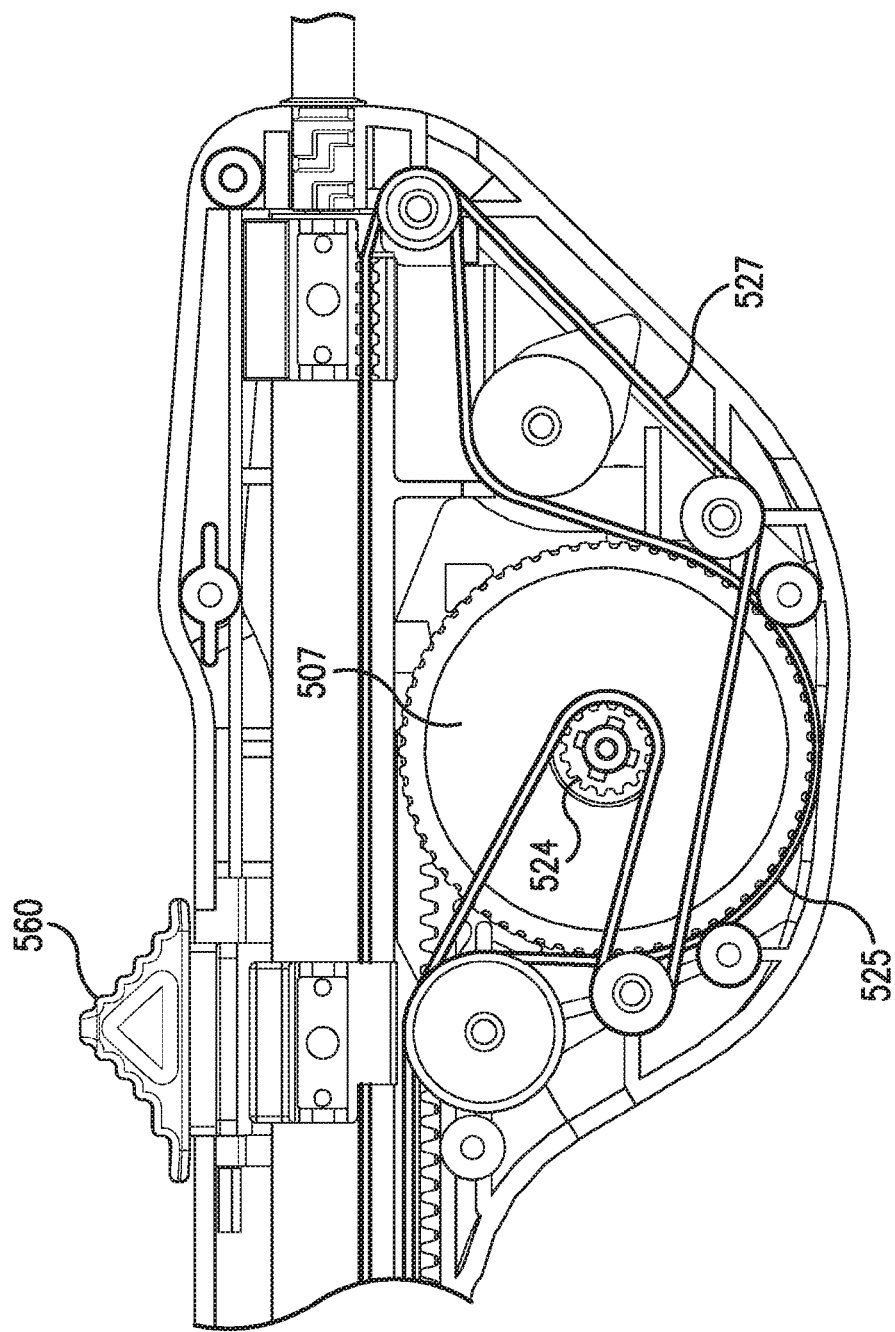
FIG. 75 is an enlarged in view of a portion of the delivery system of FIG. 62.

Referring to FIG. 62 for the purpose of illustration and not limitation, an exemplary embodiment of a system for delivering an implant is provided and designated generally by reference character 1005. Portions of this exemplary embodiment are depicted in FIGS. 63-75. Elements that are similar to the previously described embodiment have been given like numbers. The delivery system 1005 can be configured to deliver an implant in a similar manner as described herein above.

The delivery system 1005 can include a handle 501, an outer tubular member 522, an inner shaft member 521, and an implant 523, for example, a braided implant. The handle 501 can include a trigger 560 and an actuation assembly 502, which can be configured to move the inner shaft member 521 and the outer tubular member 522 relative to the handle 501 as described above upon deployment of the trigger 560 from the first position to the second position and return from the second position to the first position. The trigger 560 can include a lock as described herein above.

Referring now to FIGS. 63-75 for the purpose of illustration and not limitation, the actuation assembly 502 can include a planetary gear system similar to the planetary gear system disclosed in system 1000. In lieu of a shuttle frame and a ratchet rack coupled to the outer tubular member and inner shaft member, respectively, the system 1005 can include gondolas disposed on tension elements, as described further below.

For example, the actuation assembly 502 can include a sun gear shaft 503 (which can include a sun gear portion 503a, a clutch engagement portion 503c, and a sheath gear engagement portion 503d; FIG. 65), a planet carrier 505 (which can include a circumferential pinion 505a, a clutch component 505b, and at least one pin 505c; FIG. 66), at least one planet gear 456, a ring gear 507 (which can include a circumferential pinion 507a and a ring gear portion 507b; FIG. 67), a first clutch driver 404a and a second clutch driver 404b, both identical in shape (each can include including a sun gear shaft engagement portion 504c and a clutch portion 504d; FIG. 68). The actuation assembly can include a sheath gear 524, which can engage the sheath gear engagement portion 503d of the sun gear shaft 503. The actuation assembly can include a first tension element 525, and a sheath gondola 526 disposed on the first tension element. The first tension element can be functionally coupled to the sheath gear 524. The sheath gondola 526 can be fixedly coupled to the outer tubular member 522. The actuation assembly can include a second tension element 527, and a ratchet gondola 528 disposed on the second tension element. The second tension element 527 can be functionally coupled to the circumferential pinion 507a of the ring gear 507. The ratchet gondola 528 can be fixedly attached the inner shaft member 521. The actuation assembly can include a clutch ring 531, which can be fixedly placed within the handle 501 and can provide a clutch engagement portion for the first clutch driver 501a. Alternatively, the handle 501 can include a clutch engagement portion to engage the first clutch driver 501a. The system can further include a plurality of pulley elements 529, which can be used to guide the first and second tension elements, and at least two tensioners 530a, 530b, which can be used to achieve the desired tension in the first and second tension elements. The actuation assembly can be functionally coupled to the trigger 560 by a driving rack 512. The actuation assembly can include a clutch release 511 which can engage a stop 501e disposed within the handle, and configured to engage the clutch release 511 when the sheath gondola has moved the stop 501e into place.

During operation, the user can deploy the trigger 560 from the first position to the second position (referred to herein as the "first action"). The trigger 540 can cause the driving rack 512 to move in the distal direction. The driving rack 512, functionally meshed with the circumferential pinion 505a of the planet carrier 505, can impart rotational motion on the planet carrier 505. The planet carrier 505 can impart rotational motion on the three planet gears 506. The planet gears 506 can be constrained from rotating freely because they can be meshed with the sun gear portion 503a of the sun gear shaft 503. The three planet gears 506 can be meshed with the ring gear portion 507b of the ring gear 507, and can impart rotational motion on the ring gear 407. The ring gear 507, which can be functionally coupled to the ratchet gondola 528 by the second tension element 527, can cause the ratchet gondola 528 to move distally. The inner shaft member 521, which can be fixedly coupled to the ratchet gondola 528, can move distally. The planet carrier 505 can be rotationally coupled to the sun gear shaft 503 by the second clutch driver 504b when rotating in the first action; thus, rotation can be transmitted to the sun gear shaft 503 in a 1:1 ratio. The first clutch driver 504a can allow the sun gear shaft 503 to rotate freely relative to the clutch ring 531 during the first action. The sheath gear engagement portion 503d of the sun gear shaft 503 can functionally engage the sheath gear 524, and can impart rotational motion on sheath gear 524. The sheath gear 524, which can be functionally coupled to the sheath gondola 526 by the first tension element 525, can cause the sheath gondola 526 to move proximally. The outer tubular member 522, which can be fixedly coupled to the sheath gondola 526, can move proximally relative to the handle. Thus, during the first action, the inner shaft member 521 can move distally relative to the handle 501 and the outer tubular member 522 can move proximally relative to the handle 501.

Upon return of the trigger 560 from the second position to the first position (herein referred to as the "second action"), the driving rack 512 can move proximally relative to the handle 501. The driving rack 512 can impart rotational motion to the planet carrier 505. The planet carrier 505 can transmit rotational motion to the three planet gears 506. The planet gears 506 can rotate about the sun gear shaft 503, which can be held stationary relative the clutch ring 531 via the first clutch driver 504a. The planet gears 506 can impart rotary motion to the ring gear 507. The ring gear 507 can drive the ratchet gondola 528 proximally via the second tension element 527. The inner shaft member 521, which can be fixedly coupled to the ratchet gondola 528, can move proximally relative to the handle 501. Thus, during the second action, the inner shaft member can move proximally relative to the handle 501 and the outer tubular member 422 can be stationary relative to the handle.

The embodiments described above can be formed of any suitable materials, for example, the handle and actuation assembly elements can be made from plastic, composites, or metal. As an example, and not by way of limitation, the gears, (for example, the sun gear shaft, planet carrier, planet gears, intermediate gear and ring gear), clutch drivers, shuttle frame, driving rack, and clutch release can be formed by silicon impregnated poly oxymethylene or acetal (e.g., DelRin® sold by DuPont). The ratchet rack can be made of TOPAS. The various pins and springs can be formed from plastic, metal (e.g., stainless steel or aluminum), or music wire. The plate can be formed from plastic or metal. The handle housing portion can be made from glass filled plastics or other plastic resins, for example ADS, polycarbonate, or an ADS polycarbonate blend. A rubber overmold can be used for grip and aesthetics, for example, on the trigger and the handle body. The strain relief can be a soft plastic, for example, polyethylene. The trigger and related elements can be formed by silicon impregnated poly oxymethylene or acetal (e.g., DelRin® sold by DuPont).

While the disclosed subject matter is described herein in terms of certain preferred embodiments for purpose of illustration and not limitation, those skilled in the art will recognize that various modifications and improvements can be made to the disclosed subject matter without departing from the scope thereof. Moreover, although individual features of one embodiment of the disclosed subject matter can be discussed herein or shown in the drawings of one embodiment and not in other embodiments, it should be readily apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

The following Applications, which are filed on the same day as this application, are incorporated by reference in their entirety: U.S. patent application Ser. No. 14/932,875; U.S. patent application Ser. No. 14/932,862; U.S. patent application Ser. No. 14/932,884; U.S. patent application Ser. No. 14/932,795; U.S. patent application Ser. No. 14/932,805; U.S. patent application Ser. No. 14/932,830; U.S. patent application Ser. No. 14/932,900; PCT Application No. PCT/US2015/059070; PCT Application No. PCT/US2015/059074; and PCT Application No. PCT/US2015/059084.

Furthermore, it is recognized that the actuation assembly and delivery system as disclosed herein can be used in a method of delivering an implant. That is, for purpose of illustration, such method would include providing a delivery system as disclosed herein, positioning the distal end portion of the outer tubular member proximate a desired site, and deploying the delivery system to push the implant from the outer tubular member to the desired site.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A system for delivering an implant, the implant to be disposed within a distal end portion of an outer tubular member and positioned to be engaged by a distal end portion of an inner shaft member when the inner shaft member is moved distally relative to the outer tubular member, the inner shaft member being disposed within the outer tubular member and movable distally and proximally relative to the outer tubular member, comprising:
a handle;
a trigger operatively coupled to the handle; and
an actuation assembly operatively coupled to the trigger, the inner shaft member, and the outer tubular member, the actuation assembly having:
a planet carrier;
at least one planet gear operatively coupled to the planet carrier,
a sun gear shaft operatively engaged with the planet gear,
a ring gear operatively engaged with the planet gear,
a first clutch driver configured to limit the sun gear shaft to uni-directional rotational motion, and
a second clutch driver configured to uni-directionally lock the sun gear shaft and the planet carrier;
wherein the actuation assembly is configured to displace the outer tubular member in the proximal direction a distance (d) relative to the handle and to separately move the inner shaft member distally a distance (x) relative to the handle upon deployment of the trigger from a first position to a second position, and further wherein the actuation assembly is configured to move the inner shaft member proximally a distance (y) relative to the handle with no displacement of the outer tubular member relative to the handle upon return of the trigger from the second position to the first position.

2. The system of claim 1, wherein the second clutch driver is configured to uni-directionally lock the sun gear shaft and the planet carrier such that the sun gear shaft, planet carrier and the ring gear have a 1:1 ratio of rotation during deployment of the trigger from the first position to the second position.

3. The system of claim 2, wherein the actuation assembly further comprises a clutch release operatively coupled to the second clutch driver and configured to prevent the second clutch driver from uni-directionally locking the sun gear shaft and the planet carrier when the clutch release is engaged by a stop.

4. The system of claim 3, wherein the stop is disposed on the handle, and the stop engages the clutch release when the actuation assembly has moved proximally a distance (z) along the handle.

5. The system of claim 3, wherein the clutch release comprises a saw-tooth portion and wherein the stop comprises a resilient abutment portion, and wherein the resilient abutment portion of the stop engages the saw-tooth portion of the clutch release when the actuation assembly has moved proximally a distance (z) along the handle.

6. The system of claim 1, wherein the first clutch driver is configured to limit the sun gear shaft to uni-directional motion such that the sun gear shaft does not rotate during return of the trigger from the second position to the first position and the planetary gear rotates about the sun gear shaft.

7. The system of claim 6, wherein the sun gear shaft is functionally coupled to the outer tubular member such that upon deployment of the trigger from the first position to the second position the sun gear shaft rotates and thereby causes the outer tubular member to move proximally.

8. The system of claim 6, wherein the actuation assembly further comprises a shuttle frame having the planet carrier, planet gear, sun gear shaft, ring gear, first clutch driver and second clutch driver disposed thereon.

9. The system of claim 8, wherein the shuttle frame is fixedly coupled to the outer tubular member.

10. The system of claim 9, wherein the sun gear shaft is functionally coupled to the handle such that upon deployment of the trigger from the first position to the second position the sun gear shaft rotates and the shuttle frame moves proximally a distance relative to the handle.

11. The system of claim 10, wherein the actuation assembly further comprises an intermediate gear functionally disposed on the shuttle frame between the sun gear shaft and the handle, and operatively engaged with the sun gear shaft.

12. The system of claim 8, wherein the actuation assembly further comprises a ratchet rack fixedly coupled to the inner shaft member and disposed on the shuttle frame.

13. The system of claim 12, wherein the ratchet rack is operatively meshed with the ring gear.

14. The system of claim 8, wherein the actuation assembly further comprises at least one pin configured to engage at least one pin track disposed within the handle to thereby guide the shuttle frame along the handle.

15. The system of claim 14, wherein the at least one pin comprises a first pin disposed through an axis of an intermediate gear functionally disposed on the shuttle frame between the sun gear shaft and the handle, and operatively engaged with the sun gear shaft.

16. The system of claim 15, wherein the at least one pin comprises a second and third pin, each of the second and third pin disposed through the shuttle frame.

17. The system of claim 16, wherein the at least one pin comprises a fourth pin disposed through an axis of the sun gear shaft.

18. The system of claim 8, wherein the actuation assembly further comprises a plate disposed on the shuttle frame.

19. The system of claim 1, wherein the actuation assembly is functionally coupled to the trigger by a diving rack.

20. The system of claim 19, wherein the driving rack is operatively meshed with the planet carrier and the driving rack is supported by the shuttle frame.

21. The system of claim 1, wherein the sun gear shaft comprises a sun gear portion, a sheath pinion, and a clutch engagement portion.

22. The system of claim 1, wherein the planet carrier comprises a circumferential pinion, a clutch component, and at least one pin.

23. The system of claim 1, wherein the ring gear comprises a circumferential pinion and a ring gear portion.

24. The system of claim 1, wherein the first clutch driver and the second clutch driver each comprises a sun gear shaft engagement portion and a clutch portion.

25. A system for delivering a braided implant, comprising:
a handle having a trigger movable between a first position and a second position, the handle further having an actuation assembly operatively coupled to the trigger, the actuation assembly having a planetary gear system, the planetary gear system having:
a planet carrier,
at least one planet gear operatively engaged with the planet carrier,
a sun gear shaft operatively meshed with the planet gears, a ring gear operatively meshed with the planet gears,
a first clutch driver configured to limit the sun gear to uni-directional rotational motion, and
a second clutch driver configured to uni-directionally lock the sun gear and the planet carrier;
an outer tubular member having a proximal end portion and a distal end portion, the outer member operatively coupled to the actuation assembly and movable in a proximal direction relative to the handle;
an inner shaft member having a proximal end portion and a distal end portion, the inner shaft member disposed within the outer tubular member and operatively coupled to the actuation assembly, the inner shaft member being movable distally and proximally relative to the outer tubular member; and
a braided implant disposed within the distal end portion of the outer tubular member and positioned to be engaged by the distal end portion of the inner shaft member when the inner shaft member is moved distally relative to the outer tubular member;
wherein the actuation assembly is configured to displace the outer tubular member in the proximal direction a distance (d) relative to the handle and to separately move the inner shaft member distally a distance (x) relative to the handle upon deployment of the trigger from the first position to the second position, and further wherein the actuation assembly is configured to move the inner shaft member proximally a distance (y) relative to the handle with no displacement of the outer tubular member relative to the handle upon return of the trigger from the second position to the first position.

26. The system of claim 25, wherein the distance (y) minus the distance (x) is substantially equal to the distance (d).

27. The system of claim 25, wherein upon deployment of the trigger from the first position to the second position and return of the trigger from the second position to the first position a net displacement of the inner shaft member relative to the outer tubular member is zero.

28. The system of claim 25, wherein the braided implant has a length, the length of the braided implant being less than the distance (x).

29. The system of claim 25, wherein repeatedly deploying the trigger from the first position to the second position and returning the trigger from the second position to the first position causes the inner shaft member to urge the braided implant out of the outer tubular member.

30. The system of claim 25, where the actuation assembly is configured to displace the distance (d) in the proximal direction relative to the handle upon deployment of the trigger from the first position to the second position.

31. The system of claim 25, wherein the handle is configured to fit within a hand of a user and upon repeated deployment of the trigger from the first position to the second position and return of the trigger from the second position to the first position the actuation assembly is configured to move from a position within the handle distal of the user's hand to a position within the handle proximal of the user's hand.

* * * * *